United States Patent
Varela-Rohena et al.

(10) Patent No.: US 11,597,911 B2
(45) Date of Patent: Mar. 7, 2023

(54) EXPANSION OF POPULATIONS OF T CELLS BY THE USE OF MODIFIED SERUM FREE MEDIA

(71) Applicants: Life Technologies Corporation, Carlsbad, CA (US); The Trustees of the University of Pennsylvania, Philadelphia, PA (US)

(72) Inventors: Angel M. Varela-Rohena, Williamsville, NY (US); Melanie B. Andolina, Collins, NY (US); James L. Riley, Downingtown, PA (US); Andrew Medvec, Philadelphia, PA (US)

(73) Assignees: Life Technologies Corporation, Carlsbad, CA (US); The Trustees of the University of Pennsylvania, Philadelphia, PA (US)

( * ) Notice: Subject to any disclaimer, the term of this patent is extended or adjusted under 35 U.S.C. 154(b) by 550 days.

(21) Appl. No.: 16/487,266

(22) PCT Filed: Feb. 26, 2018

(86) PCT No.: PCT/US2018/019750
§ 371 (c)(1),
(2) Date: Aug. 20, 2019

(87) PCT Pub. No.: WO2018/157072
PCT Pub. Date: Aug. 30, 2018

(65) Prior Publication Data
US 2019/0367874 A1 Dec. 5, 2019

Related U.S. Application Data

(60) Provisional application No. 62/464,233, filed on Feb. 27, 2017.

(51) Int. Cl.
*C12N 5/0783* (2010.01)
*C12N 5/00* (2006.01)

(52) U.S. Cl.
CPC ......... *C12N 5/0636* (2013.01); *C12N 5/0031* (2013.01); *C12N 5/0637* (2013.01); *C12N 2500/34* (2013.01); *C12N 2500/36* (2013.01); *C12N 2500/99* (2013.01); *C12N 2501/00* (2013.01); *C12N 2501/999* (2013.01)

(58) Field of Classification Search
CPC ............................ C12N 5/0636; C12N 5/0637; C12N 2501/00; C12N 2501/999
See application file for complete search history.

(56) References Cited

U.S. PATENT DOCUMENTS

| | | | |
|---|---|---|---|
| 5,399,346 A | 3/1995 | Anderson et al. | |
| 5,580,859 A | 12/1996 | Felgner et al. | |
| 5,589,466 A | 12/1996 | Felgner et al. | |
| 6,326,193 B1 | 12/2001 | Liu et al. | |
| 8,906,682 B2 | 12/2014 | June et al. | |
| 2016/0032343 A1 | 2/2016 | Wu et al. | |
| 2017/0056448 A1* | 3/2017 | Glick | C12N 5/0636 |
| 2018/0228839 A1* | 8/2018 | Shrikant | C12N 5/0636 |

FOREIGN PATENT DOCUMENTS

| | | |
|---|---|---|
| EP | 2 857 509 A1 | 4/2015 |
| EP | 2 857 509 B1 | 4/2015 |
| WO | WO-01/29058 A1 | 4/2001 |
| WO | WO-01/96584 A2 | 12/2001 |
| WO | WO-01/96584 A3 | 12/2001 |
| WO | WO-2017/015024 A1 | 1/2017 |
| WO | WO-2017/024150 A1 | 2/2017 |

OTHER PUBLICATIONS

Akdis M, et al. (Jun. 7, 2004). "Immune responses in healthy and allergic individuals are characterized by a fine balance between allergen-specific T regulatory 1 and T helper 2 cells," J Exp Med 199(11):1567-1575.
Balandina, A. et al. (Jan. 15, 2005). "Functional defect of regulatory CD4(+)CD25+ T cells in the thymus of patients with autoimmune myasthenia gravis," Blood 105:735-741.
Barrett, D.M. et al. (2011). Treatment of advanced leukemia in mice with mRNA engineered T cells. Hum. Gene Ther. 22, 1575-1586.
Barrett, D.M. et al. (2013). Regimen-specific effects of RNA-modified chimeric antigen receptor T cells in mice with advanced leukemia. Hum. Gene Ther. 24, 717-727.
Barrett, D.M. et al. (2014). Chimeric antigen receptor therapy for cancer. Annu. Rev. Med. 65, 333-347.
Barrett, D.M. et al. (2014). Relation of clinical culture method to T-cell memory status and efficacy in xenograft models of adoptive immunotherapy. Cytotherapy 16, 619-630.
Barrett, D.M. et al. (2015). Chimeric antigen receptor- and TCR-modified T cells enter Main Street and Wall Street. J. Immunol. 195, 755-761.
Beckner, S.K. et al. (1987). Lymphokine-activated killer cells: culture conditions for the generation of maximal in vitro cytotoxicity in cells from normal donors. Cancer Res. 47, 5504-5508.
Bettencourt, I.A. et al. (2017). Targeting metabolism as a novel therapeutic approach to autoimmunity, inflammation, and transplantation. J. Immunol. 198, 999-1005.
Blagih, J. et al. (2015). The energy sensor AMPK regulates T cell metabolic adaptation and effector responses in vivo. Immunity 42, 41-54.

(Continued)

*Primary Examiner* — Kara D Johnson
(74) *Attorney, Agent, or Firm* — Mintz, Levin, Cohn, Ferris Glovsky & Popeo, P.C.

(57) ABSTRACT

This invention relates, inter alia, to compositions of low serum or serum free media and methods for the expansion of T cell populations and methods for using such populations of cells. In some aspects, the invention relates to compositions and methods for the selective expansion of T cell subpopulations.

12 Claims, 58 Drawing Sheets

(56) References Cited

OTHER PUBLICATIONS

Bottenstein, J.E. et al. (1979). Growth of a rat neuroblastoma cell line in serum-free supplemented medium. Proc. Natl. Acad. Sci. USA 76, 514-517.

Boudah, S. et al. (2014). Annotation of the human serum metabolome by coupling three liquid chromatography methods to high-resolution mass spectrometry. J. Chromatogr. B Analyt. Technol. Biomed. Life Sci. 966, 34-47.

Brentjens, R.J. et al. (2013). CD19-targeted T cells rapidly induce molecular remissions in adults with chemotherapy-refractory acute lympho-blastic leukemia. Sci. Transl. Med. 5, 177ra38.

Brindley, D.A. et al. (2012). Peak serum: implications of serum supply for cell therapy manufacturing. Regen. Med. 7, 7-13.

Buck, M.D. et al. (Aug. 24, 2015, e-published Aug. 10, 2015). "T cell metabolism drives immunity," *J Exp Med* 212(9):1345-1360.

Cabrera, R. et al. (Nov. 2004). "An immunomodulatory role for CD4(+)CD25(+) regulatory T lymphocytes in hepatitis C virus infection," Hepatology 40(5):1062-1071.

Chang, C-H. et al. (Jun. 6, 2013). "Posttranscriptional control of T cell effector function by aerobic glycolysis," Cell 153(6):1239-1251.

Costello, E. et al. (2000). Gene transfer into stimulated and unstimulated T lymphocytes by HIV-1-derived lentiviral vectors. Gene Ther. 7, 596-604.

Cruz, C.R. et al. (2013). Infusion of donor-derived CD19-redirected virus-specific T cells for B-cell malignancies relapsed after allogeneic stem cell transplant: a phase 1 study. Blood 122, 2965-2973.

Davila, M.L. et al. (2014). Efficacy and toxicity management of 19-28z CAR T cell therapy in B cell acute lymphoblastic leukemia. Sci. Transl. Med. 6, 224ra25.

Fritsch, R.D. et al. (2005). Stepwise differentiation of CD4 memory T cells defined by expression of CCR7 and CD27. J. Immunol. 175, 6489-6497.

Gattinoni, L. et al. (2012). Paths to sternness: building the ultimate antitumour T cell. Nat. Rev. Cancer 12, 671-684.

Grupp, S.A. et al. (2013). Chimeric antigen receptor-modified T cells for acute lymphoid leukemia. N. Engl. J. Med. 368, 1509-1518.

Ham, R.G. (1965). Clonal growth of mammalian cells in a chemically defined, synthetic medium. Proc. Natl. Acad. Sci. USA 53, 288-293.

Himmel, M.E. et al. ((Jun. 2012). "Regulatory T-cell therapy for inflammatory bowel disease: more questions than answers," Immunology 136(2):115-122.

Hollyman, D. et al. (2009). Manufacturing validation of biologically functional T cells targeted to CD19 antigen for autologous adoptive cell therapy. J. Immunother. 32, 169-180.

International Search Report dated May 11, 2018, for PCT Application No. PCT/US2018/019750, filed Feb. 26, 2018, 3 pages.

Iscove, N.N. et al. (1978). Complete replacement of serum by albumin, transferrin, and soybean lipid in cultures of lipopolysaccharide-reactive B lymphocytes. J. Exp. Med. 147, 923-933.

Jensen, M.C. et al. (2015). Designing chimeric antigen receptors to effectively and safely target tumors. Curr. Opin. Immunol. 33, 9-15.

Jeon, M.K. et al. (Sep. 21, 2010). "Development of a serum-free medium for in vitro expansion of human cytotoxic T lymphocytes using a statistical design," *BMC Biotechnol* 10:70.

Kalos, M. et al. (2011). T cells with chimeric antigen receptors have potent antitumor effects and can establish memory in patients with advanced leukemia. Sci. Transl. Med. 3, 95ra73.

Klebanoff, C.A. et al. (2012). Sorting through subsets: which T-cell populations mediate highly effective adoptive immunotherapy? J. Immunother. 35, 651-660.

Klebanoff, C.A. et al. (2016). Memory T cell-driven differentiation of naive cells impairs adoptive immunotherapy. J. Clin. Invest. 126, 318-334.

Kochenderfer, J.N. et al. (2010). Eradication of B-lineage cells and regression of lymphoma in a patient treated with autologous T cells genetically engineered to recognize CD19. Blood 116, 4099-4102.

Kriegel, M.A. et al. (May 3, 2004). "Defective suppressor function of human CD4+ CD25+ regulatory T cells in autoimmune polyglandular syndrome type II," J. Exp. Med. 199:1285-1291.

Lee, D.W. et al. (2015). T cells expressing CD19 chimeric antigen receptors for acute lymphoblastic leukaemia in children and young adults: a phase 1 dose-escalation trial. Lancet 385, 517-528.

Leibman, R.S. et al. (2015). Engineering T cells to functionally cure HIV-1 infection. Mol. Ther. 23, 1149-1159.

Lindley, S. et al. (Jan. 2005). "Defective suppressor function in CD4(+)CD25(+) T-cells from patients with type 1 diabetes," Diabetes 54(1):92-99.

Liyanage, U.K. et al.(2002). "Prevalence of regulatory T cells is increased in peripheral blood and tumor microenvironment of patients with pancreas or breast adenocarcinoma," J Immunol 2002; 169:2756-2761.

Lu, T.L. et al. (Dec. 2016). "A Rapid Cell Expansion Process for Production of Engineered Autologous CAR-T Cell Therapies," *Hum Gene Ther Methods* 27(6):209-218.

Lundgren, A, et al. (Apr. 2003). "Helicobacter pylori-specific CD4+ CD25high regulatory T cells suppress memory T-cell responses to H. pylori in infected individuals," Infect Immun 71:1755-1762.

Ma, E.H. et al. (2017). Serine is an essential metabolite for effector T cell expansion. Cell Metab. 25, 345-357.

Maciver, N.J. et al. (2013). Metabolic regulation of T lymphocytes. Annu. Rev. Immunol. 31, 259-283.

Maude, S.L. et al. (2014). Chimeric antigen receptor T cells for sustained remissions in leukemia. N. Engl. J. Med. 371, 1507-1517.

McVicar, D.W. et al. (1991). A comparison of serum-free media for the support of in vitro mitogen-induced blastogenic expansion of cytolytic lymphocytes. Cytotechnology 6, 105-113.

Medvec, A.R. et al. (e-collection Mar. 16, 2018, Nov. 2017). "Improved Expansion and In Vivo Function of Patient T Cells by a Serum-free Medium," *Mol Ther Methods Clin Dev* 8:65-74.

Milone, M.C. et al. (2009). Chimeric receptors containing CD137 signal transduction domains mediate enhanced survival of T cells and increased antileukemic efficacy in vivo. Mol. Ther. 17, 1453-1464.

Moore, G.E. et al. (1967). Culture of normal human leukocytes. JAMA 199, 519-524.

Okada, R. et al. (2008). Phenotypic classification of human CD4+ T cell subsets and their differentiation. Int. Immunol. 20, 1189-1199.

Olenchock, B.A. et al. (2017). Biochemical underpinnings of immune cell metabolic phenotypes. Immunity 46, 703-713.

Papadopoulou, A. et al. (2014). Systemic inflammatory response syndrome after administration of unmodified T lymphocytes. Mol. Ther. 22, 1134-1138.

Parry, R.V. et al. (2003). CD28 and inducible costimulatory protein Src homology 2 binding domains show distinct regulation of phosphatidylinositol 3-kinase, Bcl-xL, and IL-2 expression in primary human CD4 T lymphocytes. J. Immunol. 171, 166-174.

Porter, D.L. et al. (2011). Chimeric antigen receptor-modified T cells in chronic lymphoid leukemia. N. Engl. J. Med. 365, 725-733.

Porter, D.L. et al. (2015). Chimeric antigen receptor T cells persist and induce sustained remissions in relapsed refractory chronic lymphocytic leukemia. Sci. Transl. Med. 7, 303ra139.

Psychogios, N. et al. (2011). The human serum metabolome. PLoS One 6, e16957.

Rapoport, A.P. et al. (2005). Restoration of immunity in lymphopenic individuals with cancer by vaccination and adoptive T-cell transfer. Nat. Med. 11, 1230-1237.

Richardson, M.W. et al. (2014). Stabilized human TRIM5α protects human T cells from HIV-1 infection. Mol. Ther. 22, 1084-1095.

Riley, J.L. et al. (2009). Human T regulatory cell therapy: take a billion or so and call me in the morning. Immunity 30, 656-665.

Rosenberg, S.A. et al. (2015). Adoptive cell transfer as personalized immunotherapy for human cancer. Science 348, 62-68.

Sadelain, M. (2015). CAR therapy: the CD19 paradigm. J. Clin. Invest. 125, 3392-3400.

Sato, K. et al. (2009). Impact of culture medium on the expansion of T cells for immunotherapy. Cytotherapy 11, 936-946.

(56) References Cited

OTHER PUBLICATIONS

Singh, H. et al. (2013). Manufacture of clinical-grade CD19-specificT cells stably expressing chimeric antigen receptor using Sleeping Beauty system and artificial antigen presenting cells. PLoS One 8, e64138.

Singh, N. et al. (2016). Early memory phenotypes drive T cell proliferation in patients with pediatric malignancies. Sci. Transl. Med. 8, 320ra3.

Stoop, J.N. et al. (Apr. 2005). "Regulatory T cells contribute to the impaired immune response in patients with chronic hepatitis B virus infection," Hepatology 2005; 41:771-778.

Sugimoto, K. et al. (2003). "Suppression of HCV-specific T cells without differential hierarchy demonstrated ex vivo in persistent HCV infection," Hepatology 38:1437-1448.

Sugiyama, H. et al. ((Jan. 1, 2005). "Dysfunctional blood and target tissue CD4+CD25high regulatory T cells in psoriasis: mechanism underlying unrestrained pathogenic effector T cell proliferation," J. Immunol. 174:164-173.

Thomas, A.K et al. (2002). A cell-based artificial antigen-presenting cell coated with anti-CD3 and CD28 antibodies enables rapid expansion and long-term growth of CD4 T lymphocytes. Clin. Immunol. 105, 259-272.

Tiemessen, M.M. et al. (May 2004). "Cow's milk-specific T-cell reactivity of children with and without persistent cow's milk allergy: key role for IL-10," J Allergy Clin Immunol 113(5):932-939.

Tomiyama, H. et al. (2002). Differentiation of human CD8(+) T cells from a memory to memory/effector phenotype. J. Immunol. 168, 5538-5550.

Tumaini, B. et al. (2013). Simplified process for the production of anti-CD19-CAR-engineered T cells. Cytotherapy 15, 1406-1415.

Van Der Windt, G.J. et al. (2012). Metabolic switching and fuel choice during T-cell differentiation and memory development. Immunol. Rev. 249, 27-42.

Varela-Rohena, A. et al. (2008). Control of HIV-1 immune escape by CD8 T cells expressing enhanced T-cell receptor. Nat. Med. 14, 1390-1395.

Viglietta et al. (Apr. 5, 2004). "Loss of functional suppression by CD4+CD25+ regulatory T cells in patients with multiple sclerosis," J. Exp. Med. 199:971-979.

Viguier M, et al. (2004). "Foxp3 expressing CD4+CD25(high) regulatory T cells are overrepresented in human metastatic melanoma lymph nodes and inhibit the function of infiltrating T cells," J Immunol 173:1444-1453.

Wei, F. et al. (2013). Strength of PD-1 signaling differentially affects T-cell effector functions. Proc. Natl. Acad. Sci. USA 110, E2480-E2489.

Wilkens, C.A. et al. (Oct. 5, 2011). "Comparative Metabolic Analysis of Lactate for CHO Cells in Glucose and Galactose," *Biotechnology and Bioprocess Engineering* 16:714-724.

Wolf, A.M. et al. (2003). "Increase of regulatory T cells in the peripheral blood of cancer patients," Clin Cancer Res 9(2):606-612.

Woo, E.Y. et al. (May 1, 2002). "Cutting edge: Regulatory T cells from lung cancer patients directly inhibit autologous T cell proliferation," J Immunol 168(9):4272-4276.

Written Opinion dated May 11, 2018, for PCT Application No. PCT/US2018/019750, filed Feb. 26, 2018, 9 pages.

Yu, M. et al. (2011). Regulation of T cell receptor signaling by activation-induced zinc influx. J. Exp. Med. 208, 775-785.

\* cited by examiner

1 —— 100% Glucose
2 ---- 80% Glucose, 20% Galactose
3 —— 50% Glucose, 50% Galactose
4 ------ 20% Glucose, 80% Galactose
5 – – 100% Galactose
6 ---- X-VIVO 15 hAB 1 —— 100% Glucose
2 ---- 80% Glucose, 20% Galactose
3 —— 50% Glucose, 50% Galactose
4 ······ 20% Glucose, 80% Galactose
5 — — 100% Galactose
6 ---- X-VIVO 15 hAB

| | | |
|---|---|---|
| 1 —— | 100% Glucose | |
| 2 ---- | 80% Glucose, 20% Galactose | |
| 3 —— | 50% Glucose, 50% Galactose | |
| 4 ······ | 20% Glucose, 80% Galactose | |
| 5 – – | 100% Galactose | |
| 6 ---- | X-VIVO 15 hAB | |

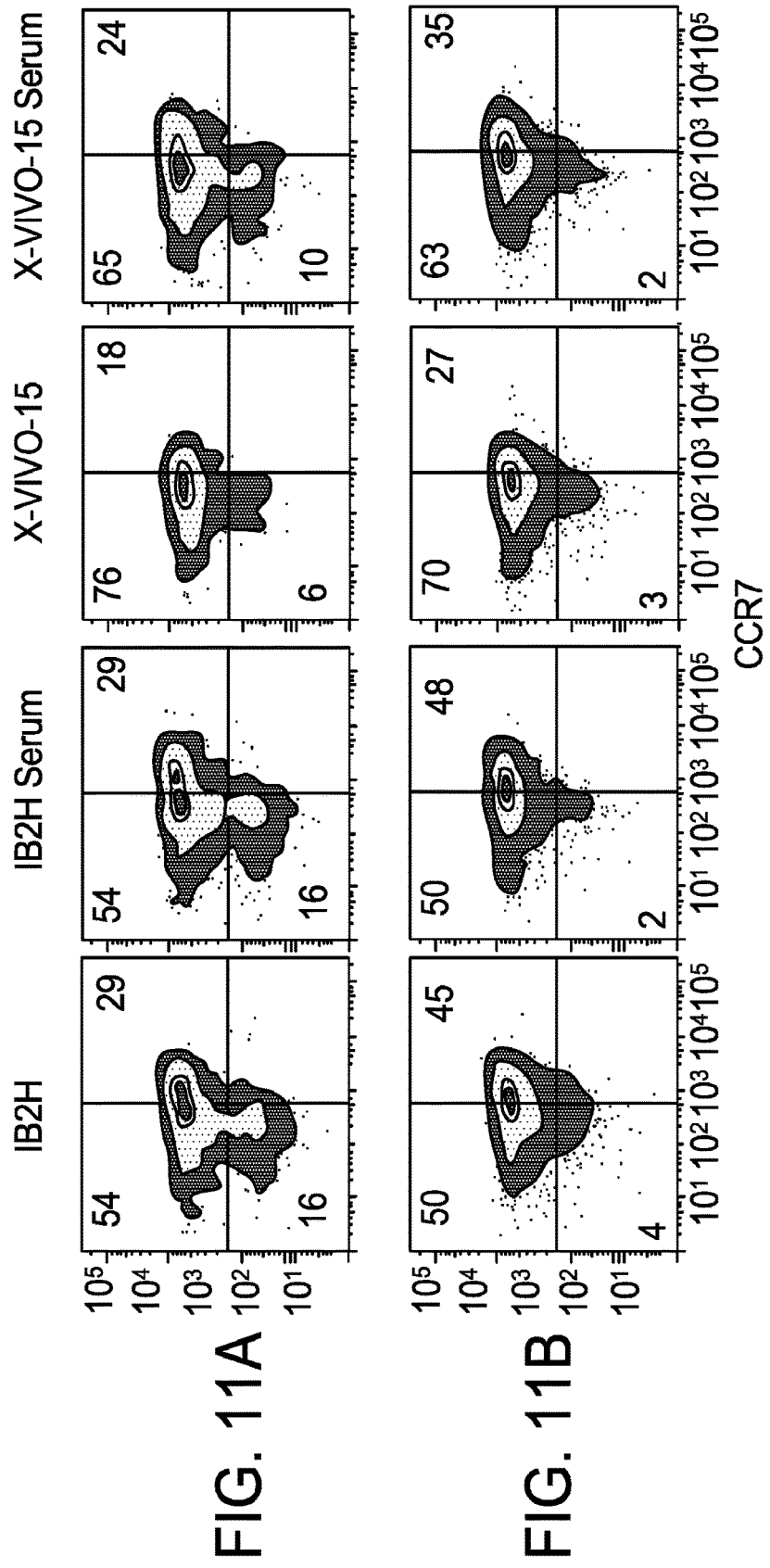

EXPANSION OF POPULATIONS OF T CELLS BY THE USE OF MODIFIED SERUM FREE MEDIA

RELATED APPLICATIONS

This application is a U.S. National Phase Application of PCT International Application No. PCT/US2018/019750, filed on Feb. 26, 2018, designating the United States of America, which is an International Application of and claims the benefit of priority under 35 U.S.C. § 119(e) to United States Provisional Application 62/464,233, filed on Feb. 27, 2017, and titled "Expansion of Populations of T Cells by the Use of Modified Serum Free Media." The disclosures of the above-referenced applications are hereby expressly incorporated by reference in their entireties.

STATEMENT REGARDING FEDERALLY SPONSORED R&D

This invention was made with government support under CA147795 awarded by the National Institutes of Health. The government has certain rights in the invention.

FIELD OF THE INVENTION

This invention relates, inter alia, to compositions of serum free media and methods for the expansion of T cell populations and methods for using such populations of cells. In some aspects, the invention relates to compositions and methods for the selective expansion of T cell subpopulations present in mixed T cell populations.

BACKGROUND OF THE INVENTION

The ability of T cells to recognize the universe of antigens associated with, for example, various cancers or infectious organisms is conferred by T cell antigen receptor (TCR), which is made of both an a (alpha) chain and a β (beta) chain or a γ (gamma) and a δ (delta) chain. T cells and various subsets have broad ranging therapeutic implications in the treatment of cancers, autoimmune disorders, inflammatory diseases, allergic diseases, and infectious diseases. Therefore, there is a long felt need for reliable, efficient and rapid way to expand specific immune subpopulations.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

SUMMARY OF THE INVENTION

The present invention provides, inter alia, compositions and methods for the expansion of T cell populations using formulations of low serum or serum free media. In some embodiments, T cell subpopulations include, but are not limited to: (1) regulatory T cells (Treg), a suppressive subset of CD4$^+$ T helper cells important for the regulation of immune responses; (2) Th17 cells, an inflammatory subset of CD4+ T helper cells that regulate host defense, and are involved in tissue inflammation and various autoimmune diseases; (3) Th9 cells, an inflammatory subset of CD4+ T helper cells that regulate host defense, and are involved in allergy, inflammation and various autoimmune diseases; (4) memory T cells, or antigen specific T cells, a long lasting cell type that retains immunity to prior exposed antigens; and (5) engineered T cells. Disclosed herein are methods and compositions for the expansion of T cell populations using a modified serum free media that includes galactose and glucose. Methods and compositions described herein can be used, in part, to generate T cell populations for research purposes and/or for clinical use. The resultant expanded T cell populations have wide ranging uses in clinical settings.

The invention relates, in part, to cell culture media comprising glucose:galactose in a ratio of about 10:90, as well as methods for using such cell culture media. In some aspects, the media may be substantially serum-free. In other aspects, the media is serum-free. In some aspects, the media is for culturing T cells. T cells used in the practice of the invention may be selected from the group including T regulatory cells (Tregs), T helper cells, Th17 cells, Th9 cells, T memory cells, T effector memory cells, T central memory cells, terminally differentiated effector (TTD) T cells, naïve T cells, and engineered T cells. In some aspects, cell culture media of the invention contains glucose:galactose in a ratio including 10:90, 15:85, 20:80, 25:75, 30:70, 35:65, 40:60, 45:55, 50:50, 55:45, 60:40, 65:35, 70:30, 75:25, 80:20, 85:15, and 90:10 (e.g., from about 10:90 to about 90:10, from about 20:80 to about 90:10, from about 30:70 to about 90:10, from about 40:60 to about 90:10, from about 10:90 to about 80:20, from about 10:90 to about 70:30, from about 10:90 to about 60:40, from about 20:80 to about 80:20, from about 30:70 to about 70:30, from about 40:60 to about 60:40, from about 45:55 to about 55:45, from about 47:53 to about 53:47, etc.). In some aspects, the cell culture media contains one or more of fatty acids, cholesterol, arachidonic acid, linoleic acid, linolenic acid, myristic acid, oleic acid, palmitic acid, palmitoleic acid and stearic acid. In some aspects the media is sterile.

In some aspects, cells cultured in media of the invention are capable of: greater retention of phenotype, greater expansion, greater potency, and/or higher transduction efficiency when compared to cells not cultured in the media.

The invention also includes methods for culturing a population of cells comprising one or more T cells, the methods comprising: obtaining T cells from a subject; inoculating glucose:galactose serum media with said T cells; growing the culture of T cells for a sufficient period of time to determine the T cells have reached the desired number, stage of differentiation, and/or phenotype; and harvesting the T cells from the culture. In some aspects, growing further includes screening the T cells for the presence or absence of makers associated with a desired T cell type. The markers may include CD3, CD4, CD8, CCR7, CD19, CD27, CD28, and CD45RA. In some aspects, the media further comprises lipids. The lipids may include one or more of fatty acids, cholesterol, arachidonic acid, linoleic acid, linolenic acid, myristic acid, oleic acid, palmitic acid, palmitoleic acid and stearic acid. The method may be used to selectively expand a population of T cells. The T cells may be include: Tregs, Th17 cells, Th9 cells, T memory cells, naïve T cells, and engineered T cells. In some aspects, the T cells produced by the method have greater retention of phenotype, greater expansion, greater potency, and/or higher transduction efficiency when compared to cells not cultured in the media.

The invention also includes compositions and methods for treating a disease or condition where the methods comprise: culturing a population of cells comprising one or more T cells comprising: obtaining T cells from a subject; inoculating glucose:galactose serum media with the T cells; growing the culture of T cells for a sufficient period of time to determine the T cells have reached the desired number, stage of differentiation, and/or phenotype; harvesting the T cells from the culture; preparing the harvested T cells for administration to a subject suffering from or at risk of suffering from said disease or condition; and administering the T cells to the subject. In some aspects, different subjects are providing and receiving T cells. In some aspects the disease or condition includes hyperproliferative disorder (e.g., cancer), autoimmune disease, allergy, inflammation, and infectious disease. Administering may further include performing adoptive transfer of T cells on a subject. The T cell may be selected from the group consisting of T regulatory cells (Tregs), T helper cells, Th17 cells, Th9 cells, T memory cells, T effector memory cells, T central memory cells, terminally differentiated effector (TTD) T cells, naïve T cells, and engineered T cells. In some aspects, the engineered T cell is a chimeric antigen receptor (CAR) T cell. The CAR T cell may be CD19 CAR T cell.

The invention also includes kits for culturing T cells. In some aspects, such kits may comprise: serum free media, glucose:galactose, and one or more lipids. In some aspects, the glucose:galactose is present in a ratio including 10:90, 15:85, 20:80, 25:75, 30:70, 35:65, 40:60, 45:55, 50:50, 55:45, 60:40, 65:35, 70:30, 75:25, 80:20, 85:15, and 90:10 glucose:Galactose (e.g., from about 10:90 to about 90:10, from about 20:80 to about 90:10, from about 30:70 to about 90:10, from about 40:60 to about 90:10, from about 10:90 to about 80:20, from about 10:90 to about 70:30, from about 10:90 to about 60:40, from about 20:80 to about 80:20, from about 30:70 to about 70:30, from about 40:60 to about 60:40, from about 45:55 to about 55:45, from about 47:53 to about 53:47, etc.). In some aspects, the lipid includes one or more of fatty acids, cholesterol, arachidonic acid, linoleic acid, linolenic acid, myristic acid, oleic acid, palmitic acid, palmitoleic acid and stearic acid.

The invention also includes a population of T cells cultured in a cell media comprising glucose:galactose in a ratio of about 10:90. In some aspects, a population of T cells cultured in a cell media includes glucose:galactose in a ratio selected from the group including 10:90, 15:85, 20:80, 25:75, 30:70, 35:65, 40:60, 45:55, 50:50, 55:45, 60:40, 65:35, 70:30, 75:25, 80:20, 85:15, and 90:10 and ranges set out herein. In some aspects, a population of T cells is cultured in media substantially free of serum. In some aspects, a population of T cells includes T cells that are selected from the group consisting of T regulatory cells (Tregs), T helper cells, Th17 cells, Th9 cells, T memory cells, T effector memory cells, T central memory cells, terminally differentiated effector ($T_{TD}$) T cells, naïve T cells, and engineered T cells. In some aspects, a population of T cells cultured in a cell media is capable of: greater retention of phenotype, greater expansion, greater potency, and/or higher transduction efficiency when compared to cells not cultured in the media.

Each of the aspects and embodiments described herein are capable of being used together, unless excluded either explicitly or clearly from the context of the embodiment or aspect.

BRIEF DESCRIPTION OF THE DRAWINGS

FIG. 1 shows memory T cells favoring the oxidative phosphorylation (OXPHOS) metabolic pathway as described in Buck et al. (Buck et al. J. Exp. Med. 2015 Vol. 212 No. 9 1345-1360), incorporated by reference herein.

FIG. 2A depicts cells grown in glucose rich media derive ATP from glycolysis as well as from glutamine-driven respiration. FIG. 2B demonstrates that replacing glucose with galactose forces cells to generate ATP almost exclusively from oxidative metabolism. (TCA=Tricarboxylic Acid; ETC=Electron Transport Chain). FIG. 2C is a graph depicting the measurement of the extracellular acidification rate (ECAR), a proxy for the rate of glycolysis, and oxygen consumption rate (OCR), a proxy for mitochondrial respiration, of fibroblasts grown in 10 mM glucose or 10 mM galactose containing media for three days. Cells cultured in galactose without glucose experienced little growth compared to cells grown in glucose. Data are expressed as mean±SD (n=5).

FIG. 3 demonstrates that D-galactose alone is not sufficient to support optimal in vitro T cell expansion, while combinations of glucose and galactose at 30%, 50% and 70% expand T cells comparably to media with just glucose.

FIG. 4A is a graph depicting expansion of T cells in the indicated medium was expressed as population doublings over time—noticeable superior cell culture performance of 3 g/L glucose+3 g/L galactose medium versus 3 g/L glucose medium. FIG. 4B is a graph depicting glucose analysis from T cell culture supernatants. Consumption of glucose was detected in all cultures from day 0 to day 3 pre-feeding as well as post-fed supernatant on Day 3 to Day 6. FIG. 4C is a graph depicting galactose analysis from T cell culture supernatant. No appreciable consumption of Galactose was detected, even in conditions with depleted glucose as shown in FIG. 4B. These results demonstrate that while galactose is not metabolized by T cells, its presence in T cell culture medium provides a cell growth advantage that was not related to its catabolism.

FIG. 8A is a graph depicting that primary human T cells from normal donors were negatively isolated from PBMCs with DYNABEADS® UNTOUCHED™ Human T Cells kit. T cells (seeding density $1 \times 10^6$/mL) were activated with DYNABEADS® Human T-Expander CD3/CD28 at a ratio of 3 beads per T cell and cultured in serum-free medium supplemented with GIBCO™ Chemically Defined Lipid Concentrate (1:100) and 3 g/L each glucose and galactose; Control Medium Lonza X-VIVO™ 15 supplemented with 5% human AB serum. T cells were counted on days 3, 5, 7 and 10 on a Beckman-Coulter ViCell analyzer and fed to a density of $5 \times 10^5$ cells/mL on days 3 and 7. T cell expansion is expressed as population doublings over time. FIG. 8B depicts the gating strategy for differentiation phenotyping. Expanded T cells were stained with antibodies against CD3, CD4, CD8, CD45RA, CD27 and CCR7. Sequential gating was used to characterize T cells as naïve (TN: CD45RA+/CD27+/CCR7+), terminally differentiated effectors (TTD: CD45RA+/CD27–/CCR7–), central memory (TCM: CD45RA–/CD27+/CCR7+); and effector memory (TEM: CD45RA–/CD27–/CCR7–). Flow cytometric analysis was performed in a Beckman-Coulter Gallios analyzer. FIG. 8C depicts the differentiation status of CD4+ T cells expanded in control or glucose/galactose media compared to original subset distribution (Day 0). FIG. 8D depicts the differentiation status of CD8+ T cells expanded in control or glucose/galactose media compared to original subset distribution (Day 0). Results demonstrate a more favorable phenotype of T cells expanded in glucose/galactose medium as defined by greater frequencies of naïve and memory cell subsets at harvest versus control medium.

FIG. 9 demonstrates 99% retention of CD8+ T cells post expansion in glucose/galactose serum-free medium when compared to the frequencies in control media. Of note, serum supplementation has a slight negative effect in glucose/galactose medium when compared to control media which shows similar CD8+ T cell frequencies irrespective of serum supplementation.

FIG. 10D-FIG. 10E depicts CD4 Naïve (CD45RA+, CD27+, CCR7+, CD25−) T cells (FIG. 10D) and CD4 effector memory (CD45RA−, CD27−, CCR7−) T cells (FIG. 10E). FIG. 10F shows that T cells from FIG. 10D and FIG. 10E were sorted and expanded using CD3/28 using the indicated media in the presence and absence of 5% human serum.

FIG. 11A-FIG. 11I is a series of graphs demonstrating that T cells from multiple myeloma patients expand better in glucose/galactose serum free media (1B2H). FIG. 11A and FIG. 11B are graphs of sorted T cells grown in 1B2H (with and without serum) compared to T cells grown in X-VIVO-15 (with and without serum). T cells were sorted based on the markers CD27 and CCR7. FIG. 11C is a graph comparing percent expression of CD27-CCR7− in T cells grown in X-VIVO-15, 1B2H, and serum. T cells from cancer patients expand more efficiently in glucose/galactose medium. T cells from cancer patients are generally more differentiated and more difficult to expand than T cells from healthy donors. As demonstrated in FIG. 11C, serum free media (e.g., 1B2H) expanded differentiated T cells more effectively than X-VIVO™ 15 with or without human serum supplementation. FIG. 11D and FIG. 11E are graphs depicting population doublings over time of T cells grown in 1B2H (with and without serum) compared to T cells grown in X-VIVO-15 (with and without serum). FIG. 11F and FIG. 11H depict FACS results for T cells (naïve and memory T cells) cultured in 1B2H media (with or without serum) versus X-VIVO-15 media (with or without serum). CCR7 and CD27 were used as markers. FIG. 11F depicts naïve T cells while memory T cells are demonstrated in FIG. 11H. FIG. 11G and FIG. 11I are graphs depicting the results of the FACS analysis for FIG. 11F and FIG. 11H. FIG. 11G and FIG. 11I depict naïve and memory T cells, respectively.

FIG. 13A and FIG. 13B demonstrates that glucose:galactose media enhances serum free lentiviral transduction efficiency. To assess whether T cells expanded in glucose/galactose (1B2H)-containing medium were amenable to lentiviral transduction, T cells cultured in 1B2H or Lonza X-VIVO™ 15 were stimulated without serum supplementation (black bars) or in the presence of 1 of 6 human serum lots (grey bars), and then transduced the activated T cells with a range of dilutions of a GFP expressing lentiviral vector. There was considerable variability in the transduction efficiency of T cells cultured in the presence of the various lots of serum for both media. However, in most cases, higher transduction efficiency was observed in T cells cultured in X-VIVO 15 in the presence of human serum (compare the 1:27 and 1:81 dilutions which are in the linear range, than in X-VIVO 15 serum-free, as depicted in FIG. 13A. In contrast, T cells cultured in serum-free 1B2H were just as susceptible to lentiviral transduction as T cells grown in the presence of human serum, and superior to those transduced in X-VIVO 15 serum-free, as depicted in FIG. 13B.

FIG. 32A is a graph depicting T central memory cells ND405 responding to galactose. FIG. 32B is a graph depicting T naive cells ND405 responding to galactose.

DETAILED DESCRIPTION

Figure 1:
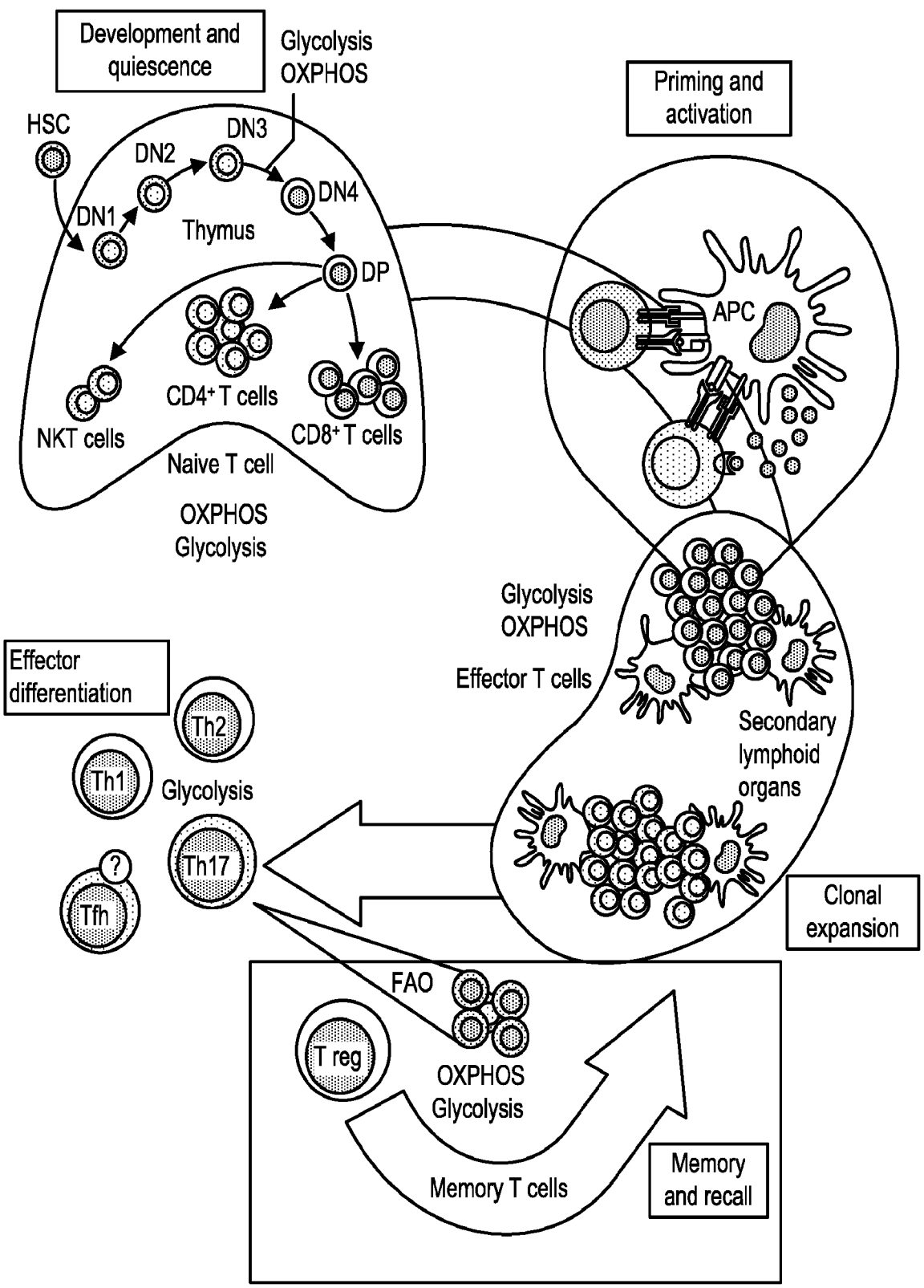
FIG. 1 is schematic representation of cellular energy metabolism pathways at different T cell differentiation stages.
Figure 2C:
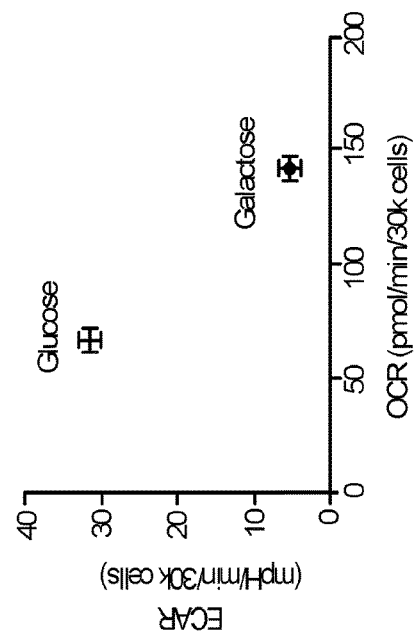
FIG. 2A-FIG. 2C is series of diagrams and graphs depicting the cellular generation of energy from glucose and galactose as described in Gohil et al. (Gohil et al. Nat Biotechnol. 2010; 28(3): 249-255), incorporated by reference herein.
Figure 2B:
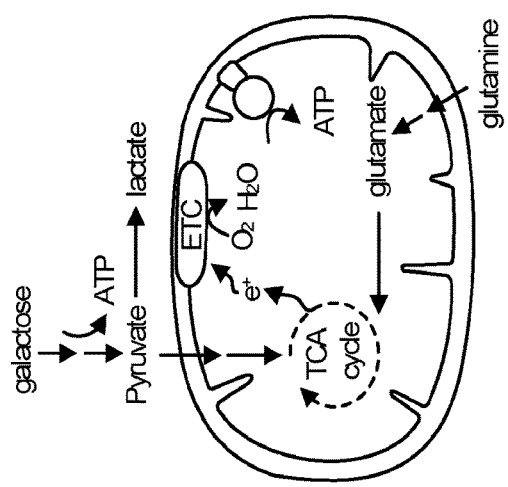
Figure 2A:
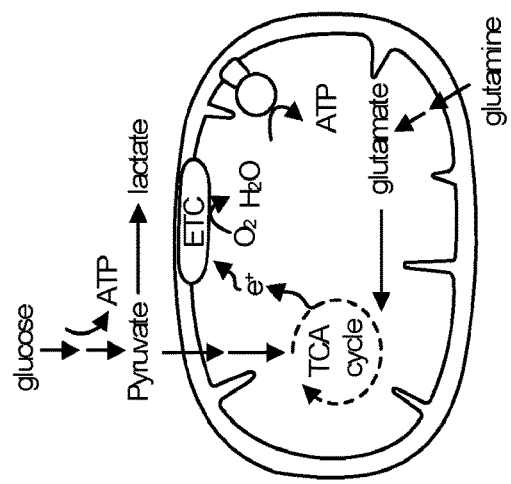

The present invention provides, inter alia, cell media, methods and compositions for the expansion of T cell populations. These T cell populations include, but are not limited to, Th17 cells, Th9 cells, regulatory T cells (Tregs), memory T cells, and engineered T cells (e.g., CAR T cells). The specific T cell subpopulations disclosed herein can be used for the treatment of various physiological conditions, diseases, and/or disease states.

Improvements to T cell culturing systems that promote long-term engraftment and function of adoptively transferred T cells will likely result in superior clinical benefit to more individuals. As described herein, a synthetic media that robustly expands human T cells in absence of human serum was developed. T cells for adoptive T cell transfer may be cultured in a media optimized for patient T cells in the absence of human serum.

I. Definitions

Unless defined otherwise herein, all technical and scientific terms used herein have the same meaning as commonly understood by one of ordinary skill in the art to which this invention pertains.

Antibodies for use in methods of the present invention may be of any species, class or subtype providing that such antibodies can react with the target of interest, e.g., CD3, the TCR, or CD28 as appropriate.

Thus "antibodies" for use in the present invention include:

(a) any of the various classes or sub-classes of immunoglobulin (e.g., IgG, IgA, IgM, IgD or IgE derived from any animal, e.g., any of the animals conventionally used, e.g., sheep, rabbits, goats, mice, camelids, or egg yolk), (b) monoclonal or polyclonal antibodies, (c) intact antibodies or fragments of antibodies, monoclonal or polyclonal, the fragments being those which contain the binding region of the antibody, e.g., fragments devoid of the Fc portion (e.g., Fab, Fab', F(ab')2, scFv, $V_H$H, or other single domain antibodies), the so called "half molecule" fragments obtained by reductive cleavage of the disulphide bonds connecting the heavy chain components in the intact antibody. Fv may be defined as a fragment containing the variable region of the light chain and the variable region of the heavy chain expressed as two chains.

(d) antibodies produced or modified by recombinant DNA or other synthetic techniques, including monoclonal antibodies, fragments of antibodies, "humanized antibodies", chimeric antibodies, or synthetically made or altered antibody-like structures.

Also included are functional derivatives or "equivalents" of antibodies e.g., single chain antibodies, CDR-grafted antibodies etc. A single chain antibody (SCA) may be defined as a genetically engineered molecule containing the variable region of the light chain, the variable region of the heavy chain, linked by a suitable polypeptide linker as a fused single chain molecule.

Methods of preparation of antibody fragments and synthetic and derivatized antibodies are well known in the art and widely described in the literature and are not be described herein.

The term "activation," as used herein, refers to the state of a cell following sufficient cell surface moiety ligation to induce a measurable morphological, phenotypic, and/or functional change. Within the context of T cells, such activation may be the state of a T cell that has been sufficiently stimulated to induce cellular proliferation. Activation of a T cell may also induce cytokine production and/or secretion, and up- or down-regulation of expression of cell surface molecules such as receptors or adhesion molecules, or up- or down-regulation of secretion of certain molecules, and performance of regulatory or cytolytic effector functions. Within the context of other cells, this term infers either up- or down-regulation of a particular physicochemical process.

The term "stimulation," as used herein, refers to a primary response induced by ligation of a cell surface moiety. For example, in the context of receptors, such stimulation entails the ligation of a receptor and a subsequent signal transduction event. With respect to stimulation of a T cell, such stimulation refers to the ligation of a T cell surface moiety that in one embodiment subsequently induces a signal transduction event, such as binding the TCR/CD3 complex. Further, the stimulation event may activate a cell and up- or down-regulate expression of cell surface molecules such as receptors or adhesion molecules, or up- or down-regulate secretion of a molecule, such as down-regulation of Tumor Growth Factor beta (TGF-β). Thus, ligation of cell surface moieties, even in the absence of a direct signal transduction event, may result in the reorganization of cytoskeletal structures, or in the coalescing of cell surface moieties, each of which could serve to enhance, modify, or alter subsequent cell responses.

The term "agent", "ligand", or "stimulatory agent", as used herein, refers to a molecule that binds to one or more defined population of cells (e.g., members of T cell subpopulations) and induces a cellular response. The agent may bind any cell surface moiety, such as a receptor, an antigenic determinant, or other binding site present on the target cell population. The agent may be a protein, peptide, antibody and antibody fragments thereof, fusion proteins, synthetic molecule, an organic molecule (e.g., a small molecule), or the like. Within the specification and in the context of T cell stimulation, antibodies are used as a prototypical example of such an agent.

The term "differentiation", as used herein, refers to a stage in development of the life cycle of a cell. T cells originate from hematopoietic stem cells in the bone marrow and generate a large population of immature thymocytes. The thymocytes (or T cells) progress from double negative cells to become double-positive thymocytes (CD4+CD8+), and finally mature to single-positive (CD4+CD8− or CD4−CD8+). During T cell differentiation, the naïve T cell becomes a blast cell that proliferates by clonal expansion and differentiates into memory and effector T cells. Many subsets of helper T cells (Th cells) are created during T cell differentiation and perform different functions for the immune system. In some embodiments, the differentiation stage of a T cell may be assessed through the presence or absence of markers including, but not limited to, CD3, CD4, CD5, CD8, CD11c, CD14, CD19, CD20, CD25, CD27, CD33, CD34, CD45, CD45RA, CD45RB, CD56, CD62L, CD123, CD127, CD278, CD335, CCR7, and FOXP3.

The term "fluorescence-activated cell sorting (FACS)" as used herein, refers to a specialized type of flow cytometry. FACS provides a method for sorting a heterogeneous mixture of biological cells into two or more containers, one cell at a time, based upon the specific light scattering and fluorescent characteristics of each cell. FACS provides fast, objective and quantitative recording of fluorescent signals from individual cells as well as physical separation of cells of particular interest.

The term "fatty acid" as used herein refers to a carboxylic acid with a long aliphatic chain, which is either saturated or unsaturated. Most naturally occurring fatty acids have an unbranched chain of an even number of carbon atoms, from 4 to 28. Fatty acids are usually derived from triglycerides or phospholipids. When metabolized, fatty acids yield large quantities of ATP. Many cell types can use either glucose or fatty acids for this purpose.

The term "glucose" as used herein refers to a simple sugar with the molecular formula $C_6H_{12}O_6$. It is made during photosynthesis from water and carbon dioxide, using energy from sunlight. The reverse of the photosynthesis reaction, which releases this energy, is an important source of power for cellular respiration. Glucose is stored as a polymer, in plants as starch and in animals as glycogen, for times when the organism will need it. With 6 carbon atoms, it is classed as a hexose, a sub-category of the monosaccharides. D-glucose is one of the 16 aldohexose stereoisomers. The D-isomer, D-glucose, also known as dextrose, occurs widely in nature, but the L-isomer, L-glucose, does not.

The term "galactose (Gal)" as used herein refers to a monosaccharide sugar that is less sweet than glucose and fructose. It is a C-4 epimer of glucose. Galactan is a polymeric form of galactose found in hemicellulose. Galactan can be converted to galactose by hydrolysis.

The term "lipid" as used herein refers to a group of naturally occurring molecules that include fats, waxes, sterols, fat-soluble vitamins (such as vitamins A, D, E, and K), monoglycerides, diglycerides, triglycerides, phospholipids, and others. The main biological functions of lipids include storing energy, signaling, and acting as structural components of cell membranes. Lipids may be broadly defined as hydrophobic or amphiphilic small molecules; the amphiphilic nature of some lipids allows them to form structures such as vesicles, multilamellar/unilamellar liposomes, or membranes in an aqueous environment. Biological lipids originate from two distinct types of biochemical subunits isoprene and ketoacyl groups. Lipids may be divided into the following categories: fatty acids, glycerolipids, glycerophospholipids, sphingolipids, saccharolipids, and polyketides (derived from condensation of ketoacyl subunits); and sterol lipids and prenol lipids (derived from condensation of isoprene subunits). Fats are a subgroup of lipids called triglycerides. Lipids also encompass molecules such as fatty acids and their derivatives (including tri-, di-, monoglycerides, and phospholipids), as well as other sterol-containing metabolites such as cholesterol.

The term "exposing" as used herein, refers to bringing into the state or condition of immediate proximity or direct contact.

The term "oxidative phosphorylation (OXPHOS)" refers to the metabolic pathway in which cells use enzymes to oxidize nutrients, releasing energy used to reform ATP. This takes place inside mitochondria. Almost all aerobic organisms carry out oxidative phosphorylation. This pathway is a highly efficient way of releasing energy, compared to alternative fermentation processes such as anaerobic glycolysis. During oxidative phosphorylation, electrons are transferred from electron donors to electron acceptors such as oxygen, in redox reactions. These redox reactions release energy, which is used to form ATP. These redox reactions are carried out by a series of protein complexes within the inner membrane of the cell's mitochondria. These linked sets of proteins are called electron transport chains. The energy released by electrons flowing through this electron transport chain is used to transport protons across the inner mitochondrial membrane, in a process called electron transport.

The term "proliferation" as used herein, means to grow or multiply by producing new cells.

The term "serum free media" as used herein, refers to cell culture media that does not require serum supplementation for cell expansion. "Low serum media" refers to cell culture media that may expand cells but contains a low percentage of serum supplementation (0.5-2% serum). For example, RPMI-1640 is a classical medium that requires 5-10% serum supplementation for cell expansion, while a low serum version of RPMI-1640 may also include polyamines, albumin, transferrin, insulin, and other components in addition to containing a lower concentration of serum.

A "subject" can be a vertebrate, a mammal, or a human. Mammals include, but are not limited to, farm animals, sport animals, pets, primates, mice and rats. In one aspect, a subject is a human. A "subject" can be a "patient" (e.g., under the care of a physician) but in some cases, a subject is not a patient.

A "co-stimulatory signal," as used herein, refers to a signal, which in combination with a primary signal, such as TCR/CD3 ligation, leads to T cell proliferation and/or activation and/or polarization.

"Separation," as used herein, includes any means of substantially purifying one component from another (e.g., by filtration, affinity, buoyant density, or magnetic attraction).

A "surface," as used herein, refers to any surface capable of having an agent attached thereto and includes, without limitation, metals, glass, plastics, co-polymers, colloids, lipids, cell surfaces, and the like. Essentially any surface that is capable of retaining an agent bound or attached thereto.

As used herein, the singular terms "a," "an," and "the" include the plural reference unless the context clearly indicates otherwise.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

II. Some Aspects of the Invention

In some aspects, the invention is based upon the activation and/or expansion of T cell populations using serum free media with galactose and glucose. Along these lines, it has been observed that T cell populations may be obtained and/or enhanced in a mixed population. T cells cultured and/or expanded using the compositions and methods of the present invention may have clinical applications directed to inflammation, autoimmunity, infection, and cancer. In some embodiments, T cells are cultured for use in adoptive transfer therapy.

Adoptive transfer of T cells re-directed to tumor-specific antigens by genetic engineering has shown great promise to treat, and in some cases cure, immune cell-based cancers. Infusion of up to $2 \times 10^7$ T cells/kg engineered to express a chimeric antigen receptor (CAR) linking a single chain antibody specific for human CD19 to a signaling complex comprised of the 4-1BB and CD3 zeta cytoplasmic domains was able to provide durable complete remissions to 90% patients suffering from relapsed or refractory acute B lymphoblastic leukemia (B-ALL) (Maude, S. L. et al. The New England Journal of Medicine 371, 1507-1517 (2014)). However, 24% of the patients were not able to receive this therapy because their T cells failed to expand adequately ex vivo and the target dose was not achieved, highlighting the difficulty of expanding T cells from cancer patients and the need to develop more efficient ways of expanding T cells for adoptive T cell therapy (Singh, N., et al. Science translational medicine 8 (2016)). One challenge prior to this invention concerns how to use serum to expand genetically engineered T cells. Human serum is expensive, requires infectious agent testing and potentially contains emerging infectious agents, varies considerably from lot to lot requiring frequent optimization and screening, contains agents harmful for T cell expansion and survival, and the current supply of human serum will not meet the demand if multiple T cell therapies become approved. A T cell manufacturing process that is not dependent on human serum would be an important step to make adoptive T cell therapy less expensive, more consistent, more efficacious, and available to more people.

The first serum free media (SFM) was developed in the 1960s. There is no consensus on the best media to use for adoptive T cell therapy; however, most groups to date have used RPMI, AIM V®, or X-Vivo™ 15. Both AIM V® and X-Vivo™ 15 are defined as SFM, but in the T cell manufacturing process used to treat patients, human serum is universally added, largely because patient derived T cells fail to grow optimally in serum free media and reduced efficacies of gene transfer resulting from T cell activation. As described herein, a serum free, or low serum, media was developed capable of expanding T cells.

One issue for consideration is characterization of mixtures containing population of T cells generated by methods of the invention. In many instances, compositions and methods for the invention will be directed to altering the ratio of glucose to galactose in media (e.g., serum free media). The ratio of glucose to galactose present in media (e.g., serum free media) may be from about 5:95 to about 95:5 (e.g., about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, or about 95:5 glucose:galactose). In some embodiments, the ratio of glucose to galactose present in serum free media is 50:50. Further, glucose:galactose ratio in media (e.g., serum free media) may be from about 10:90 to about 90:10, from about 20:80 to about 90:10, from about 30:70 to about 90:10, from about 40:60 to about 90:10, from about 10:90 to about 80:20, from about 10:90 to about 70:30, from about 10:90 to about 60:40, from about 20:80 to about 80:20, from about 30:70 to about 70:30, from about 40:60 to about 60:40, from about 45:55 to about 55:45, from about 47:53 to about 53:47, etc.

In some embodiments, the concentration of glucose: galactose in media (e.g., serum free media) is about 0.5 g/L glucose:5.5 g/L galactose to about 3.0 g/L glucose:3.0 g/L galactose (e.g., about 0.5 g/L glucose:5.5 g/L galactose, about 0.6 g/L glucose:5.4 g/L galactose, about 0.7 g/L glucose:5.3 g/L galactose, about 0.8 g/L glucose:5.2 g/L galactose, about 0.9 g/L glucose:5.1 g/L galactose, about 1.0 g/L glucose:5.0 g/L galactose, about 1.1 g/L glucose:4.9 g/L galactose, about 1.2 g/L glucose:4.8 g/L galactose, about 1.3 g/L glucose:4.7 g/L galactose, about 1.2 g/L glucose:4.8 g/L galactose, 1.3 g/L glucose:4.7 g/L galactose, about 1.6 g/L glucose:4.4 g/L galactose, about 1.5 g/L glucose:4.5 g/L galactose, about 1.6 g/L glucose:4.4 g/L galactose, about 1.7 g/L glucose:4.3 g/L galactose, about 1.8 g/L glucose:4.2 g/L galactose, about 1.9 g/L glucose:4.1 g/L galactose, about 2.0 g/L glucose:4.0 g/L galactose, about 2.1 g/L glucose:3.9 g/L galactose, about 2.2 g/L glucose:3.8 g/L galactose, about 2.3 g/L glucose:3.7 g/L galactose, about 2.4 g/L glucose:3.6 g/L galactose, about 2.5 g/L glucose:3.5 g/L galactose, about 2.6 g/L glucose:3.4 g/L galactose, about 2.7 g/L glucose:3.3 g/L galactose, 2.8 g/L glucose:3.2 g/L galactose, 2.9 g/L glucose: 3.1 g/L galactose, or about 3.0 g/L glucose:3.0 g/L galactose). Further, the concentration of glucose:galactose ratios in media (e.g., serum free media) may be from about 0.5 g/L glucose:5.5 g/L galactose to about 3.0 g/L glucose:3.0 g/L galactose, from about 1.0 g/L glucose:5.0 g/L galactose to about 3.0 g/L glucose:3.0 g/L galactose, from about 1.5 g/L glucose:4.5 g/L galactose to about 3.0 g/L glucose:3.0 g/L galactose, from about 2.0 g/L glucose:4.0 g/L galactose to about 3.0 g/L glucose:3.0 g/L galactose, from about 2.5 g/L glucose:3.5 g/L galactose to about 3.0 g/L glucose:3.0 g/L galactose, from about 3.5 g/L glucose:2.5 g/L galactose to about 5.5 g/L glucose:0.5 g/L galactose, from about 4.0 g/L glucose:2.0 g/L galactose to about 5.5 g/L glucose:0.5 g/L galactose, from about 4.5 g/L glucose:1.5 g/L galactose to about 5.5 g/L glucose:0.5 g/L galactose, from about 5.0 g/L glucose:1.0 g/L galactose to about 5.5 g/L glucose:0.5 g/L galactose, etc.

In some embodiments, the media is low serum media. In many instances, compositions and methods for the invention will be directed to altering the ratio of glucose to galactose in low serum media. The ratio of glucose to galactose present in low serum media may be from about 5:95 to about 95:5 (e.g., about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, or about 95:5 glucose:galactose). In some embodiments, the ratio of glucose to galactose present in low serum media is 50:50. Further, glucose:galactose ratio in low serum media may be from about 10:90 to about 90:10, from about 20:80 to about 90:10, from about 30:70 to about 90:10, from about 40:60 to about 90:10, from about 10:90 to about 80:20, from about 10:90 to about 70:30, from about 10:90 to about 60:40, from about 20:80 to about 80:20, from about 30:70 to about 70:30, from about 40:60 to about 60:40, from about 45:55 to about 55:45, from about 47:53 to about 53:47, etc.

In some embodiments, the concentration of glucose: galactose in low serum media is about 0.5 g/L glucose:5.5 g/L galactose to about 3.0 g/L glucose:3.0 g/L galactose (e.g., about 0.5 g/L glucose:5.5 g/L galactose, about 0.6 g/L glucose:5.4 g/L galactose, about 0.7 g/L glucose:5.3 g/L galactose, about 0.8 g/L glucose:5.2 g/L galactose, about 0.9 g/L glucose:5.1 g/L galactose, about 1.0 g/L glucose:5.0 g/L galactose, about 1.1 g/L glucose:4.9 g/L galactose, about 1.2 g/L glucose:4.8 g/L galactose, about 1.3 g/L glucose:4.7 g/L galactose, about 1.2 g/L glucose:4.8 g/L galactose, 1.3 g/L glucose:4.7 g/L galactose, about 1.6 g/L glucose:4.4 g/L galactose, about 1.5 g/L glucose:4.5 g/L galactose, about 1.6 g/L glucose:4.4 g/L galactose, about 1.7 g/L glucose:4.3 g/L galactose, about 1.8 g/L glucose:4.2 g/L galactose, about 1.9 g/L glucose:4.1 g/L galactose, about 2.0 g/L glucose:4.0 g/L galactose, about 2.1 g/L glucose:3.9 g/L galactose, about 2.2 g/L glucose:3.8 g/L galactose, about 2.3 g/L glucose:3.7 g/L galactose, about 2.4 g/L glucose:3.6 g/L galactose, about 2.5 g/L glucose:3.5 g/L galactose, about 2.6 g/L glucose:3.4 g/L galactose, about 2.7 g/L glucose:3.3 g/L galactose, 2.8 g/L glucose:3.2 g/L galactose, 2.9 g/L glucose:3.1 g/L galactose, or about 3.0 g/L glucose:3.0 g/L galactose). Further, the concentration of glucose:galactose ratios in low serum media may be from about 0.5 g/L glucose:5.5 g/L galactose to about 3.0 g/L glucose:3.0 g/L galactose, from about 1.0 g/L glucose:5.0 g/L galactose to about 3.0 g/L glucose:3.0 g/L galactose, from about 1.5 g/L glucose:4.5 g/L galactose to about 3.0 g/L glucose:3.0 g/L galactose, from about 2.0 g/L glucose:4.0 g/L galactose to about 3.0 g/L glucose:3.0 g/L galactose, from about 2.5 g/L glucose:3.5 g/L galactose to about 3.0 g/L glucose:3.0 g/L galactose, from about 3.5 g/L glucose:2.5 g/L galactose to about 5.5 g/L glucose:0.5 g/L galactose, from about 4.0 g/L glucose:2.0 g/L galactose to about 5.5 g/L glucose:0.5 g/L galactose, from about 4.5 g/L glucose:1.5 g/L galactose to about 5.5 g/L glucose:0.5 g/L galactose, from about 5.0 g/L glucose:1.0 g/L galactose to about 5.5 g/L glucose:0.5 g/L galactose, etc.

In many instances, compositions and methods of the invention will be directed to altering the ratio of T cells of particular subpopulations in a mixture. For example, methods of the invention may result in certain types of T cells being eliminated from a mixed population by, as examples, apoptosis or dilution. Thus, some aspects of the invention relate to the amount of enhancement or depletion of a T cell population in a mixture, as well as the mixtures themselves. For example, if there are two T cell subpopulations in a mixture (e.g., Th17 T cells and Th1 T cells) and these subpopulations are present in, for example, a 1:1 ratio, then the invention includes methods in which one T cell subpopulation is increased in proportion to the other T cell subpopulation. For purposes of illustration the ratio may be altered to from about 1:1.5 to about 1:100,000 (e.g., from about 1:1.5 to about 1:100,000, from about 1:1.5 to about 1:80,000, from about 1:1.5 to about 1:50,000, from about 1:1.5 to about 1:10,000, from about 1:1.5 to about 1:5,000, from about 1:2,500 to about 1:25,000, from about 1:2,500 to about 1:60,000, from about 1:2,500 to about 1:80,000, from about 1:2,500 to about 1:100,000, from about 1:5,000 to about 1:100,000, from about 1:5,000 to about 1:80,000, from about 1:5,000 to about 1:50,000, from about 1:5,000 to about 1:25,000, etc.).

In some embodiments, limited glucose:galactose media may be at least equal to limited glucose media for generating expanded T cells. T cells expanded in serum-free glucose/galactose media display a similar profile of cytokines with no impairment of IFNγ production when compared to control serum-supplemented media. T cells grown in media with equal parts glucose and galactose have superior cell culture performance compared to those grown in media with only glucose as a sugar source.

In some embodiments, combinations of glucose and galactose in serum free or low serum media are required for optimal T cell expansion. D-galactose alone is not sufficient to support optimal in vitro T cell expansion, while combinations of glucose and galactose at 30%, 50% and 70% expand T cells comparably to media with just glucose. Galactose is not metabolized by T cells; its presence in T cell culture medium provides a cell growth advantage that is not related to its catabolism. In some embodiments, lipids are the OXPHOS source of energy for T cells grown in galactose—containing serum-free medium and are required for optimal T cell expansion.

In some embodiments, serum free media with glucose: galactose and lipids (e.g., 1B2H media) supports the expansion of a more differentiated T cell phenotype. Naïve and memory cell subsets are the more favorable phenotype of T cells expanded in glucose/galactose medium as defined by greater frequencies at harvest versus control medium. The type of media used to expand naïve T cells does not influence the ability of a naïve T cell population to retain its naïve phenotype. However, T cells expanded in 1B2H (serum free media with glucose:galactose) maintain T cell effector cell phenotype better than T cells expanded in other serum free media (e.g., X-Vivo™ 15). In some embodiments, serum free media (e.g., 1B2H media) aids the ability of effector memory T cells to expand in culture and 1B2H also aids the ability of effector memory T cells to maintain their effector memory phenotype in culture. The ability of 1B2H to expand patient T cells equally well in the presence and absence of serum is linked to its ability to expand T cells with a highly differentiated phenotype. T cells expanded in serum-free glucose/galactose medium show a similar profile of cytokines with no impairment of IFNγ production when compared to control serum-supplemented media.

There is a high rate of expansion of naïve T cells in the presence of media (e.g., serum free media) with glucose, galactose and lipid supplementation. In some embodiments, naïve T cells expand by fold expansion, where 2 fold expansion refers to a doubling of the number of cells. T cell (e.g., naïve T cell) expansion may be in the ranges of from about 2 to about 200,000, from about 20 to about 200,000, from about 100 to about 200,000, from about 1,000 to about 200,000, from about 2,000 to about 200,000, from about 5,000 to about 200,000, from about 10,000 to about 200,000, from about 20,000 to about 200,000, from about 5,000 to about 125,000, from about 15,000 to about 125,000, from about 30,000 to about 125,000, from about 45,000 to about 100,000, from about 2,000 to about 80,000, etc.

In some embodiments, there is improved retention of CD8+ T cell subset in glucose/galactose serum-free medium. There is about 99% retention of CD8+ T cells post-expansion in glucose/galactose media (e.g., serum free media) when compared to the frequencies in control media (e.g., about 99.5%, about 99%, about 98.5%, about 98%, about 97.5%, about 97%, about 96.5%, about 96%, about 95.5%, about 95%, about 94.5%, about 94%, about 93.5%, about 93%, about 92.5%, about 92%, about 91.5%, about 91%, about 90.5%, about 90%, about 89.5%, about 89%, about 88.5%, about 88%, about 87.5%, about 87%, about 86.5%, about 86%, about 85.5%, about 85%, about 84.5%, about 84%, about 83.5%, about 83%, about 82.5%, about 82%, about 81.5%, about 81%, about 80.5%, or about 80%. Supplementation with serum is believed to have a slight negative effect on cell growth in glucose/galactose medium when compared to control media. This may also be seen as a reduction in T cell population doublings.

In some embodiments, the improved media formulation of 1B2H (serum free media), as described herein, generated improved CD19 CAR T cells compared to T cells grown in X-VIVO 15 media. Engineered T cells (e.g., chimeric antigen receptor T cells, or CART cells) may be cultured in the glucose:galactose media (e.g., serum free media) supplemented with lipids as described herein. CART 19 T cells cultured in the glucose:galactose serum free media have been found to be more potent than CART 19 T cells grown in serum free media without glucose:galactose.

Mammalian Immune System

The mammalian immune system uses two general adaptive mechanisms to protect the body against environmental pathogens. When a pathogen-derived molecule is encountered, the immune response is highly activated to ensure protection against that pathogenic organism.

The first mechanism is the non-specific (or innate) inflammatory response. The innate immune system can recognize specific molecules that are present on pathogens but not on the body itself. The second mechanism is the specific or acquired (or adaptive) immune response. Adaptive immune responses are custom tailored to the pathogen in question. The adaptive immune system evolves a specific immunoglobulin (antibody) response to many different molecules present in the pathogen, called antigens. In addition, a large repertoire of T cell receptors is sampled for their ability to bind processed forms of the antigens bound to MHC class I and II on antigen-presenting cells (APCs), such as dendritic cells (DCs).

The immune system recognizes and responds to structural differences between self and non-self proteins. Proteins that the immune system recognizes as non-self are referred to as antigens. Pathogens typically express large numbers of highly complex antigens. Acquired immunity has specific memory for antigenic structures; repeated exposure to the same antigen increases the response, which increases the level of induced protection against that particular pathogen.

Acquired immunity is mediated by specialized immune cells called B and T lymphocytes (or simply B and T cells). B cells produce and mediate their functions through the actions of antibodies. B cell-dependent immune responses are referred to as "humoral immunity," because antibodies are detected in body fluids. T cell-dependent immune responses are referred to as "cell mediated immunity," because effector activities are mediated directly by the local actions of effector T cells. The local actions of effector T cells are amplified through synergistic interactions between T cells and secondary effector cells, such as activated macrophages. The result is that the pathogen is killed and prevented from causing diseases.

Immune cells can require specific stimulation for activation. The use of anti-CD3/CD28, for example, provides the activation signal for some T cell population. T cells are believed to require at least two signals for activation. Signal one is antigen specific and is elicited by peptide/major histocompatibility complex (MHC) complexes presented by antigen-presenting cells (APC) and received through the T-cell receptor (TCR)/CD3 complex. For some T cell subpopulations, signal two can be delivered by antigen presenting cells and one of the candidate molecules for its receptor is the T cell antigen CD28. It is thought that when both the TCR/CD3 and CD28 T cell receptors are occupied by appropriate ligands, T cells are stimulated to proliferate and produce IL-2 (a cytokine essential for T cell proliferation), whereas occupation of the T cell receptor alone favors T cell anergy or apoptosis.

The present invention allows for one of skill to produce expanded T cell populations in a reliable, effective and efficient manner by culturing the T cells in serum free media with defined ratios of glucose:galactose as described herein. The expanded T cell populations may be used for different purposes, including but not limited to, therapeutic purposes and research/discovery purposes. As further described below, the T cell subpopulations include, but are not limited to, regulatory T cells, Th17 cells, Th9 cells, and antigen experienced memory cells.

Regulatory T Cells

Aspects of the present invention relate to methods for efficiently generating regulatory T cells (or "T regulatory cell" or "Treg") and the use of these methods in the generation of T cell populations which have applications in, for example, immunotherapy. Treg cells can be characterized by markers, such as CD4+,CD25+, FOXP3+, $CD127^{neg/low}$. In some instances, Treg cell expanded using compositions and methods of the invention will be CD4+, CD25+, FOXP3−. Compositions and methods for generating FOXP3− regulatory T cells are set out in Aarvak et al., U.S. Pat. No. 9,119,807.

Naturally occurring regulatory T (Treg) cells negatively regulate the activation of other T cells, including effector T cells, as well as innate immune system cells and can be utilized in immunotherapy against autoimmune diseases and provide transplantation tolerance. Various populations of Treg cells have been described and include naturally occurring CD4+CD25+FOXP3+ cells and induced Tr1 and Th3 cells that secrete IL-10 and TGF respectively.

Treg cells are characterized by sustained suppression of effector T cell responses. Traditional or conventional Treg cells can be found, e.g., in the spleen or the lymph node or in the circulation. Tregs are proven highly effective in preventing GVHD and autoimmunity in murine models. Clinical trials with adoptive transfer of Tregs in transplantation, treatment of diabetes and other indications are underway. The relative frequency of Tregs in peripheral blood is approximately 1-2% of total lymphocytes implicating the necessity of ex vivo expansion of Tregs prior to adoptive transfer for most clinical applications. Producing sufficient Tregs during the ex vivo expansion has been a major challenge in applying Treg therapy to humans.

Th17 Cells

T helper 17 cells (or "Th17 cells" or "Th17 helper cells") are an inflammatory subset of CD4+ T helper cells that regulate host defense, and are involved in tissue inflammation and various autoimmune diseases. Th17 cells have been found in various human tumors however their function in cancer immunity is unclear. When adoptively transferred into tumor-bearing mice, Th17 cells have been found to be more potent at eradicating melanoma than Th1 or non-polarized (Th0) T cells (Muranski et al. Blood. 2008). Th17 cells are developmentally distinct from Th1 and Th2 lineages. Th17 cells are CD4+ cells that are responsive to IL-1R1 and IL-23R signaling and produce the cytokines IL-17A, IL-17F, IL-17AF, IL-21, IL-22, IL-26 (human), GM-CSF, MIP-3a, and TNFα. The phenotype of Th17 cells is $CD3^+$, $CD4^+$, $CD17A^+$ and $CD17F^+$. One obstacle to the use of Th17 cells for adoptive cell transfer has been the identification of robust culture conditions that can expand the Th17 cell subset.

The invention relates, in part, to compositions and methods for the generation of T cell subtypes. One T cell subtype that may be produced using compositions and methods of the invention are Th17 cells.

Th9 Cells

T helper 9 cells (or "Th9 cells" or "Th9 helper cells") are an inflammatory subset of $CD4^+$ T helper cells that regulate host defense and are involved in allergy, inflammation and various autoimmune diseases. Th9 cells are identified by secretion of the signature cytokine IL-9. Although Th9 cells share some functional roles with Th2 cells, including promoting allergic inflammation and helminthic parasite immunity, Th9 cells can also promote autoimmunity in responses that are generally characterized as dependent on Th1 or Th17 cells. Th9 cells are differentiated under a cytokine environment containing both IL-4 and transforming growth factor β (TGFβ), which induce the transcriptional network required for the expression of IL-9. The Th9 subset is defined by its ability to produce large amounts of the signature cytokine IL-9. Transcription factors required for the development of Th9 cells include signal transducer and activator of transcription-6 (STAT6), interferon regulatory factor 4 (IRF4), B-cell activating transcription factor-like (BATF), GATA3, PU.1 and Smads. Th9 cells express high levels of IL-25 receptor (Il17rb), which is a potential surface maker to distinguish Th9 cells from other T helper subsets. Immune responses mediated by Th9 cells contribute to the protective immunity against intestinal parasite infection and to anti-tumor immunity.

The invention relates, in part, to compositions and methods for the generation of T cell subtypes. One T cell subtype that may be produced using compositions and methods of the invention are Th9 cells.

Memory T Cells

Memory T cells, or antigen-experienced cells, are experienced in a prior encounter with an antigen. These T cells are long-lived and can recognize antigens and quickly and strongly affect an immune response to an antigen to which they have been previously exposed. Memory T cells can encompass: stem memory cells ($T_{SCM}$), central memory cells ($T_{CM}$), effector memory cells (TEM). $T_{SCM}$ cells have the phenotype CD45RO−, CCR7+, CD45RA+, CD62L+(L-selectin), CD27+, CD28+ and IL-7Rα+, but they also express large amounts of IL-2Rβ, CXCR3, and LFA-1. $T_{CM}$ cells express L-selectin and the CCR7, they secrete IL-2, but not IFNγ or IL-4. TEM cells do not express L-selectin or CCR7 but produce effector cytokines like IFNγ and IL-4.

The present invention provides methods and compositions for the expansion of T cell populations. Prior methodologies do not allow one of skill in the art to expand T cells using the media described herein.

II. Methods of Producing T Cell Populations

Methods of the invention can be utilized to expand one or more T cell subpopulation(s). Exemplary T cell subpopulations include, but are not limited to, Treg cells, Th17 cells, Th9 cells, memory T cells, and engineered T cells (e.g., CAR T cells). Example uses for the expanded T cell subpopulations are disclosed herein.

Sources of Mixed Population of T Cells

The starting source for a mixed population of T cell can be blood (e.g., circulating blood) which may be isolated from a subject. Circulating blood can be obtained from one or more units of blood or from an apheresis or leukapheresis. The apheresis product typically contains lymphocytes, including T cells, monocytes, granulocytes, B cells, other nucleated white blood cells, red blood cells, and platelets. T cells can be obtained from a number of sources, including blood mononuclear cells, bone marrow, thymus, tissue biopsy, tumor, lymph node tissue, gut associated lymphoid tissue, mucosa associated lymphoid tissue, spleen tissue, or any other lymphoid tissue, and tumors. T cells can be obtained from T cell lines and from autologous or allogeneic sources. T cells may also be obtained from a xenogeneic source, for example, from mouse, rat, non-human primate, and pig.

In certain embodiments of the present invention, T cells can be obtained from a unit of blood collected from a subject using any number of techniques known to the skilled artisan, such as Ficoll separation. T cells may be isolated from the circulating blood of a subject. Blood may be obtained from the subject by apheresis or leukapheresis. The apheresis product typically contains lymphocytes, including T cells, monocytes, granulocytes, B cells, other nucleated white blood cells, red blood cells, and platelets. Prior to exposure to a sensitizing composition and subsequent activation and/or stimulation, a source of T cells is obtained from a subject. In some embodiments, the cells collected by apheresis may be washed to remove the plasma fraction and to place the cells in an appropriate buffer or media for subsequent processing steps. In some embodiments of the invention, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, Baxter) according to the manufacturer's instructions. After washing, the cells may be resuspended in a variety of biocompatible buffers, such as, for example, calcium (Ca)-free, magnesium (Mg)-free PBS. Alternatively, the undesirable components of the apheresis sample may be removed and the cells directly resuspended in culture media.

In other embodiments, T cells are isolated from peripheral blood lymphocytes by lysing or removing the red blood cells and depleting the monocytes, for example, by centrifugation through a PERCOLL™ gradient. A specific subpopulation of T cells, can be further isolated by positive or negative selection techniques.

In some embodiments, T cells can be positively selected for CD3+ cells. Any selection technique known to one of skill in the art may be used. One non-limiting example is flow cytometric sorting. In another embodiment, T cells can be isolated by incubation with anti-CD3 beads. One non-limiting example is anti-CD3/anti-CD28-conjugated beads, such as DYNABEADS® Human T-Expander CD3/CD28 (Life Technologies Corp., Cat. No. 11141D), for a time period sufficient for positive selection of the desired T cells. In a further embodiment, the time periods ranges from 30 minutes to 36 hours or longer and all integer values there between. In a further embodiment, the time period is at least 1, 2, 3, 4, 5, or 6 hours. In another embodiment the time period is 10 to 24 hours. In one embodiment, the incubation time period is 24 hours. Longer incubation times, such as 24 hours, can increase cell yield. Longer incubation times may be used to isolate T cells in any situation where there are few T cells as compared to other cell types. In one aspect of the present invention, enrichment of a T cell population by negative selection can be accomplished with a combination of antibodies directed to surface markers unique to the negatively selected cells. One possible method is cell sorting and/or selection via magnetic immunoadherence or flow cytometry that uses a cocktail of monoclonal antibodies direct to cell surface markers present on the cells negatively selected. In some embodiments, the fold expansion may differ based on the starting materials due to the variability of donor cells. In some embodiments, the normal starting density can be between about $0.5 \times 10^6$ to about $1.5 \times 10^6$.

Additionally, T cell subpopulations may be generated by selection on the basis of whether one or more marker(s) is/are present or absent. For example, Treg cells may be obtained from a mixed population based upon the selection of cells that are CD4+, CD25+, CD127neg/low and, optionally, FOXP3+. In some instances, Treg cells may be FOXP3-. Selection, in this instance, effectively refers to "choosing" of the cells based upon one or more definable characteristic. Further, selection can be positive or negative in that it can be for cells have one or more characteristic (positive) or for cells that do not have one or more characteristic (negative).

With respect to Treg cells, for purposes of illustration, these cells may be obtained from a mixed population through the binding of these cells to a surface (e.g., magnetic beads) having attached thereto antibodies that bind to CD4 and/or CD25 and the binding of non-Treg cells to a surface (e.g., magnetic beads) having attached thereto antibodies that binding CD127. As a specific example, magnetic beads having bound thereto an antibody that binds to CD3 may be used to isolate CD3+ cells. Once released, CD3+ cells obtained may then be contacted with magnetic beads having bound thereto an antibody that binds to CD4. The resulting CD3+, CD4+ cells may then be contacted with magnetic beads having bound thereto an antibody that binds to CD25. The resulting CD3+, CD4+, CD25+ cells may then be contacted with magnetic beads having bound thereto an antibody that binds to CD127, where the cells that are collected are those that do not bind to the beads.

In some instances, multiple characteristics may be used simultaneously to obtain a T cells subpopulation (e.g., Treg cells). For example, a surface containing bound thereto antibodies that bind to two or more cell surface marker may also be used. As a specific example, CD4+, CD25+ cells may be obtained from a mixed population through the binding of these cells to a surface having attached thereto antibodies that bind to CD4 and CD25. The selection for multiple characteristics simultaneously may result in number of undesired cells types "co-purifying" with the desired cell type(s). This is so because, using the specific example above, cells that are CD4+, CD25- and CD4-, CD25+ may be obtained in addition to CD4+, CD25+ cells.

Flow cytometry is particularly useful for the separation of cells based upon desired characteristics. Cells may be separated based upon detectable labels associated with molecules that bind to cells of interested (e.g., a natural ligand such as IL-7 binding to CD127, an antibody specific for CD25, etc.). Thus, ligands that bind to cellular components that may be detected and/or differentiated by flow cytometry systems may be used to purify/isolate T cells that have specific characteristics. Further, the presence or absence of multiple characteristics may be simultaneously determined by flow cytometry.

The invention thus includes methods for obtaining members of one or more T cell subpopulations, where members of the T cell subpopulations are identified by specific characteristics and separated from cells with differ with respect to these characteristics. Examples of characteristics that may be used in methods of the invention include the presence or absence of the following proteins CD3, CD4, CD5, CD8, CD11c, CD14, CD19, CD20, CD25, CD27, CD33, CD34, CD45, CD45RA, CD56, CD62L, CD123, CD127, CD278, CD335, CCR7, K562P, K562CD19, and FOXP3.

Expansion and/or Proliferation to Various T Cell Subpopulations

Mixed population of T cells isolated from a subject can be expanded into various T cell subpopulations by varying their exposure to a primary activation signal with a primary agent in addition to the culturing media described herein. The primary activation signal is anti-CD3 and can be achieved with a primary agent that is anti-CD3 (e.g., anti-CD3 antibody or other agent with binding specificity for CD3). The primary activation signal can be used in combination with second agent and/or a third agent, which can be directed to CD28, CD137, CD27, CD5, CD6, CD134, CD2, LFA-1, CD40, SLAM, GITR, and/or ICOS.

The cells of the invention can be expanded by incubation in culture with the agents as described above and herein. The compositions of the invention include serum free media with glucose and galactose and further supplementation of one or more lipids. In some embodiments, T cells are expanded when cultured in the serum free media described herein. T cells that are expanded include: Tregs, Th17, Th9, T central memory cells (Tcm), T effector memory cells (Tem), naïve T cells, and engineered T cells. The compositions of the invention also include low serum media with glucose and galactose and further supplementation of one or more lipids. In some embodiments, T cells are expanded when cultured in low serum media as described herein. T cells that are expanded include: Tregs, Th17, Th9, T central memory cells (Tcm), T effector memory cells (Tem), naïve T cells, and engineered T cells.

Chimeric Antigen Receptor T Cells (CAR T Cells)

Chimeric antigen receptors (CARs), (also known as Chimeric immunoreceptors, Chimeric T cell receptors, Artificial T cell receptors) are engineered receptors, which graft an arbitrary specificity onto an immune effector cell (T cell). These receptors are used to graft the specificity of a monoclonal antibody onto a T cell; with transfer of their coding sequence facilitated by retroviral vectors. The receptors are called chimeric because they are composed of parts from different sources. CARs may be used as a therapy for cancer through adoptive cell transfer. T cells are removed from a patient and modified so they express receptors specific to the patient's particular cancer. The T cells, which recognize and kill the cancer cells, are reintroduced into the patient. In some embodiments, modification of T-cells sourced from donors other than the patient may be used to treat the patient.

Using adoptive transfer of T cells expressing chimeric antigen receptors, CAR-modified T cells can be engineered to target any tumor-associated antigen. Following the collection of a patient's T cells, the cells are genetically engineered to express CARs specifically directed towards antigens on the patient's tumor cells before being infused back into the patient.

A method for engineering CAR T cells for cancer immunotherapy is to use viral vectors such as retrovirus, lentivirus or transposon, which integrate the transgene into the host cell genome. Alternatively, non-integrating vectors such as plasmids or mRNA may be used but these types of episomal DNA/RNA may be lost after repeated cell division. Consequently, the engineered CAR T cells may eventually lose their CAR expression. In another approach, a vector is used that is stably maintained in the T cell, without being integrated in its genome. This strategy has been found to enable long-term transgene expression without the risk of insertional mutagenesis or genotoxicity.

III. Compositions of the Invention

Compositions of the invention comprise media containing glucose and galactose. Compositions of the invention also comprise media containing glucose, galactose and, optionally, lipids in combinations capable of stimulating expansion of T cell populations. The invention further includes compositions comprising T cell populations present in culture media containing glucose and galactose. Such media may be free of human serum (e.g., serum free media) or contain low amounts of serum (e.g., low serum media).

Assays of interest include ELISA, RIA, flow cytometry, etc. Flow cytometry (fluorescence-activated cell sorting, or FACS) may be used to assess the stage of differentiation and/or phenotype of T cell populations during and/or post-culturing in the media of the present invention. Examples of markers used for FACS analysis include CD3, CD4, CD5, CD8, CD11c, CD14, CD19, CD20, CD25, CD27, CD33, CD34, CD45, CD45RA, CD56, CD62L, CD123, CD127, CD278, CD335, CCR7, K562P, K562CD19, and FOXP3.

In some embodiments, the ratio of glucose to galactose present in media (e.g., serum free media) may be from about 5:95 to about 95:5 (e.g., about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, or about 95:5 glucose:galactose). In some embodiments, the ratio of glucose to galactose present in serum free media is 50:50. Further, glucose:galactose ratio in media (e.g., serum free media) may be from about 10:90 to about 90:10, from about 20:80 to about 90:10, from about 30:70 to about 90:10, from about 40:60 to about 90:10, from about 10:90 to about 80:20, from about 10:90 to about 70:30, from about 10:90 to about 60:40, from about 20:80 to about 80:20, from about 30:70 to about 70:30, from about 40:60 to about 60:40, from about 45:55 to about 55:45, from about 47:53 to about 53:47, etc.

In some embodiments, the concentration of glucose:galactose in serum free media is about 0.5 g/L glucose:5.5 g/L galactose to about 3.0 g/L glucose:3.0 g/L galactose (e.g., about 0.5 g/L glucose:5.5 g/L galactose, about 0.6 g/L glucose:5.4 g/L galactose, about 0.7 g/L glucose:5.3 g/L galactose, about 0.8 g/L glucose:5.2 g/L galactose, about 0.9 g/L glucose:5.1 g/L galactose, about 1.0 g/L glucose:5.0 g/L galactose, about 1.1 g/L glucose:4.9 g/L galactose, about 1.2 g/L glucose:4.8 g/L galactose, about 1.3 g/L glucose:4.7 g/L galactose, about 1.2 g/L glucose:4.8 g/L galactose, 1.3 g/L glucose:4.7 g/L galactose, about 1.6 g/L glucose:4.4 g/L galactose, about 1.5 g/L glucose:4.5 g/L galactose, about 1.6 g/L glucose:4.4 g/L galactose, about 1.7 g/L glucose:4.3 g/L galactose, about 1.8 g/L glucose:4.2 g/L galactose, about 1.9 g/L glucose:4.1 g/L galactose, about 2.0 g/L glucose:4.0 g/L galactose, about 2.1 g/L glucose:3.9 g/L galactose, about 2.2 g/L glucose:3.8 g/L galactose, about 2.3 g/L glucose:3.7 g/L galactose, about 2.4 g/L glucose:3.6 g/L galactose, about 2.5 g/L glucose:3.5 g/L galactose, about 2.6 g/L glucose:3.4 g/L galactose, about 2.7 g/L glucose:3.3 g/L galactose, 2.8 g/L glucose:3.2 g/L galactose, 2.9 g/L glucose:3.1 g/L galactose, or about 3.0 g/L glucose:3.0 g/L galactose). Further, the concentration of glucose:galactose ratios in serum free media may be from about 0.5 g/L glucose:5.5 g/L galactose to about 3.0 g/L glucose:3.0 g/L galactose, from about 1.0 g/L glucose:5.0 g/L galactose to about 3.0 g/L glucose:3.0 g/L galactose, from about 1.5 g/L glucose:4.5 g/L galactose to about 3.0 g/L glucose:3.0 g/L galactose, from about 2.0 g/L glucose:4.0 g/L galactose to about 3.0 g/L glucose:3.0 g/L galactose, from about 2.5 g/L glucose:3.5 g/L galactose to about 3.0 g/L glucose:3.0 g/L galactose, from about 3.5 g/L glucose:2.5 g/L galactose to about 5.5 g/L glucose:0.5 g/L galactose, from about 4.0 g/L glucose:2.0 g/L galactose to about 5.5 g/L glucose:0.5 g/L galactose, from about 4.5 g/L glucose:1.5 g/L galactose to about 5.5 g/L glucose:0.5 g/L galactose, from about 5.0 g/L glucose:1.0 g/L galactose to about 5.5 g/L glucose:0.5 g/L galactose, etc.

In some embodiments, the media is low serum media. In many instances, compositions and methods for the invention will be directed to altering the ratio of glucose to galactose in low serum media. The ratio of glucose to galactose present in low serum media may be from about 5:95 to about 95:5 (e.g., about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, or about 95:5 glucose:galactose). In some embodiments, the ratio of glucose to galactose present in low serum media is 50:50.

In some embodiments, the concentration of glucose:galactose in low serum media is about 0.5 g/L glucose:5.5 g/L galactose to about 3.0 g/L glucose:3.0 g/L galactose (e.g., about 0.5 g/L glucose:5.5 g/L galactose, about 0.6 g/L glucose:5.4 g/L galactose, about 0.7 g/L glucose:5.3 g/L galactose, about 0.8 g/L glucose:5.2 g/L galactose, about 0.9 g/L glucose:5.1 g/L galactose, about 1.0 g/L glucose:5.0 g/L galactose, about 1.1 g/L glucose:4.9 g/L galactose, about 1.2 g/L glucose:4.8 g/L galactose, about 1.3 g/L glucose:4.7 g/L galactose, about 1.2 g/L glucose:4.8 g/L galactose, 1.3 g/L glucose:4.7 g/L galactose, about 1.6 g/L glucose:4.4 g/L galactose, about 1.5 g/L glucose:4.5 g/L galactose, about 1.6 g/L glucose:4.4 g/L galactose, about 1.7 g/L glucose:4.3 g/L galactose, about 1.8 g/L glucose:4.2 g/L galactose, about 1.9 g/L glucose:4.1 g/L galactose, about 2.0 g/L glucose:4.0 g/L galactose, about 2.1 g/L glucose:3.9 g/L galactose, about 2.2 g/L glucose:3.8 g/L galactose, about 2.3 g/L glucose:3.7 g/L galactose, about 2.4 g/L glucose:3.6 g/L galactose, about 2.5 g/L glucose:3.5 g/L galactose, about 2.6 g/L glucose:3.4 g/L galactose, about 2.7 g/L glucose:3.3 g/L galactose, 2.8 g/L glucose:3.2 g/L galactose, 2.9 g/L glucose:3.1 g/L galactose, or about 3.0 g/L glucose:3.0 g/L galactose). Further, the concentration of glucose:galactose ratios in low serum media may be from about 0.5 g/L glucose:5.5 g/L galactose to about 3.0 g/L glucose:3.0 g/L galactose, from about 1.0 g/L glucose:5.0 g/L galactose to about 3.0 g/L glucose:3.0 g/L galactose, from about 1.5 g/L glucose:4.5 g/L galactose to about 3.0 g/L glucose:3.0 g/L galactose, from about 2.0 g/L glucose:4.0 g/L galactose to about 3.0 g/L glucose:3.0 g/L galactose, from about 2.5 g/L glucose:3.5 g/L galactose to about 3.0 g/L glucose:3.0 g/L galactose, from about 3.5 g/L glucose:2.5 g/L galactose to about 5.5 g/L glucose:0.5 g/L galactose, from about 4.0 g/L glucose:2.0 g/L galactose to about 5.5 g/L glucose:0.5 g/L galactose, from about 4.5 g/L glucose:1.5 g/L galactose to about 5.5 g/L glucose:0.5 g/L galactose, from about 5.0 g/L glucose:1.0 g/L galactose to about 5.5 g/L glucose:0.5 g/L galactose, etc.

In some embodiments, the compositions of the present invention comprise lipids. T cells are expanded in media (e.g., serum free media) containing lipids. Lipids may include fatty acids. Media (e.g., serum free media) used to culture T cells contains lipids selected from: fatty acids, long chain fatty acid, short chain fatty acids, medium chain fatty acids, very long chain fatty acids, saturated fatty acids, and unsaturated fatty acids. Lipids present in the media (e.g., serum free media) may include: cholesterol, arachidonic acid, arachidic acid, linoleic acid, linolenic acid, myristic acid, myristoleic acid, erucic acid, oleic acid, sapienic acid, elaidic acid, vaccenic acid, linoelaidic acid, eicosapentaenoic acid, docosahexaenoic acid, palmitic acid, palmitoleic acid, palmoleic acid, behenic acid, cerotic acid, lignoceric acid, caprylic acid, capric acid, lauric acid, and/or stearic acid.

Media (e.g., low serum media) used to culture T cells contains lipids selected from: fatty acids, long chain fatty acid, short chain fatty acids, medium chain fatty acids, very long chain fatty acids, saturated fatty acids, and unsaturated fatty acids. Lipids present in the low serum media may include: cholesterol, arachidonic acid, arachidic acid, linoleic acid, linolenic acid, myristic acid, myristoleic acid, erucic acid, oleic acid, sapienic acid, elaidic acid, vaccenic acid, linoelaidic acid, eicosapentaenoic acid, docosahexaenoic acid, palmitic acid, palmitoleic acid, palmoleic acid, behenic acid, cerotic acid, lignoceric acid, caprylic acid, capric acid, lauric acid, and/or stearic acid.

In some embodiments, compositions of the present invention comprise lipid to media ratios from about 1:10 to about 1:1,000,000 (e.g., about 1:10, about 1:20, about 1:30, about 1:50, about 1:100, about 1:200, about 1:250, about 1:500, about 1:750, about 1:1000, about 1:2000, about 1:5000, about 1:10,000, about 1:20,000, about 1:50,000, about 1:100,000, about 1:200,000, about 1:500,000, or about 1:1,000,000). Further, lipid to media ratios may be from about 1:10 to about 1:1,000,000, from about 1:20 to 1:1,000,000, from about 1:30 to about 1:1,000,000, from about 1:50 to about 1:1,000,000, from about 1:100 to about 1:1,000,000, from about 1:200 to about 1:1,000,000, from about 1:250 to about 1:1,000,000, from 1:300 to about 1:1,000,000, from about 1:500 to about 1:1,000,000, from 1:750 to about 1:1,000,000, from about 1:1000 to about 1:1,000,000, from about 1:2000 to about 1:1,000,000, from about 1:5000 to about 1:1,000,000, from about 1:10,000 to about 1:1,000,000, from about 1:20,000 to about 1:1,000,000, from 1:50,000 to about 1:1,000,000, from 1:100,000 to about 1:1,000,000, from about 1:200,000 to about 1:1,000,000, from about 1:500,000 to about 1:1,000,000.

In some embodiments, compositions of the present invention comprise total lipids present in media (e.g., serum free media) from about 0.000005 mol/L to about 0.01 mol/L (e.g., about 0.000005 mol/L, about 0.00001 mol/L, about 0.00005 mol/L, about 0.0001 mol/L, about 0.0005 mol/L, about 0.001 mol/L, about 0.005 mol/L, or about 0.01 mol/L). In some embodiments, compositions of the present invention comprise cholesterol present in media (e.g., serum free media) from about 0.000005 mol/L to about 0.01 mol/L (e.g., about 0.000005 mol/L, about 0.00001 mol/L, about 0.00005 mol/L, about 0.0001 mol/L, about 0.0005 mol/L, about 0.001 mol/L, about 0.005 mol/L, or about 0.01 mol/L). In some embodiments, compositions of the present invention comprise fatty acids present in media (e.g., serum free media) from about 0.000005 mol/L to about 0.01 mol/L (e.g., about 0.000005 mol/L, about 0.00001 mol/L, about 0.00005 mol/L, about 0.0001 mol/L, about 0.0005 mol/L, about 0.001 mol/L, about 0.005 mol/L, or about 0.01 mol/L).

In some embodiments, compositions of the present invention comprise total lipids present in media (e.g., serum free media) from about 0.001 g/L to about 1.0 g/L (e.g., about 0.001 g/L, about 0.005 g/L, about 0.01 g/L, about 0.05 g/L, about 0.1 g/L, about 0.5 g/L, about 0.7 g/L, or about 1.0 g/L). In some embodiments, compositions of the present invention comprise total cholesterol present in media (e.g., serum free media) from about 0.001 g/L to about 1.0 g/L (e.g., about 0.001 g/L, about 0.005 g/L, about 0.01 g/L, about 0.05 g/L, about 0.1 g/L, about 0.5 g/L, about 0.7 g/L, or about 1.0 g/L). In some embodiments, compositions of the present invention comprise total fatty acids present in serum free media from about 0.001 g/L to about 1.0 g/L (e.g., about 0.001 g/L, about 0.005 g/L, about 0.01 g/L, about 0.05 g/L, about 0.1 g/L, about 0.5 g/L, about 0.7 g/L, or about 1.0 g/L).

In some embodiments, compositions of the present invention comprise total lipids present in low serum media from about 0.000005 mol/L to about 0.01 mol/L (e.g., about 0.000005 mol/L, about 0.00001 mol/L, about 0.00005 mol/L, about 0.0001 mol/L, about 0.0005 mol/L, about 0.001 mol/L, about 0.005 mol/L, or about 0.01 mol/L). In some embodiments, compositions of the present invention comprise cholesterol present in low serum media from about 0.000005 mol/L to about 0.01 mol/L (e.g., about 0.000005 mol/L, about 0.00001 mol/L, about 0.00005 mol/L, about 0.0001 mol/L, about 0.0005 mol/L, about 0.001 mol/L, about 0.005 mol/L, or about 0.01 mol/L). In some embodiments, compositions of the present invention comprise fatty acids present in low serum media from about 0.000005 mol/L to about 0.01 mol/L (e.g., about 0.000005 mol/L, about 0.00001 mol/L, about 0.00005 mol/L, about 0.0001 mol/L, about 0.0005 mol/L, about 0.001 mol/L, about 0.005 mol/L, or about 0.01 mol/L).

In some embodiments, compositions of the present invention comprise total lipids present in low serum media from about 0.001 g/L to about 1.0 g/L (e.g., about 0.001 g/L, about 0.005 g/L, about 0.01 g/L, about 0.05 g/L, about 0.1 g/L, about 0.5 g/L, about 0.7 g/L, or about 1.0 g/L). In some embodiments, compositions of the present invention comprise total cholesterol present in low serum media from about 0.001 g/L to about 1.0 g/L (e.g., about 0.001 g/L, about 0.005 g/L, about 0.01 g/L, about 0.05 g/L, about 0.1 g/L, about 0.5 g/L, about 0.7 g/L, or about 1.0 g/L). In some embodiments, compositions of the present invention comprise total fatty acids present in low serum media from about 0.001 g/L to about 1.0 g/L (e.g., about 0.001 g/L, about 0.005 g/L, about 0.01 g/L, about 0.05 g/L, about 0.1 g/L, about 0.5 g/L, about 0.7 g/L, or about 1.0 g/L).

IV. Methods of Using the Invention

T cell subpopulations of the invention can be used in any number of physiological conditions, diseases and/or disease states for therapeutic purposes and/or research/discovery purposes. Condition or disease typified by an aberrant immune response may be an autoimmune disease, for example diabetes, multiple sclerosis, myasthenia gravis, neuritis, lupus, rheumatoid arthritis, psoriasis or inflammatory bowel disease. Conditions in which immune suppression would be advantageous include conditions in which a normal or an activated immune response is disadvantageous to the mammal, e.g., allo-transplantation of, e.g., body fluids or parts, to avoid rejection, or in fertility treatments in which inappropriate immune responses have been implicated in failure to conceive and miscarriage. The use of such cells before, during, or after transplantation avoids extensive chronic graft versus host disease which may occur in patients being treated (e.g., cancer patients). The cells may be expanded immediately after harvest or stored (e.g., by freezing) prior to expansion or after expansion and prior to their therapeutic use. Such therapies may be conducted in conjunction with known immune suppressive therapies.

In some embodiments, T cells are isolated based upon the stage of differentiation. T cell populations may be assessed for the stage of differentiation based upon the presence or absence of certain cellular markers or proteins. Markers used to assess the stage of T cell differentiation include: CD3, CD4, CD5, CD8, CD11c, CD14, CD19, CD20, CD25, CD27, CD33, CD34, CD45, CD45RA, CD45RB, CD56, CD62L, CD123, CD127, CD278, CD335, CCR7, and FOXP3.

Once an appropriate T cell population or sub population has been isolated from a patient or animal, genetic or any other appropriate modification or manipulation may optionally be carried out before the resulting T cell population is expanded using the methods and supports of the invention. The manipulation may, for example, take the form of stimulate/re-stimulation of the T cells with anti-CD3 and anti-CD28 antibodies to activate/re-activate them.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 ml to 400 ml. In certain embodiments, T cells are activated from blood draws of about 20 ml, about 30 ml, about 40 ml, about 50 ml, about 60 ml, about 70 ml, about 80 ml, about 90 ml, or about 100 ml. The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention may be administered by i.v. injection. The compositions of T cells may be injected directly into a tumor, lymph node, or site of infection/inflammation (autoimmunity).

Compositions of T cell subpopulation generated according to the invention have many potential uses, including experimental and therapeutic uses. In particular it is envisaged that such T cell populations will be extremely useful in suppressing undesirable or inappropriate immune responses. In such methods a small number of T cells are removed from a patient and then manipulated and expanded ex vivo before reinfusing them into the patient. Examples of diseases which may be treated in this way are autoimmune diseases and conditions in which suppressed immune activity is desirable (e.g., for allo-transplantation tolerance). A therapeutic method could comprise providing a mammal, obtaining a biological sample from the mammal that contains T cells; expanding/activating the T cells ex vivo in accordance with the methods of the invention as described above; and administering the expanded/activated T cells to the mammal to be treated. The first mammal and the mammal to be treated can be the same or different. The mammal can generally be any mammal, such as cats, dogs, rabbits, horses, pigs, cows, goats, sheep, monkeys, or humans. The first mammal ("donor") can be syngeneic, allogeneic, or xenogeneic. Therapy could be administered to mammals having aberrant immune response (such as autoimmune diseases including, for example diabetes, multiple sclerosis, myasthenia gravis, neuritis, lupus, rheumatoid arthritis, psoriasis, and inflammatory bowel disease), tissue transplantation, or fertility treatments.

The main technical hurdles involved in such therapies include the purification of the cells of interest from the patient and the expansion and/or the manipulation of the cells in vitro. Such therapies generally require a large number of cells and thus it can be seen that it is vital to optimize the methods of inducing in vitro T cell proliferation in order to maximize the number of T cells produced and minimize the time required to produce the T cells in sufficient numbers. The compositions and methods of the present invention provide large numbers of T cells of specific subpopulations.

T cell subpopulations of the present invention can be used in a variety of applications and treatment modalities. T cell subpopulations of the present invention can be used in the treatment of disease states including, but not limited to, cancer, autoimmune disease, allergic diseases, inflammatory diseases, infectious diseases, and graft versus host disease (GVHD). Broad example T cell therapies include infusion to a subject of T cell subpopulations externally expanded by methods of the present invention following or not following immune depletion, or infusion to a subject of heterologous externally expanded T cells that have been isolated from a donor subject (e.g., adoptive cell transfer).

Autoimmune Disorders

Autoimmune diseases or disorders are those diseases that result from an inappropriate and excessive response to a self-antigen. Studies have implicated defective Treg cells in autoimmune disorders. Autoimmune diseases include: diabetes mellitus, uveoretinitis and multiple sclerosis, Addison's disease, celiac disease, dermatomyositis, Grave's disease, Hashimoto's thyroiditis, alopecia areata, ankylosing spondylitis, autoimmune hepatitis, autoimmune parotitis, hemolytic anemia, pemphigus vulgaris, psoriasis, rheumatic fever, sarcoidosis, scleroderma, spondyloarthropathies, vasculitis, vitiligo, myxedema, pernicious anemia, ulcerative colitis, Crohn's disease, dystrophic epidermolysis bullosa, epididymitis, glomerulonephritis, Graves' disease, Guillain-Barre syndrome, Myasthenia gravis, pernicious anemia, reactive arthritis, rheumatoid arthritis, Sjogren's syndrome, and systemic lupus erthematosus as none limiting examples. In autoimmune disease states, the $CD4^+CD25^+$ T regs may be present in decreased number or be functionally deficient. Tregs from peripheral blood having reduced capacity to suppress T-cell proliferation have been found in patients with multiple sclerosis (Viglietta et al., *J. Exp. Med.* 199: 971-979 (2004).), autoimmune polyglandular syndrome type II (Kriegel et al., *J. Exp. Med.* 199:1285-1291 (2004).), type I diabetes (Lindley et al. *Diabetes* 54:92-929 (2005).), psoriasis (Sugiyama et al., *J. Immunol.* 174:164-173 (2005)), and myasthenia gravis (Balandina et al., *Blood* 105:735-741 (2005)).

Treatment of autoimmune disorders with T cell therapy may involve differing mechanisms. In one embodiment, blood or another source of immune cells can be removed from a subject inflicted with an autoimmune disorder. Methods of the invention discussed herein can be used to expand T cell types other than memory T cells from the patient sample. Following removal and expansion of autologous cells, inappropriate memory T cells can be depleted within a subject in need thereof by known methods, including low dose total body radiation, thymic irradiation, antithymocyte globulin, and administration of chemotherapy. Illustrative chemotherapeutic agents of the present invention include but are not limited to campath, anti-CD3 antibodies, cytoxin, fludarabine, cyclosporine, FK506, mycophenolic acid, steroids, FR901228, and irradiation. Following depletion of the inappropriate memory T cells which are capable of recognizing self-antigens, the externally expanded autologous T cells can be readministered to the subject to reconstitute or restimulate their immune system.

Alternatively, or in addition to the above described treatment modalities, Treg cells can be isolated from sources including peripheral blood mononuclear cells, bone marrow, thymus, tissue biopsy, tumor, lymph node tissue, gut associated lymphoid tissue, mucosa associated lymphoid tissue, spleen tissue, or any other lymphoid tissue, and tumors. These T cells can be expanded using methods of the invention. These expanded Treg cells can be re-administered to a patient to suppress inappropriate immune responses. This Treg therapy may be administered either to suppress the minimal remaining immune responses following immune depletion, or in subjects that have not undergone immune depletion.

Graft Versus Host Disease

A major problem in hematopoietic stem cell transplantation is GVHD, which is caused by alloreactive T cells present in the infused hematopoietic stem cell preparation. In organ transplantation, graft rejection mediated by alloreactive host T cells is the major problem, usually overcome by long-term immunosuppression of the transplant recipient.

In methods similar to those described above, treating, reducing the risk of, or the severity of, an adverse GVHD event with T cell therapy may involve differing mechanisms. In one embodiment, blood or another source of immune cells can be removed from a subject inflicted with GVHD. Methods of the invention discussed herein can be used to selectively expand T cell types other than memory T cells, selectively expanding those cell types that do not comprise long-lasting recognition of antigens from the exogenous tissue. Following removal and external expansion of autologous cells, inappropriate memory T cells can be depleted within a subject in need thereof by known methods, including low dose total body radiation, thymic irradiation, antithymocyte globulin, and administration of chemotherapy. Illustrative chemotherapeutic agents of the present invention include but are not limited to campath, anti-CD3 antibodies, cytoxin, fludarabine, cyclosporine, FK506, mycophenolic acid, steroids, FR901228, and irradiation. Following depletion of the inappropriate memory T cells capable of recognizing antigens on the exogenous tissues, the externally expanded autologous T cells can be readministered to the subject to reconstitute or restimulate their immune system.

Alternatively, or in addition to the above described treatment modalities, Treg cells removed from patient blood can be expanded. These expanded Treg cells can be readministered to a patient to suppress inappropriate immune responses, either to suppress the minimal remaining immune responses following immune depletion, or in subjects that have not undergone immune depletion.

Allergic Diseases

Allergic diseases may also be affected by T cell dysfunction. Studies have indicated impaired $CD4^+CD25^+$ Treg-mediated inhibition of allergen-specific T helper type 2 (Th2) are present in patients suffering seasonal allergies (Ling E M, et al., Lancet 2004; 363:608-15; Grindebacke H, et al., Clin Exp Allergy 2004; 34:1364-72.). Furthermore, altered proportions of T cells populations have been implicated in individuals with allergies and asthmatic diseases compared to healthy subjects (Akdis M, et al., J Exp Med 2004; 199:1567-75; Tiemessen M M, et al., J Allergy Clin Immunol 2004; 113:932-9.).

In methods similar to those described above, treatment, prevention, or alleviation of allergic diseases with T cell therapy may involve differing mechanisms. Similar to autoimmune disorders and GVHD, allergic diseases are caused by an inappropriate immune response. Suppression of that response, or depletion of cells capable of recognizing the inappropriate antigen may alleviate the allergic symptoms. In methods of T cell therapy for the treatment of allergies, blood can be removed from a subject suffering from an allergic disorder. Methods of the invention discussed herein can be used to selectively expand non T memory cell T cell types, selectively expanding those cell types that do not comprise long-lasting recognition of antigens from the inappropriate antigen (e.g., a legume protein). Following removal and expansion of autologous cells, inappropriate memory T cells can be depleted within a subject in need thereof by known methods, including low dose total body radiation, thymic irradiation, antithymocyte globulin, and administration of chemotherapy. Illustrative chemotherapeutic agents of the present invention include but are not limited to campath, anti-CD3 antibodies, cytoxin, fludarabine, cyclosporine, FK506, mycophenolic acid, steroids, FR901228, and irradiation. Following depletion of the inappropriate memory T cells capable of recognizing antigens on the exogenous tissues, the externally expanded autologous T cells can be readministered to the subject to reconstitute or restimulate their immune system.

Alternatively, or in addition to the above described treatment modalities, Treg cells removed from patient blood can be expanded. These expanded Treg cells can be readministered to a patient to suppress inappropriate immune responses, either to suppress the minimal remaining immune responses following immune depletion, or in subjects that have not undergone immune depletion.

Inflammatory Diseases

T cell therapy has been implicated in the treatment of inflammatory diseases and inflammation associated disorders. Many of these diseases can also be categorized as autoimmune disorders. Non-limiting examples of inflammatory diseases and inflammation associated disorders include: diabetes; rheumatoid arthritis; inflammatory bowel disease; familial mediterranean fever; neonatal onset multisystem inflammatory disease; tumor necrosis factor (TNF) receptor-associated periodic syndrome (TRAPS); deficiency of interleukin-1 receptor antagonist (DIRA); and Behcet's disease.

Because of the role of Treg cells in suppressing inappropriate immune responses to non pathogenic antigens, decreased numbers or impaired functioning of these T cell subpopulations can contribute to inflammatory diseases. This is true of, for example, inflammatory bowel disease (M Himmell, et al., Immunology 2012 June; 136(2): 115-122) and rheumatoid arthritis (M Noack, et al., Autoimmunity Reviews 2014 June; 13(6): 668-677).

Inflammatory diseases are mechanistically similar to autoimmune disorders. As such, inflammatory diseases can be caused in part by an inappropriate immune response. Suppression of that response, or depletion of cells capable of recognizing the inappropriate antigen may alleviate the inflammatory symptoms. In methods of T cell therapy for the treatment of inflammatory diseases, blood can be removed from a subject suffering from an inflammatory disorder. Methods of the invention discussed herein can be used to selectively expand non T memory cell T cell types, selectively expanding those cell types that do not comprise long-lasting recognition of inappropriate antigens (e.g., carbamylated proteins in anticarbamylated protein (anti-CarP) antibody mediated rheumatoid arthritis). Following removal and expansion of autologous cells, inappropriate memory T cells can be depleted within a subject in need thereof by known methods, including low dose total body radiation, thymic irradiation, antithymocyte globulin, and administration of chemotherapy. Illustrative chemotherapeutic agents of the present invention include but are not limited to campath, anti-CD3 antibodies, cytoxin, fludarabine, cyclosporine, FK506, mycophenolic acrid, steroids. FR901228, and irradiation. Following depletion of the inappropriate memory T cells capable of recognizing self-antigens and mounting the resultant inflammatory response, the externally expanded autologous T cells can be readministered to the subject to reconstitute their immune system.

Alternatively, or in addition to the above described treatment modalities, Treg cells removed from patient blood can be expanded. These expanded Treg cells can be readministered to a patient to suppress inappropriate immune responses, either to suppress the minimal remaining immune responses following immune depletion, or in subjects that have not undergone immune depletion.

Hyperproliferative Disorders

Evidence from cancer patients has further implicated T cell dysfunction with hyperproliferative disorders, including cancer. For example, increased Treg activity may result in poor immune response to tumor antigens and contribute to immune dysfunction. Elevated populations of CD4+CD25+ have been found in lung, pancreatic, breast, liver and skin cancer patients, in either the blood or tumor itself (Woo E Y, et al.; J Immunol 2002; 168:4272-6; Wolf A M, et al. Clin Cancer Res 2003; 9:606-12; Liyanage U K, et al. J Immunol 2002; 169:2756-61; Viguier M, et al. J Immunol 2004; 173:1444-53; Ormandy L A, et al. Cancer Res 2005; 65:2457-64).

Using the methods of the invention T cells specific for tumor antigens or hyperproliferative disorder antigens or antigens associate with a hyperproliferative disorder can be expanded. Tumor antigens are proteins that are produced by tumor cells that elicit an immune response, particularly T-cell mediate immune responses.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated by products of the invention include but are not limited to carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included. Among these are cancers including skin cancer, brain cancer and other central nervous system cancers, head cancer, neck cancer, muscle/sarcoma cancer, bone cancer, lung cancer, esophagus cancer, stomach cancer, pancreas cancer, colon cancer, rectum cancer, uterus cancer, cervix cancer, vagina cancer, vulva cancer, penis cancer, breast cancer, kidney cancer, prostate cancer, bladder cancer, or thyroid cancer or glioblastoma.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia, and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia, and myelodysplasia.

Solid tumors are abnormal masses that usually do not contain cysts or liquid areas. Solid tumors can be benign or malignant. Different types of solid tumors are named for the types of cells that form them (such as sarcomas, carcinomas, and lymphomas). Examples of solid tumors such as sarcomas and carcinoma, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

One approach to treating subjects in need thereof or patients is to use the expanded T cells of the invention and genetically modify the T cells to target antigens expressed on tumor cells through the expression of chimeric antigen receptors (CARs). CARs are antigen receptors that are designed to recognize cell surface antigens in a human leukocyte antigen independent manner. In treatment utilizing CARs immune cells may be collected from patient blood or other tissue. The T cells are engineered as described below to express CARs on their surface, allowing them to recognize specific antigens (e.g., tumor antigens). These CAR T cells can then be expanded by methods of the present invention and infused into the patient. In certain embodiments, T cells are administered at $1\times10^5$, $1\times10^6$, $1\times10^7$, $1\times10^8$, $5\times10^8$, $1\times10^9$, $5\times10^9$, $1\times10^{10}$, $5\times10^{10}$, $1\times10^{11}$, $5\times10^{11}$, or $1\times10^{12}$ cells to the subject. Following patient infusion, the T cells will continue to expand and express the CAR, allowing for the mounting of an immune response against cells harboring the specific antigen the CAR is engineered to recognize.

In one embodiment, the invention provides a cell (e.g., a T cell) engineered to express a CAR wherein the CAR T cell exhibits an antitumor property. The CAR of the invention can be engineered to comprise an extracellular domain having an antigen binding domain fused to an intracellular signaling domain of the T cell antigen receptor complex zeta chain (e.g., CD3 zeta). The CAR, when expressed in a T cell is able to redirect antigen recognition based on the antigen binding specificity.

The antigen binding moiety of the CAR comprises a target-specific binding element otherwise referred to as an antigen binding moiety. The choice of moiety depends on the type and number of ligands that define the surface of a target cell. For example, the antigen binding domain may be chosen to recognize a ligand that acts as a cell surface marker on target cells associated with a particular disease state. Thus the antigen moiety domain in the CAR of the invention includes those associated with viral, bacterial and parasitic infections, autoimmune disease and cancer cells.

The expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The T cells of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements (e.g., enhancers) regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Methods of making CAR T cells are known in the art (see, e.g., U.S. Pat. No. 8,906,682).

In an embodiment where a T cell is a CAR T cell, the selection of the antigen binding moiety of the invention will depend on the particular type of cancer to be treated. Tumor antigens are known in the art and include, for example, a glioma-associated antigen, carcinoembryonic antigen (CEA), (3-human chorionic gonadotropin, alphafetoprotein (AFP), lectin-reactive AFP, thyroglobulin, RAGE-1, MN-CA IX, human telomerase reverse transcriptase, RUL RU2 (AS), intestinal carboxyl esterase, mut hsp70-2, M-CSF, prostase, prostate-specific antigen (PSA), PAP, NY-ESO-1, LAGE-1a, p53, prostein, PSMA, HER2/neu, surviving and telomerase, prostate-carcinoma tumor antigen-1 (PCTA-1), MAGE, ELF2M, neutrophil elastase, ephrin B2, CD22, insulin growth factor (IGF-1), IGF-II, IGF-I receptor and mesothelin.

In one embodiment, the tumor antigen comprises one or more antigenic cancer epitopes associate with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecular such as the oncogene HER-2/Neu/ErbB-2. Yet another group of target antigens are onco-fetal antigens such as carcinoembryonic antigen (CEA). In B-cell lymphoma, the tumor-specific immunoglobulin constitutes a truly tumor-specific immunoglobulin antigen that is unique to the individual tumor. B-cell differentiation antigens such as CD19, CDd20; ROR1, CD22, CD23, λ/κ light chains are other candidates for target antigen in B-cell lymphoma.

The type of tumor antigen referred to may also be a tumor specific antigen (TSA) or tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond, or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-1), gp100 (Pme117), tyrosinanse, TRP-1, TRP-2 and tumor-specific mutilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL. E2A-PRL, H4-RET, IGH-IGK, MYL-RAR; and viral antigens such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-catenin, CDK4, Mum-1, p 15, p 16, 43-9F, 5T4, 791Tgp72, alpha-fetoprotein, beta-HCG, BCA224, BTAA, CA 125, CA 15-3\CA 27/29\BCAA, CA 195, CA 242, CA-50, CAM43, CD68\P1, CO-029, FGF-5, C250, GA733\EpCAM, HTgp-175, M344, MA-50, MG7-Ag, MOV18, NB/70K, NY-CO-1, RCAS1, SDCCAG16, TA-90, MAC-2 binding protein\cyclophillin C-associated protein, TAA16, TAG72, TLP, and TPS, CD19, CD20, CD22, ROR1, Mesothelin, CD33/IL3Ra, c-met, PSMA, Glycolipid F77, EGRvIII, GD-2, MY-ESO-1 TCR, MAGE A3 TCR, and others.

Infectious Diseases

The immune response to infectious diseases involves a balance of anti-pathogen and anti-inflammatory responses. T cells are heavily involved in this intricate balance. Infectious pathogens capable of eliciting a T cell response may be bacterial, viral, parasitic or fungal. Treg cells have been implicated in contributing to the chronicity of infection by *Helicobacter pylori* (Lundgren A, et al. Infect Immun 2003; 71:1755-62), hepatitis B virus (HBV), and hepatitis C virus (HCV) (Cabrera R, et al., Hepatology 2004; 40:1062-71; Stoop J N, et al. Hepatology 2005; 41:771-8; Sugimoto K, et al., Hepatology 2003; 38:1437-48). This elevation in a particular T cell subpopulation may contribute to the prolonged nature of these infections by inappropriately suppressing memory T cell responses. The compositions of the present invention may be utilized to specifically expand a particular T cell subpopulation and could be utilized in the treatment of such infectious diseases.

Infectious disease can be caused by direct contact with a pathogen and spread from person to person, animal to person, or from mother to unborn child. Infectious diseases can alternatively spread through indirect contact, e.g., from contact with an infected surface such as door handle, table, counter or faucet handle. Infectious diseases can further be spread via insect bites or food contamination. Certain autoimmune disorders, such as HIV or AIDS, and some cancers can increase susceptibility to infectious diseases. Certain treatment regimens that supress the immune system can also enhance susceptibility to infectious diseases. Example infectious diseases include: smallpox, malaria, tuberculosis, typhus, plague, diphtheria, typhoid, cholera, dysentery, pneumonia.

As described above, expansion of T cells may be used in the treatment of disease states. In infectious disease states, a patient suffering from the infection does not have sufficient immunity to the infectious agent. Methods of the present invention may be used to expand heterologous T memory cells from a donor with immunity to a particular infectious agent and utilized in adoptive T-cell transfer. The externally expanded T cells from an infectious agent experienced donor can then be infused into a patient inflicted with the infection. In certain embodiments, T cells are administered at $1\times10^5$, $1\times10^6$, $1\times10^7$, $1\times10^8$, $5\times10^8$, $1\times10^9$, $5\times10^9$, $1\times10^{10}$, $5\times10^{10}$, $1\times10^{11}$, $5\times10^{11}$, or $1\times10^{12}$ cells to the subject. The infectious antigen competent donor memory T cells can then aid in mounting an autologous immune response within the patient.

Alternative methods of utilizing the present invention in the treatment of infectious diseases include the expansion of autologous or heterologous Th17 cells for reinfusion or adoptive cell transfer respectively. Using methods described herein, T cells can be externally expanded from patient isolated blood or tissue. These expanded T cells can then be infused to the patient to aid in induction of B cells to secrete antibodies against the particular infectious antigen (e.g., Streptococci M-protein, *Neisseria pilli*, *Borrelia burgdorferi* lipoprotein VisE, *B. pseudomallei* polysaccharide antigens, *Aspergillus fumigatus* galactomannan, or *F. tularensis* lipopolysaccharide). In certain embodiments, T cells are administered at $1\times10^5$, $1\times10^6$, $1\times10^7$, $1\times10^8$, $5\times10^8$, $1\times10^9$, $5\times10^9$, $1\times10^{10}$, $5\times10^{10}$, $1\times10^{11}$, $5\times10^{11}$, or $1\times10^{12}$ cells to the subject.

Co-Therapies

Existing treatments may be recommended for many of the above listed disease states. T cell subpopulations expanded by the present invention may be used as sole replacement therapy in some cases or in conjunction with other known therapies. T cell therapies may be administered prior to, concurrently with, or following administration of other therapies.

The methods of the present invention may also be utilized with vaccines to enhance reactivity of the antigen and enhance in vivo effect. In one embodiment, the compositions of the present invention are administered to a patient in conjunction with a composition that enhances T cells in vivo, for example, IL-2, IL-4, IL-7, IL-10, IL-12, and/or IL-15. Further, given that T cells expanded by the present invention have a relatively long half-life in the body, these cells could act as perfect vehicles for gene therapy as described above, by carrying a desired nucleic acid sequence of interest and potentially homing to sites of cancer, disease, or infection. Accordingly, the cells expanded by the present invention may be delivered to a patient in combination with a vaccine, one or more cytokines, one or more therapeutic antibodies, etc. Virtually any therapy that would benefit by a more robust T cell population could be used in conjunction with the compositions of the present invention.

V. Kits of the Invention

Also provided herein are kits comprising (i) compositions for the isolation of T cells from a subject; (ii) compositions for the ex vivo culture of T cells (iii) compositions for the expansion of one or more T cell subpopulation (e.g., Th17, Th9, Treg, memory T cells, CAR T cells, etc.). Kits of the invention may optionally include compositions for the re-activation of Treg cells.

Kits can also include written instructions for use of the kit, such as instructions for wash steps, culturing conditions and duration of incubation of isolated T cells with compositions of the invention for selective expansion of specific T cell subpopulations.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

EXAMPLES

The invention can be further understood by reference to the following examples, which are provided by way of illustration and are not meant to be limiting.

Example 1. Culturing T Cells in Galactose Alone

Primary human T cells from normal donors were negatively isolated from PBMCs with DYNABEADS® UNTOUCHED™ Human T Cells kit. T cells (seeding density $1\times10^6$/mL) were activated with DYNABEADS® Human T-Expander CD3/CD28 at a ratio of 3 beads per T cell and cultured in serum-free medium supplemented with GIBCO™ Chemically Defined Lipid Concentrate (1:100) and either d-glucose, d-galactose or mixtures of glucose and galactose as indicated; final concentration of sugar was 6 g/L in all conditions. T cells were fed and counted on days 5, 7, 10 and 12 on a Beckman-Coulter ViCell analyzer. Cell expansion is expressed as cumulative viable T cells over time. Results are representative of at least 3 independent experiments.

Figure 3:
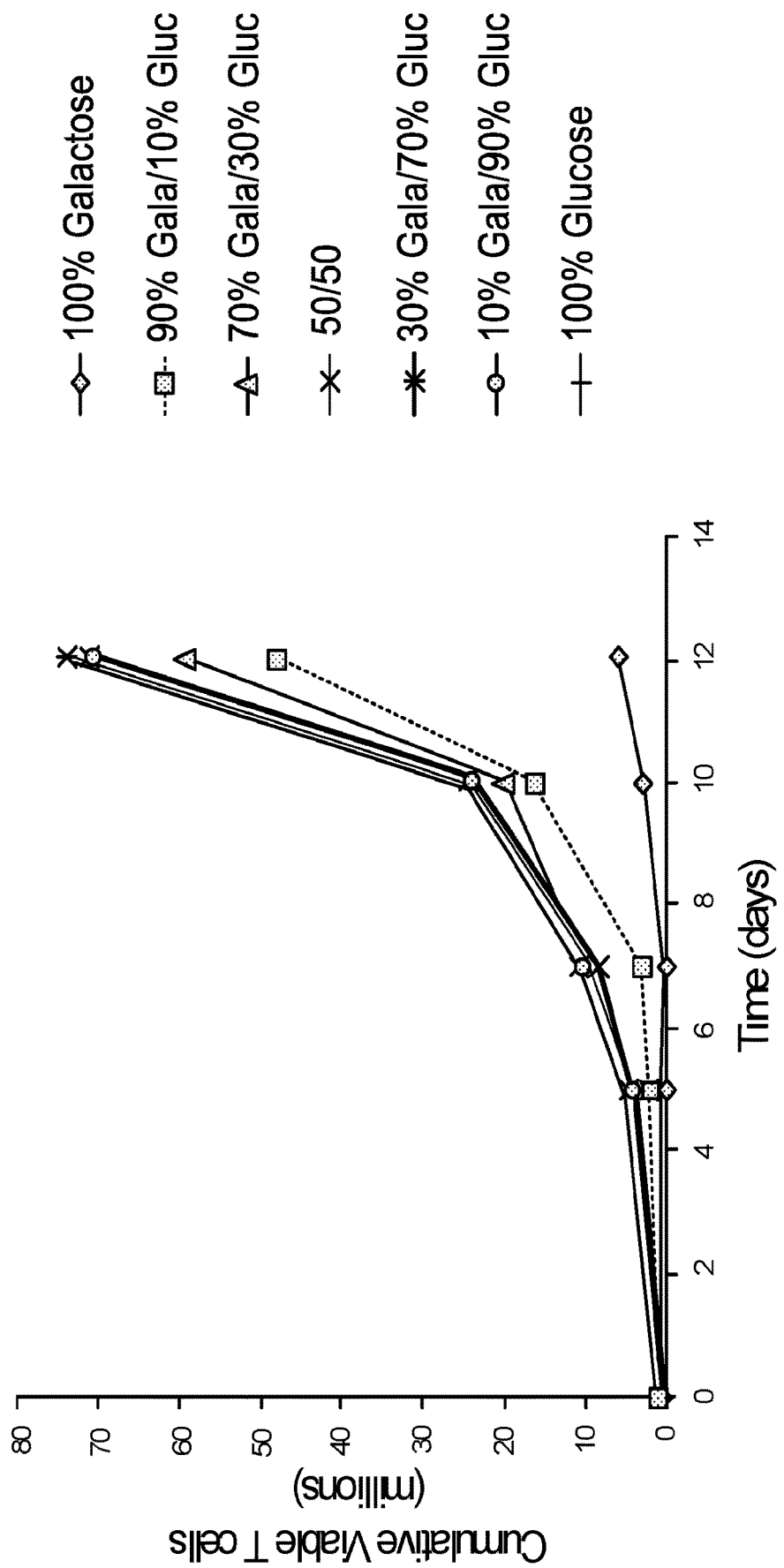
FIG. 3 is a graph depicting that galactose alone is suboptimal for human T cell expansion. Primary human T cells from normal donors were negatively isolated from PBMCs with DYNABEADS® UNTOUCHED™ Human T Cells kit. T cells (seeding density $1\times10^6$/mL) were activated with DYNABEADS® Human T-Expander CD3/CD28 at a ratio of 3 beads per T cell and cultured in serum-free medium supplemented with GIBCO™ Chemically Defined Lipid Concentrate (1:100) and either d-glucose, d-galactose or mixtures of glucose and galactose as indicated; final concentration of sugar was 6 g/L in all conditions. T cells were fed and counted on days 5, 7, 10 and 12 on a Beckman-Coulter ViCell analyzer. Cell expansion is expressed as cumulative viable T cells over time. Results are representative of at least 3 independent experiments.

As depicted in FIG. 3, data indicates that D-galactose alone is not sufficient to support optimal in vitro T cell expansion, while combinations of glucose and galactose at 30%, 50% and 70% expand T cells comparably to media with just glucose.

Primary T cells were analyzed for the ability to metabolize galactose when undergoing glucose starvation. Primary human T cells from normal donors were isolated from PBMCs with DYNABEADS® UNTOUCHED™ Human T cells. T cells were seeded at a density of $1\times10^6$/mL and were activated with DYNABEADS® Human T-Expander CD3/CD28 at a ratio of 3 beads per T cell. Cells were cultured in serum-free medium supplemented with GIBCO™ Chemically Defined Lipid Concentrate (1:100) and either glucose or mixtures of glucose and galactose at the indicated concentrations. T cells were counted and fed to a cell density of $5 \times 10^5$ on day 3, then left unfed in batch cultures to simulate starvation and counted on days 5 and 6 on a Beckman-Coulter ViCell analyzer. T cell expansion is expressed as population doublings over time. Supernatants were analyzed on a Roche Cedex BioHT analyzer to measure glucose and galactose consumption over time.

Figure 4A:
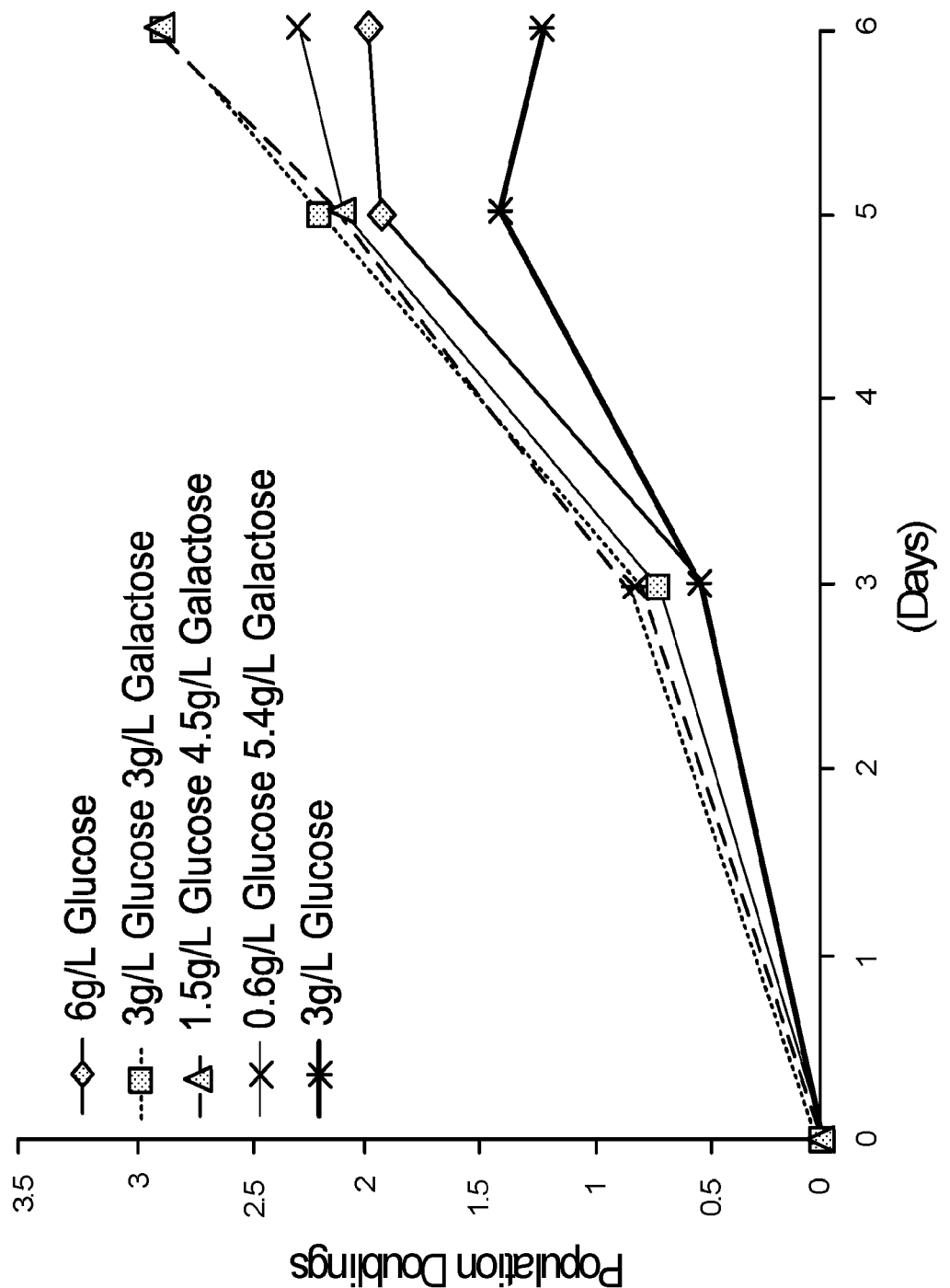
FIG. 4A-4C is a series of graphs demonstrating that primary human T cells do not metabolize galactose. As described herein, primary T cells do not appreciably metabolize galactose, even when undergoing glucose starvation.
Figures 4B, 4C:
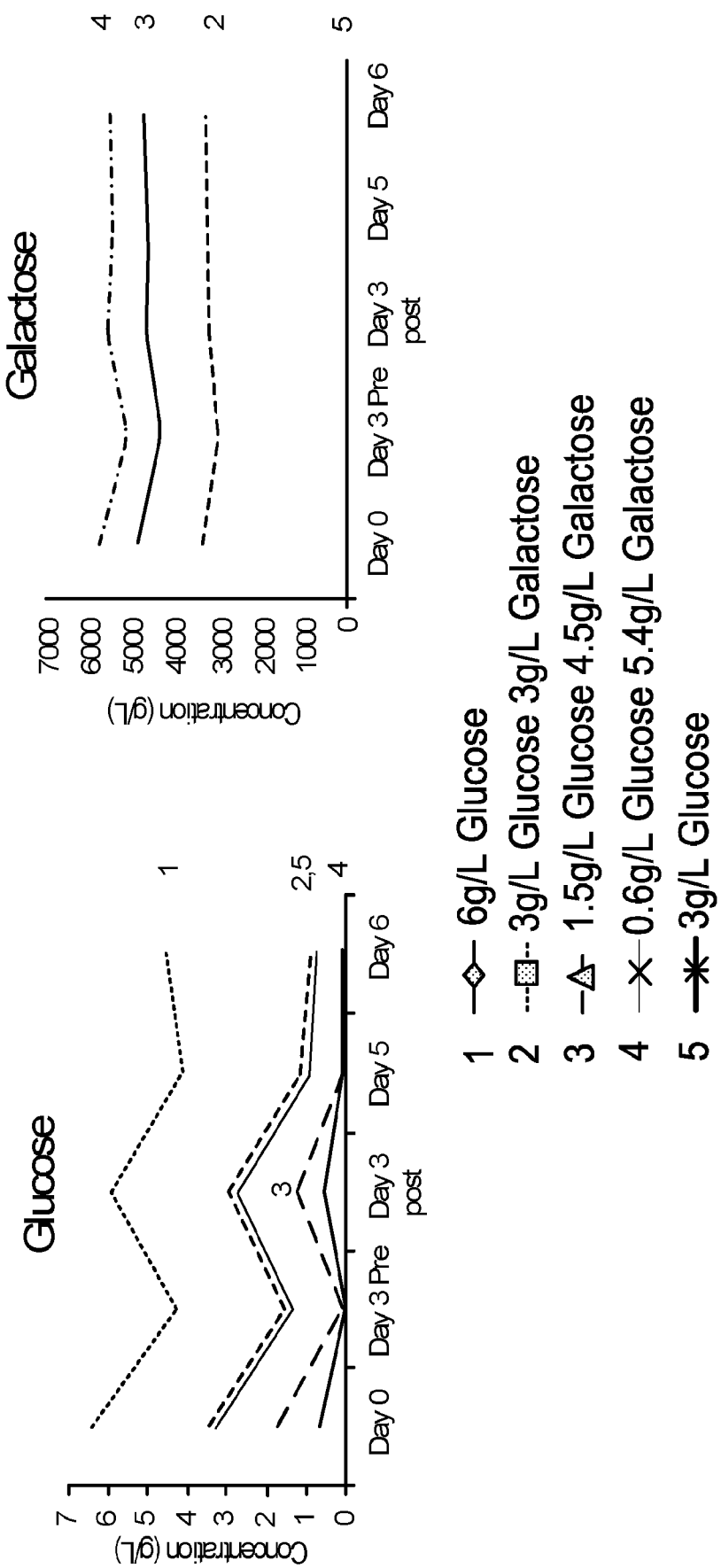

As depicted in FIG. 4A, expansion of T cells in the indicated medium was expressed as population doublings over time. There was superior cell culture performance for cells grown in 3 g/L glucose+3 g/L galactose medium versus 3 g/L glucose medium. FIG. 4B depicts glucose analysis from T cell culture supernatants. Consumption of glucose is detected in all cultures from day 0 to day 3 pre-feeding as well as post fed supernatant on Day 3 to Day 6. FIG. 4C depicts galactose analysis from T cell culture supernatant. No appreciable consumption of Galactose was detected, even in conditions with depleted glucose as shown in FIG. 4B. These results demonstrate that while galactose is not metabolized by T cells, its presence in T cell culture medium provides a cell growth advantage that is not related to its catabolism.

Figure 5A:
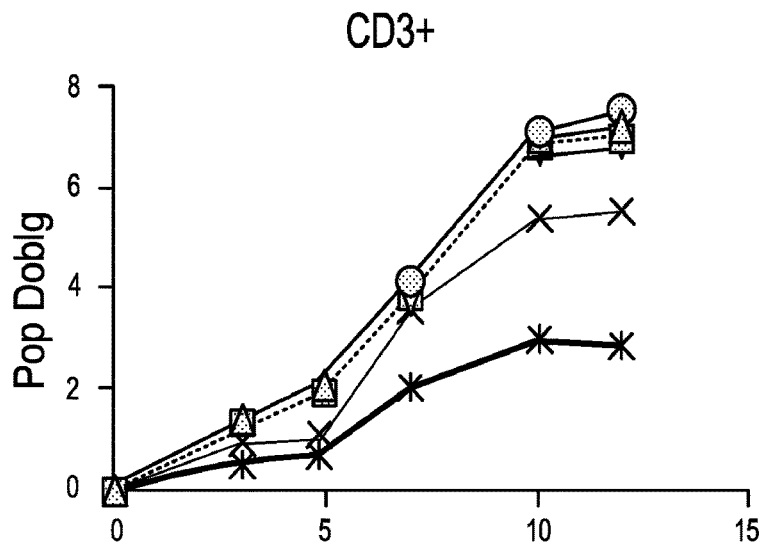
FIG. 5A-5C is series of graphs demonstrating that primary human T cell subsets do not metabolize galactose. Primary human Pan-CD3+ T cells from normal donors were isolated from PBMCs with DYNABEADS® UNTOUCHED™ Human T Cells, CD4+ T cells were isolated with DYNABEADS® UNTOUCHED™ Human CD4 T Cells Kit and CD8+ T cells were isolated with DYNABEADS® UNTOUCHED™ Human CD8 T Cells Kit. T cells (seeding density $1\times10^6$/mL) were activated with DYNABEADS® Human T-Expander CD3/CD28 at a ratio of 3 beads per T cell and cultured in serum-free medium supplemented with GIBCO™ Chemically Defined Lipid Concentrate (1:100) and either glucose, galactose or mixtures of glucose and galactose as indicated (final concentration of sugar was 10 g/L in all conditions) or control medium Lonza X-VIVO™ 15 supplemented with 5% human AB serum. T cells were fed and counted on days 3, 5, 7, 10 and 12 on a Beckman-Coulter ViCell analyzer. T cell expansion was expressed as population doublings over time. Supernatants were analyzed on a Roche Cedex BioHT to measure galactose consumption over time. CD4+ and CD8+ T cells (FIG. 5B and FIG. 5C; respectively) show no appreciable metabolism of galactose, as shown for pan-CD3+ T cells (FIG. 5A). Results are representative of at least 2 independent experiments.
Figure 5A:
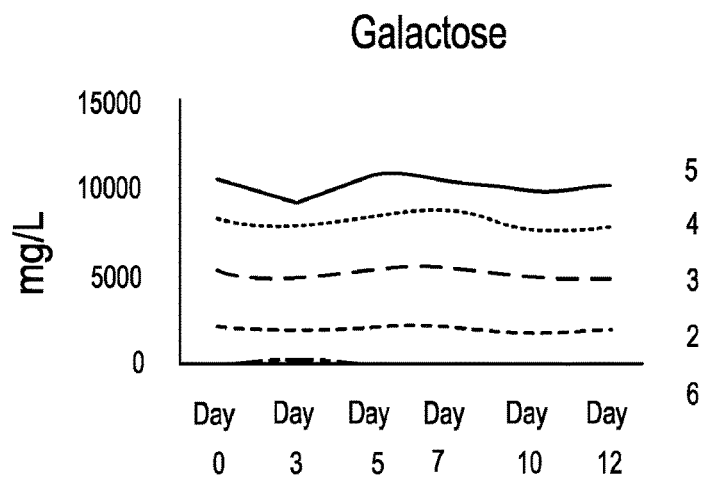
Figure 5B:
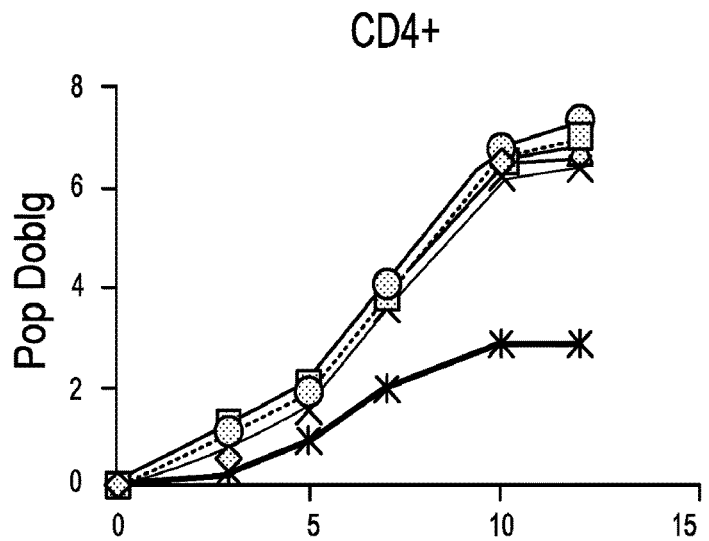
Figure 5B:
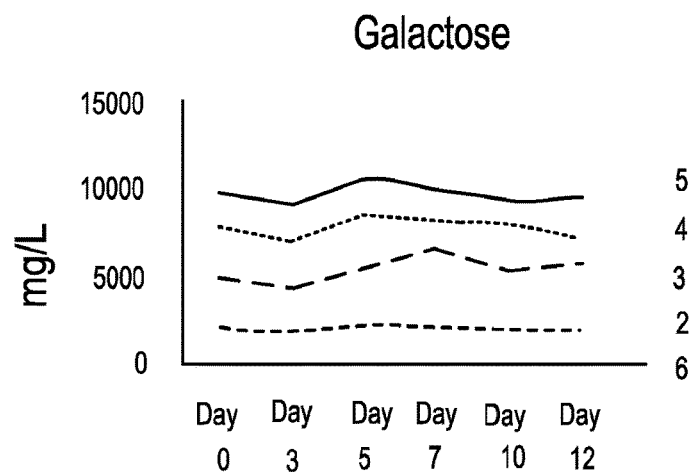
Figure 5C:
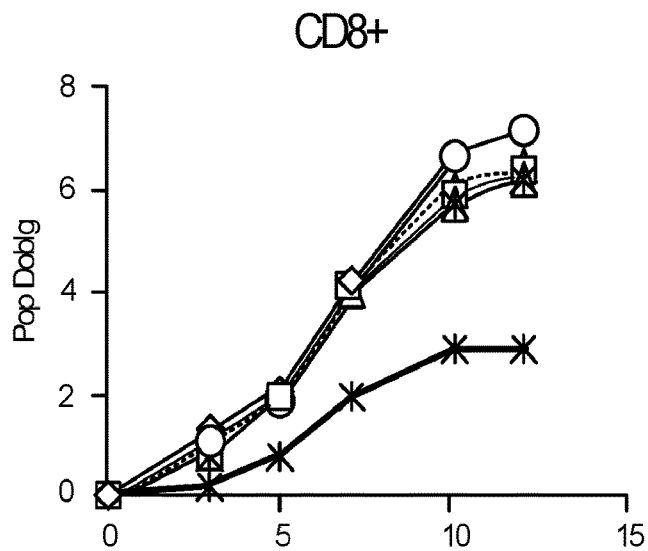
Figure 5C:
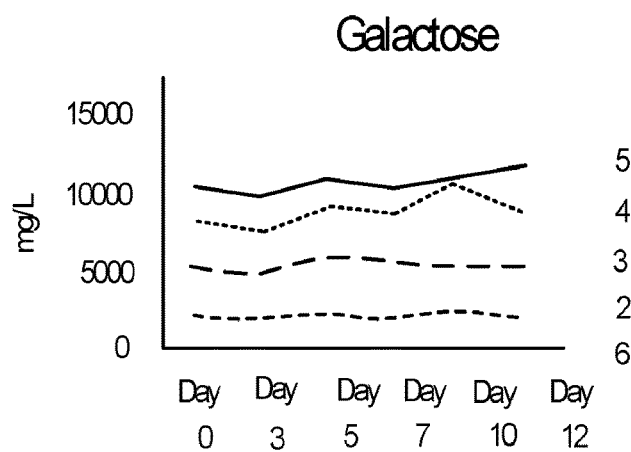
Figure 6:
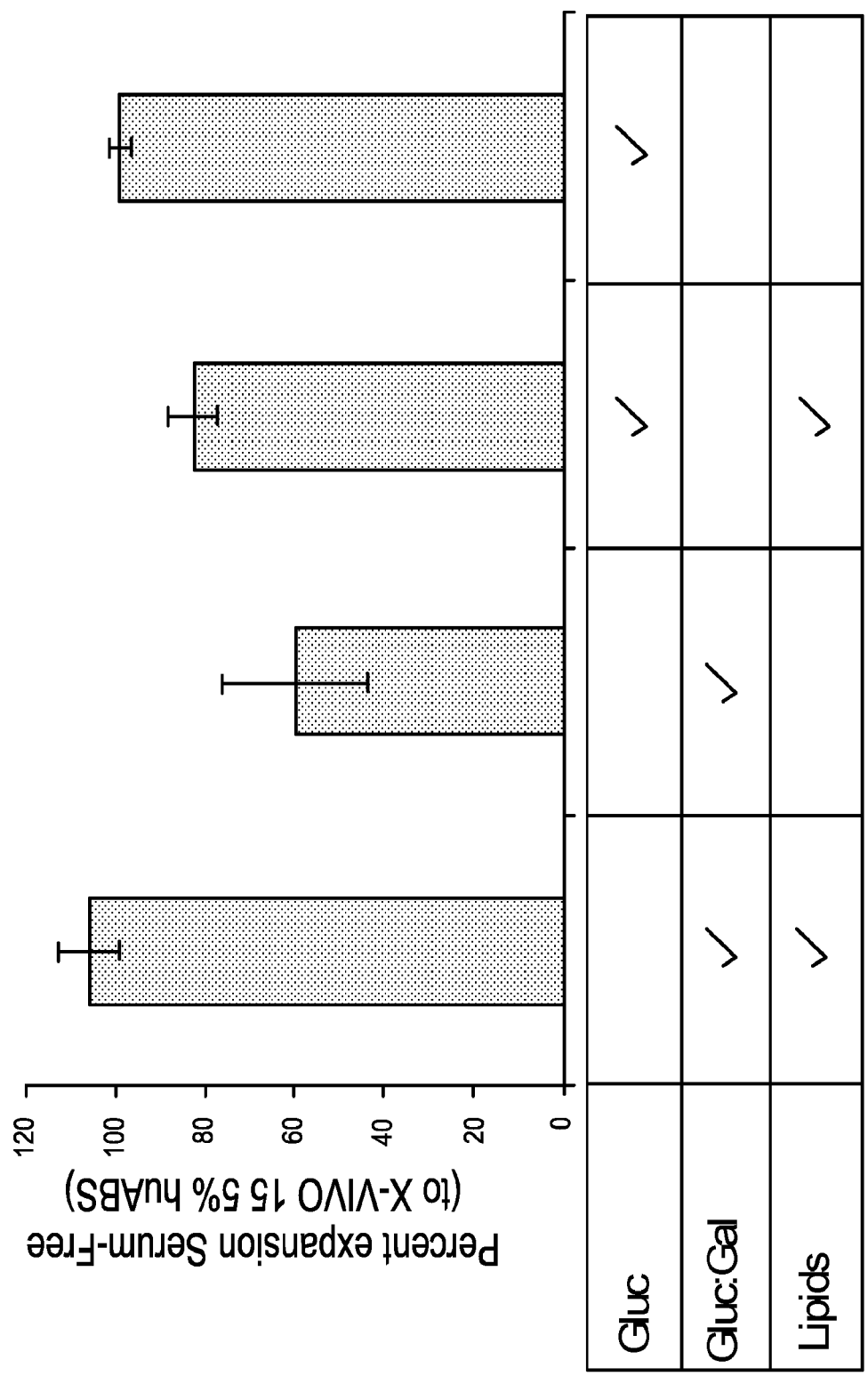
FIG. 6 is a graph depicting that lipids are required for human T cell expansion in glucose:galactose medium. T cells from three normal donors were expanded in control medium. Primary human T cells from three normal donors were isolated from PBMCs with DYNABEADS® UNTOUCHED™ Human T cells. T cells were seeded at a density of $1 \times 10^6$/mL and were activated with DYNABEADS® Human T-Expander CD3/CD28 at a ratio of 3 beads per T cell. Cells were cultured in control medium Lonza X-VIVO™ 15 supplemented with 5% human AB serum or in serum-free medium containing glucose or a 1:1 mixture of glucose and galactose alone or supplemented with GIBCO™ Chemically Defined Lipid Concentrate (1:100). T cells were counted on a Beckman-Coulter ViCell analyzer and fed to a cell density of $5 \times 10^5$ on day 3, 5, 7, 10 and 12. Fold expansion was calculated and expressed as a percent of fold expansion in control medium for each donor. Results demonstrate that glucose/galactose serum-free medium required lipid supplementation for optimal performance while lipids exerted little impact on medium containing glucose alone.

Primary human T cell subsets were analyzed for the ability to metabolize galactose. Primary human Pan-CD3+ T cells from normal donors were isolated from PBMCs with DYNABEADS® UNTOUCHED™ Human T Cells, CD4+ T cells were isolated with DYNABEADS® UNTOUCHED™ Human CD4 T Cells Kit and CD8+ T cells were isolated with DYNABEADS® UNTOUCHED™ Human CD8 T Cells Kit. T cells (seeding density $1 \times 10^6$/mL) were activated with DYNABEADS® Human T-Expander CD3/CD28 at a ratio of 3 beads per T cell and cultured in serum-free medium supplemented with GIBCO™ Chemically Defined Lipid Concentrate (1:100) and either glucose, galactose or mixtures of glucose and galactose as indicated (final concentration of sugar was 10 g/L in all conditions) or control medium Lonza X-VIVO™ 15 supplemented with 5% human AB serum. T cells were fed and counted on days 3, 5, 7, 10 and 12 on a Beckman-Coulter ViCell analyzer. T cell expansion was expressed as population doublings over time. Supernatants were analyzed on a Roche Cedex BioHT to measure galactose consumption over time. CD4+ and CD8+ T cells (FIG. 5B and FIG. 5C; respectively) show no appreciable metabolism of galactose, as shown for pan-CD3+ T cells (FIG. 5A). Results are representative of at least 2 independent experiments.

Example 2. Use of Lipids in Glucose:Galactose Media

Lipids appear to be the OXPHOS source of energy for T cells grown in galactose-containing serum-free medium and are required for optimal T cell expansion. T cells from three normal donors were expanded in control medium. Primary human T cells from three normal donors were isolated from PBMCs with DYNABEADS® UNTOUCHED™ Human T cells. T cells were seeded at a density of $1 \times 10^6$/mL and were activated with DYNABEADS® Human T-Expander CD3/CD28 at a ratio of 3 beads per T cell. Cells were cultured in control medium Lonza X-VIVO™ 15 supplemented with 5% human AB serum or in serum-free medium containing glucose or a 1:1 mixture of glucose and galactose alone or supplemented with GIBCO™ Chemically Defined Lipid Concentrate (1:100). Lipids include: cholesterol, arachidonic acid, linoleic acid, linolenic acid, myristic acid, oleic acid, palmitic acid, palmitoleic acid and stearic acid. Lipid delivery may be through emulsion or carriers (e.g., albumin or cyclodextrins). T cells were counted on a Beckman-Coulter ViCell analyzer and fed to a cell density of $5 \times 10^5$ on day 3, 5, 7, 10 and 12. Fold expansion was calculated and expressed as a percent of fold expansion in control medium for each donor. Results demonstrate that glucose/galactose serum-free medium requires lipid supplementation for optimal performance while lipids exert little impact on medium containing glucose alone.

Figure 7:
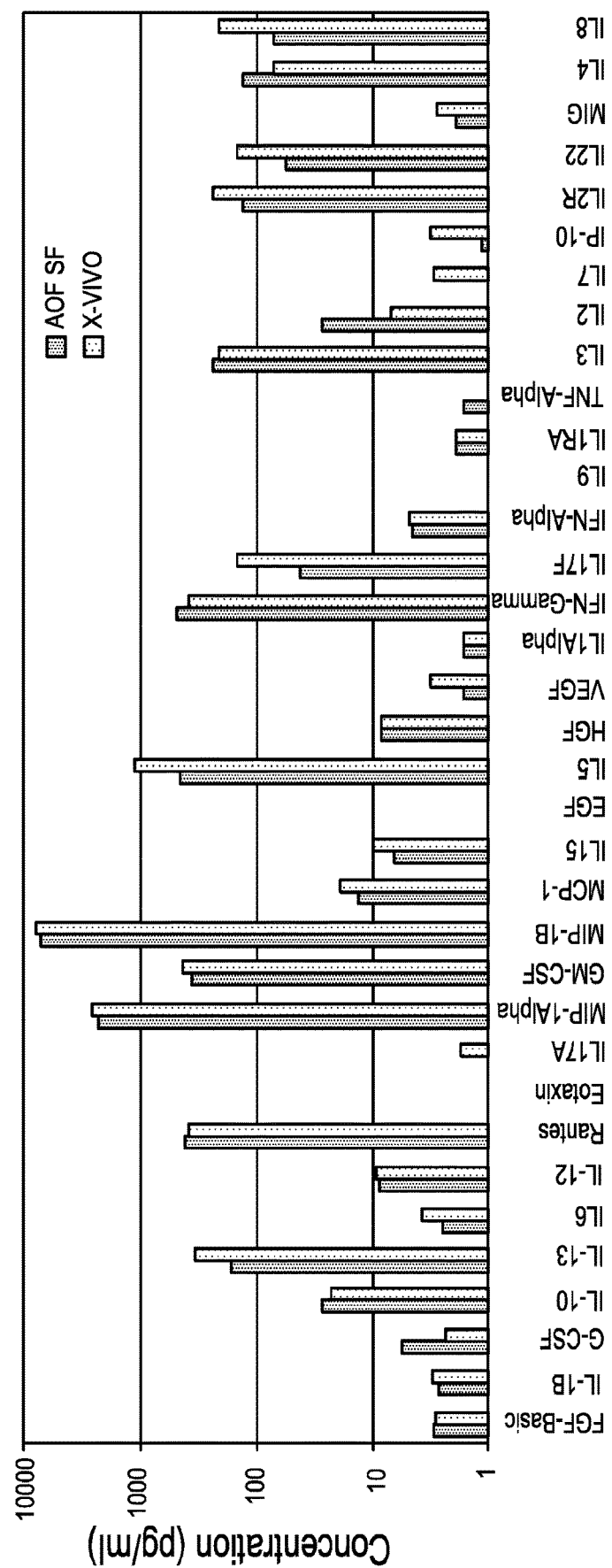
FIG. 7 is a graph demonstrating comparable Th-1 cytokine profiles in serum-free glucose:galactose medium vs. serum-containing medium. Primary human T cells from normal donors were negatively isolated from PBMCs with DYNABEADS® UNTOUCHED™ Human T Cells kit. T cells (seeding density $1 \times 10^6$/mL) were activated with DYNABEADS® Human T-Expander CD3/CD28 at a ratio of 3 beads per T cell and cultured in serum-free medium supplemented with GIBCO™ Chemically Defined Lipid Concentrate (1:100) and 3 g/L each glucose and galactose or in Control Medium Lonza X-VIVO™ 15 supplemented with 5% human AB serum. T cells were fed and counted on days 3, 5, 7 and 10 on a Beckman-Coulter ViCell analyzer. DYNABEADS were removed from the cultures on day 11 and cells were spun to remove conditioned medium and rested overnight in fresh medium. One million T cells were re-stimulated with DYNABEADS® CD3 at a 1:1 bead to cell ratio and incubated for 24 hours. Supernatants were collected and processed for analysis with Invitrogen Cytokine Human Magnetic 35-Plex Panel for Luminex™. Results demonstrate that T cells expanded in serum-free glucose/galactose medium (3 g/L each sugar) show a similar profile of cytokines with no impairment of IFNγ production when compared to control serum-supplemented media (data representative of two independent experiments).

Example 3. Cytokine Profiles in Serum-Free Glucose:Galactose Media Vs. Serum-Containing Media T cells expanded with DYNABEADS® Human T-Expander CD3/CD28 typically show a predominant Th1-like effector function. IFN-g is a key mediator of Th1 immune responses and secretion of IFNγ can be impaired when T cells are in a low glucose environment. Th1 cytokine profiles were compared between T cells grown in serum-free glucose:galactose media vs. serum-containing media. Primary human T cells from normal donors were negatively isolated from PBMCs with DYNABEADS® UNTOUCHED™ Human T Cells kit. T cells (seeding density $1 \times 10^6$/mL) were activated with DYNABEADS® Human T-Expander CD3/CD28 at a ratio of 3 beads per T cell and cultured in serum-free medium supplemented with GIBCO™ Chemically Defined Lipid Concentrate (1:100) and 3 g/L each glucose and galactose or in Control Medium Lonza X-VIVO™ 15 supplemented with 5% human AB serum. T cells were fed and counted on days 3, 5, 7 and 10 on a Beckman-Coulter ViCell analyzer. DYNABEADS were removed from the cultures on day 11 and cells were spun to remove conditioned medium and rested overnight in fresh medium. One million T cells were re-stimulated with DYNABEADS® CD3 at a 1:1 bead to cell ratio and incubated for 24 hours. Supernatants were collected and processed for analysis with Invitrogen Cytokine Human Magnetic 35-Plex Panel for Luminex™. As depicted in FIG. 7, results demonstrate that T cells expanded in serum-free glucose/galactose medium (3 g/L each sugar) show a similar profile of cytokines with no impairment of IFN-γ production when compared to control serum-supplemented media (data representative of two independent experiments).

Example 4. Phenotype of Expanded T Cells in Glucose:Galactose Media

Figure 8A:
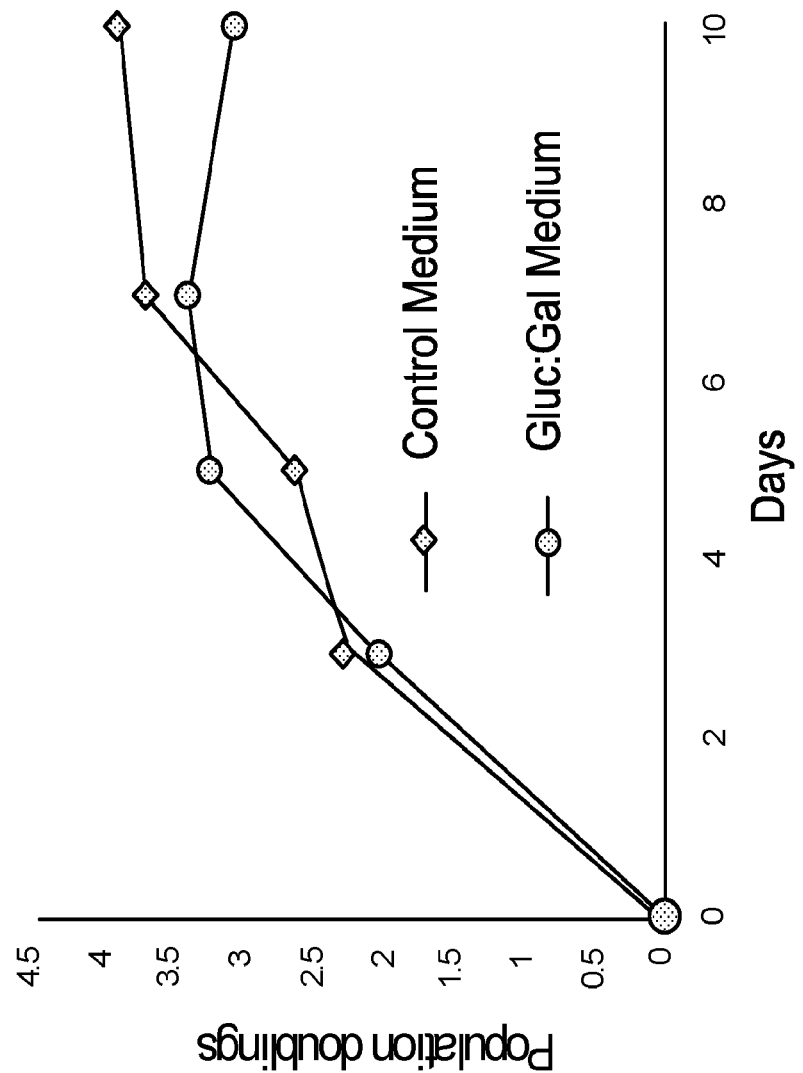
FIG. 8A-FIG. 8D is a series of graphs demonstrating a preservation of naïve and central memory subsets in T cells expanded in glucose:galactose medium.
Figure 8B:
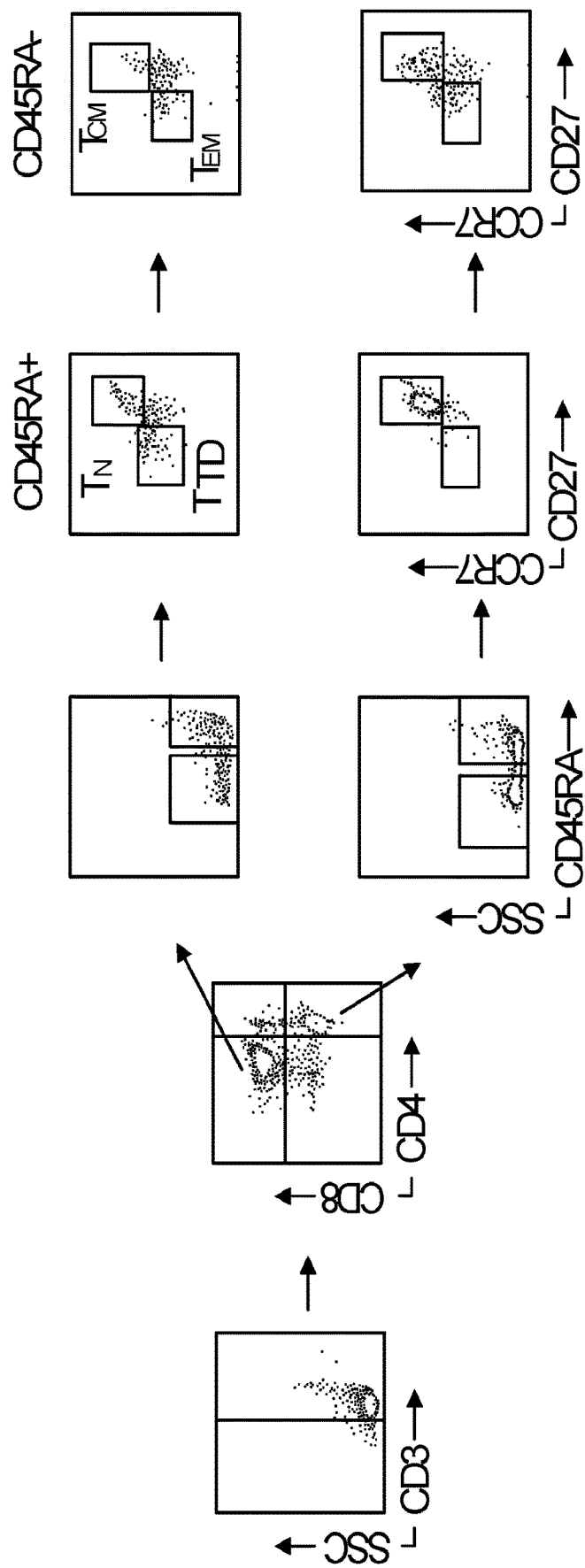
Figure 8D:
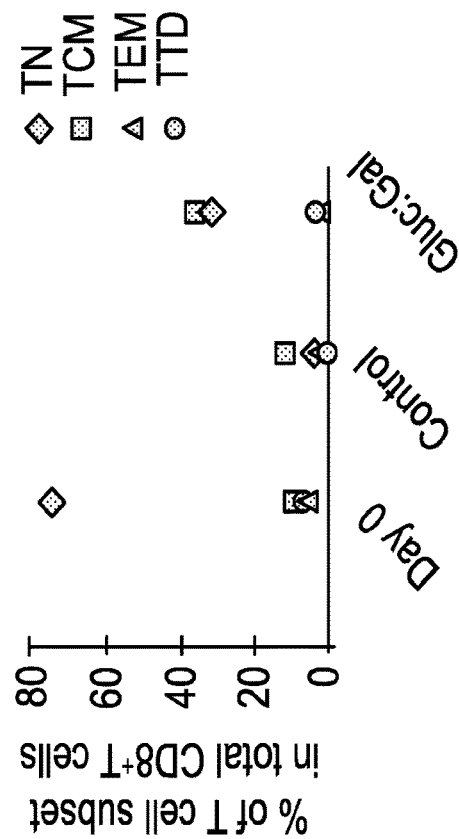
Figure 8C:
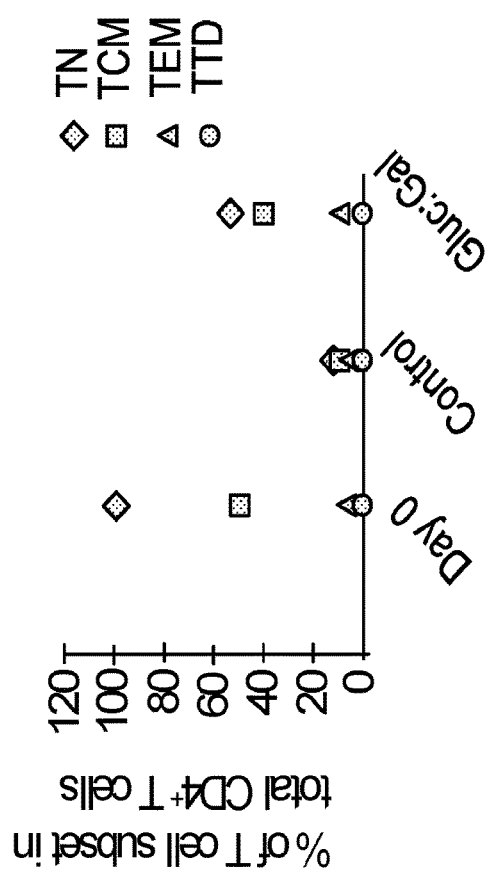

The preservation of naïve and central memory subsets of T cells were expanded in glucose:galactose media. Primary human T cells from normal donors were negatively isolated from PBMCs with DYNABEADS® UNTOUCHED™ Human T Cells kit. T cells (seeding density $1 \times 10^6$/mL) were activated with DYNABEADS® Human T-Expander CD3/CD28 at a ratio of 3 beads per T cell and cultured in serum-free medium supplemented with GIBCO™ Chemically Defined Lipid Concentrate (1:100) and 3 g/L each glucose and galactose; Control Medium Lonza X-VIVO™ 15 supplemented with 5% human AB serum. T cells were counted on days 3, 5, 7 and 10 on a Beckman-Coulter ViCell analyzer and fed to a density of $5 \times 10^5$ cells/mL on days 3 and 7. T cell expansion is expressed as population doublings over time, as depicted in FIG. 8A. FIG. 8B depicts the gating strategy for differentiation phenotyping. Expanded T cells were stained with antibodies against CD3, CD4, CD8, CD45RA, CD27 and CCR7. Sequential gating was used to characterize T cells as naïve (TN: CD45RA+/CD27+/CCR7+), terminally differentiated effectors (TTD: CD45RA+/CD27−/CCR7−), central memory (TCM: CD45RA−/CD27+/CCR7+); and effector memory (TEM: CD45RA−/CD27−/CCR7−). Flow cytometric analysis was performed in a Beckman-Coulter Gallios analyzer. FIG. 8C depicts the differentiation status of CD4+ T cells expanded in control or glucose/galactose media compared to original subset distribution (Day 0). FIG. 8D depicts the differentiation status of CD8+ T cells expanded in control or glucose/galactose media compared to original subset distribution (Day 0). Results demonstrate the more favorable phenotype of T cells expanded in glucose/galactose medium as defined by greater frequencies of naïve and memory cell subsets at harvest versus control medium.

Figure 9:
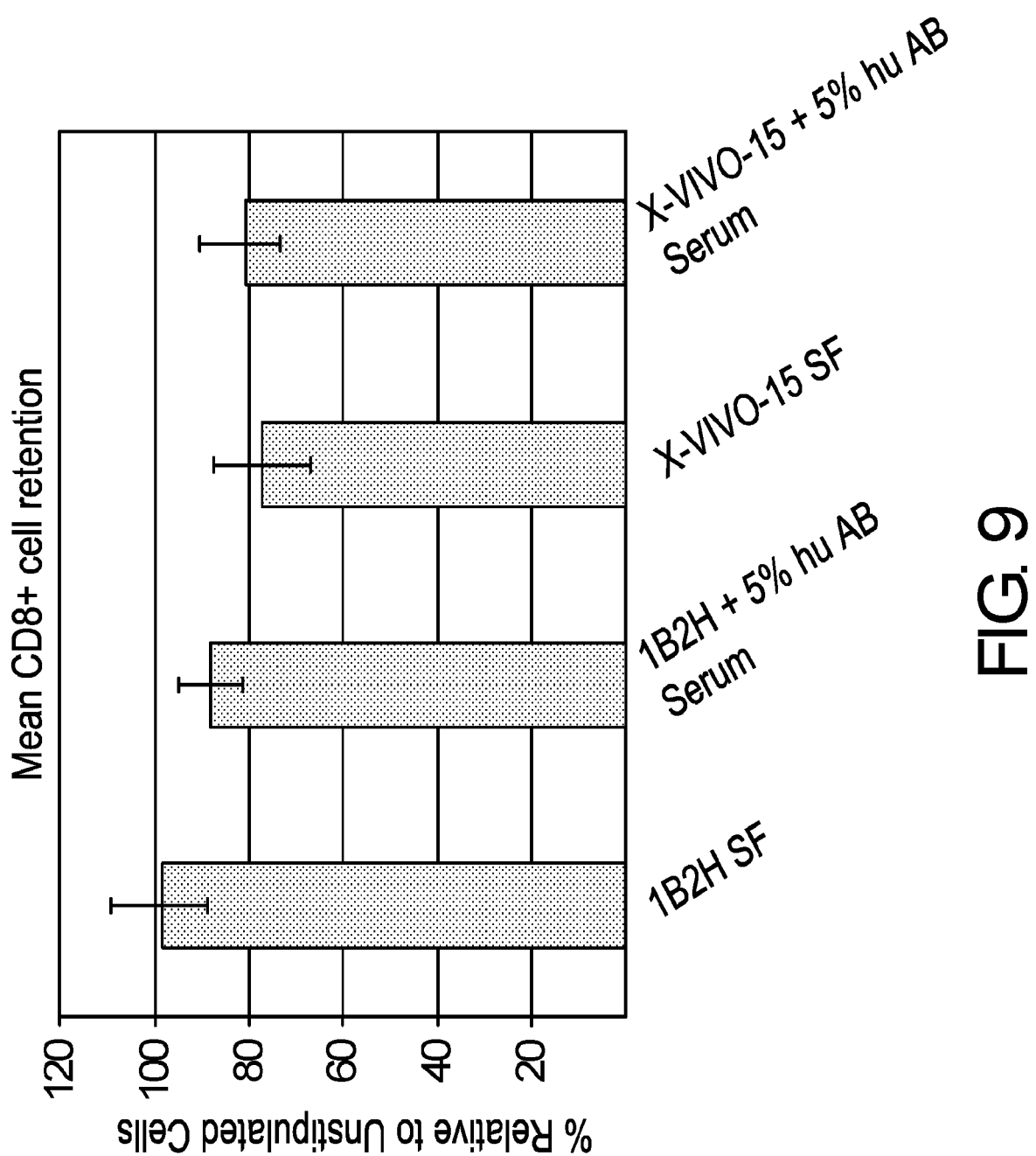
FIG. 9 is a graph demonstrating improved retention of CD8+ T cell subset in glucose/galactose serum-free medium. Primary human T cells from three normal donors were isolated from PBMCs with DYNABEADS® UNTOUCHED™ Human T cells. T cells were seeded at a density of $1 \times 10^6$/mL and were activated with DYNABEADS® Human T-Expander CD3/CD28 at a ratio of 3 beads per T cell. Cells were cultured in Lonza X-VIVO™ 15 medium alone, Lonza X-VIVO™ 15 medium with 5% human AB serum, serum-free medium containing a 1:1 mixture of glucose and galactose alone or supplemented with 5% human AB serum. T cells were counted on a Beckman-Coulter ViCell analyzer and fed to a cell density of $5 \times 10^5$ on day 3, 5, 7, 10 and 12. T cells were stained with antibodies against CD3, CD4 and CD8 prior to stimulation and after 10 days post-expansion. Frequency of CD8+ T cells post expansion was compared to the frequency before expansion and expressed as a percentage. Results were compiled from multiple independent experiments with cells derived from 9 normal donors.

Example 5. Improved CD8+ T Cell Subset Retention by Glucose:Galactose Serum-Free Media The retention of CD8+ T cell subsets in glucose/galactose serum-free medium was analyzed. Primary human T cells from three normal donors were isolated from PBMCs with DYNABEADS® UNTOUCHED™ Human T cells. T cells were seeded at a density of $1 \times 10^6$/mL and were activated with DYNABEADS® Human T-Expander CD3/CD28 at a ratio of 3 beads per T cell. Cells were cultured in Lonza X-VIVO™ 15 medium alone, Lonza X-VIVO™ 15 medium with 5% human AB serum, serum-free medium containing a 1:1 mixture of glucose and galactose alone or supplemented with 5% human AB serum. T cells were counted on a Beckman-Coulter ViCell analyzer and fed to a cell density of $5 \times 10^5$ on day 3, 5, 7, 10 and 12. T cells were stained with antibodies against CD3, CD4 and CD8 prior to stimulation and after 10 days post-expansion. Frequency of CD8+ T cells post expansion was compared to the frequency before expansion and expressed as a percentage. Results compiled from multiple independent experiments with cells derived from 9 normal donors. As depicted in FIG. 9, results show 99% retention of CD8+ T cells post expansion in glucose/galactose serum-free medium when compared to the frequencies in control media. Serum supplementation has a slight negative effect in glucose/galactose medium when compared to control media which shows similar CD8+ T cell frequencies irrespective of serum supplementation.

Figures 10A, 10B:
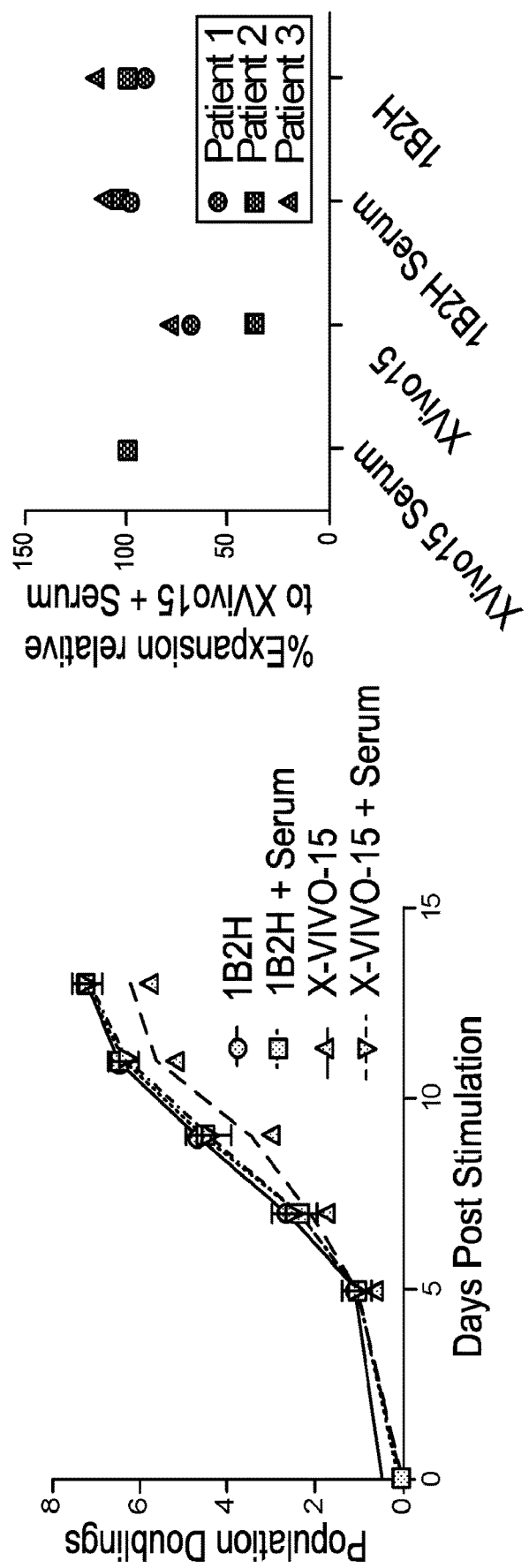
FIG. 10A-FIG. 10F is a series of graphs demonstrating that 1B2H media (serum free media) supports the expansion of a more differentiated T cell phenotype. After 11 days of culture, T cells were stained for CCR7 and CD27 expression. Representative data from CD4+ T cells is shown in FIG. 10A. CD8+ T cells are shown in FIG. 10B. To determine whether 1B2H (serum free media) was able to more efficiently expand highly differentiated T cells isolated from multiple myeloma patients, T cell expansion studies were performed using cryopreserved, de-identified apheresis products from multiple myeloma patients involved in a previous adoptive T cell therapy clinical trial. X-VIVO™ 15 was required to be supplemented with human serum to expand patient T cells, as T cells expanded in X-VIVO™ 15 SFM. Serum supplementation was not able to significantly improve expansion using glucose/galactose medium 1B2H (as depicted in FIG. 10B). Composite data from 3 donors is shown in FIG. 10C.
Figure 10C:
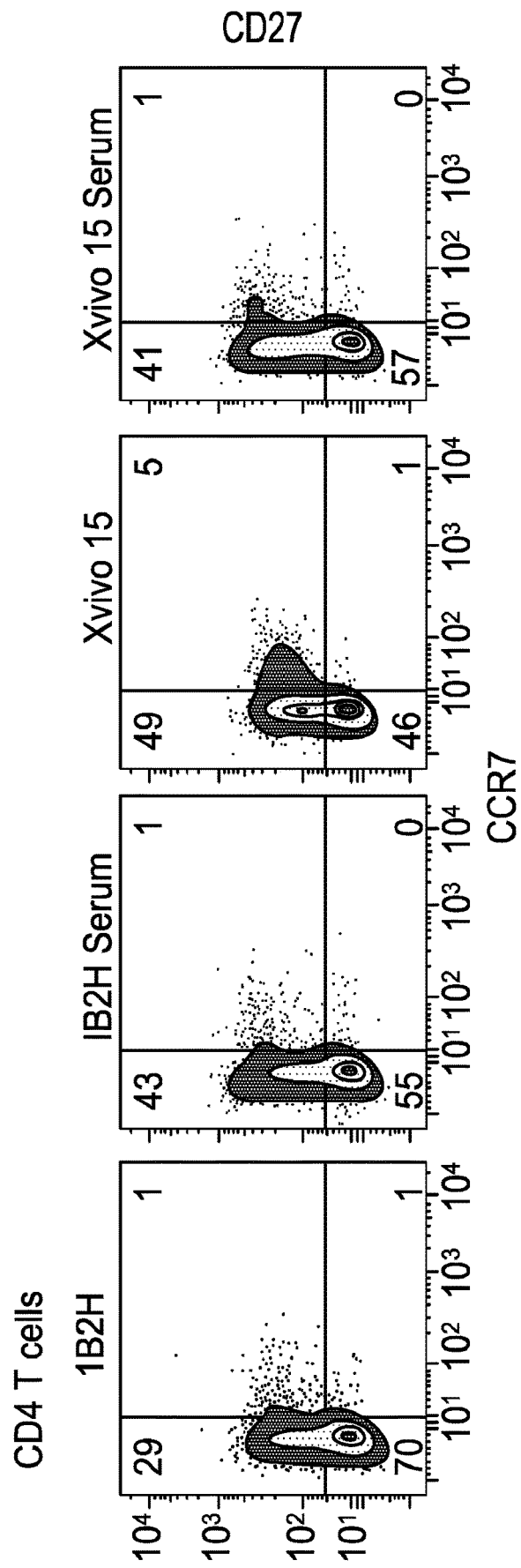
Figure 10D:
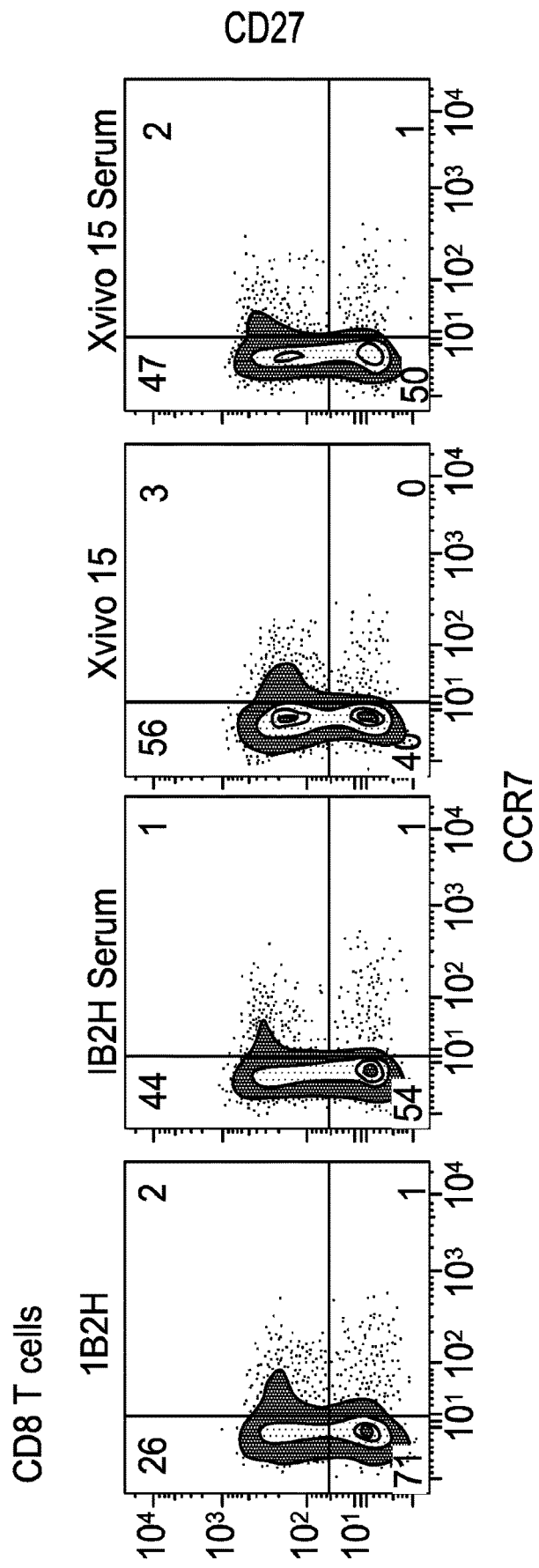
Figure 10E:
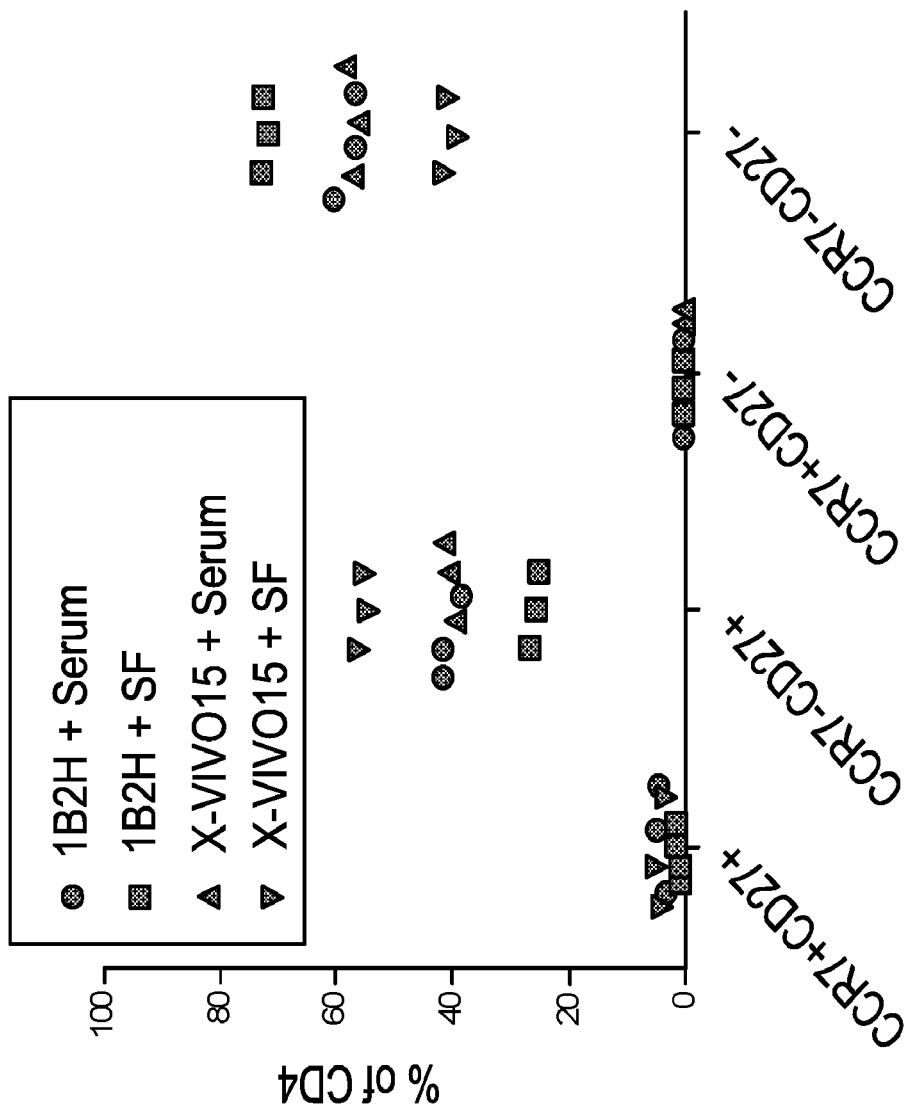
Figure 10F:
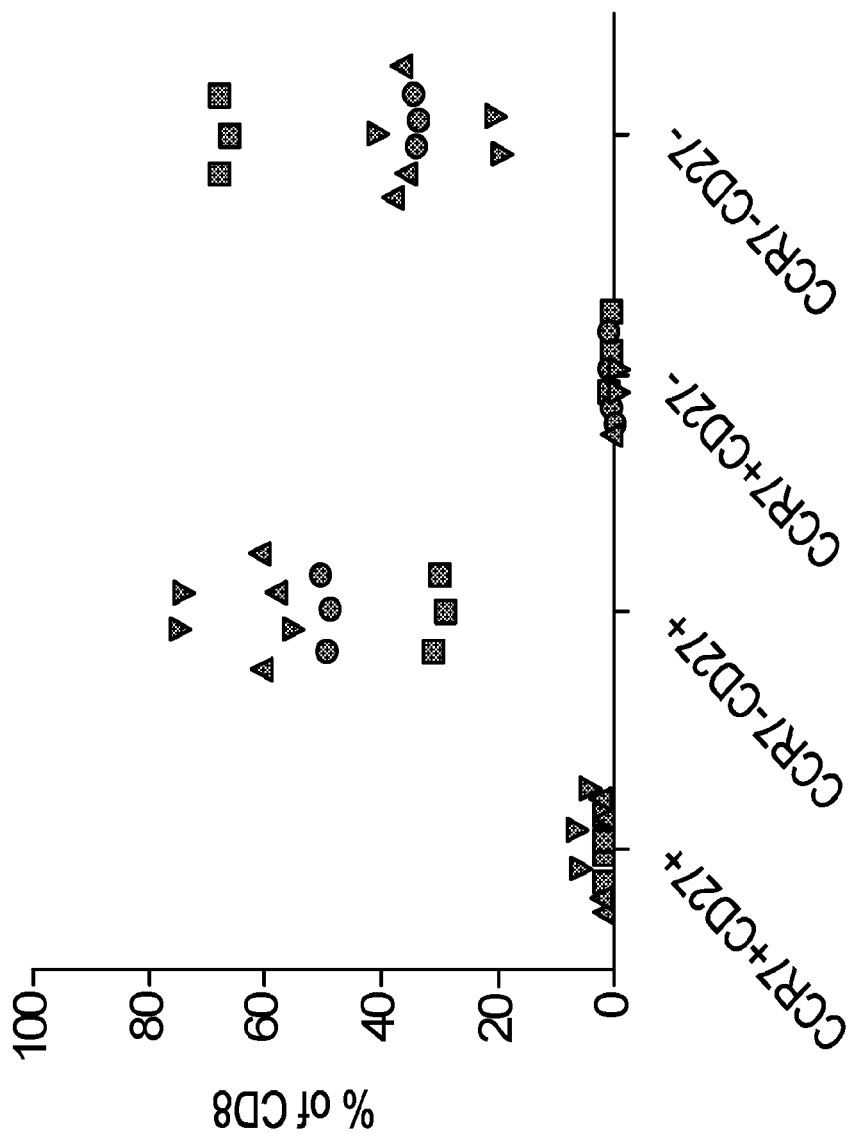
Figure 11C:
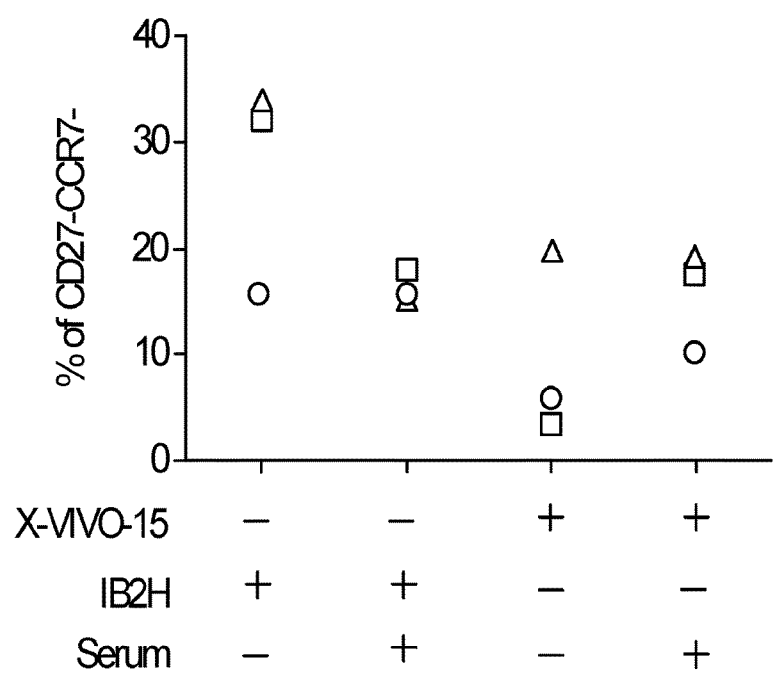
Figure 11E:
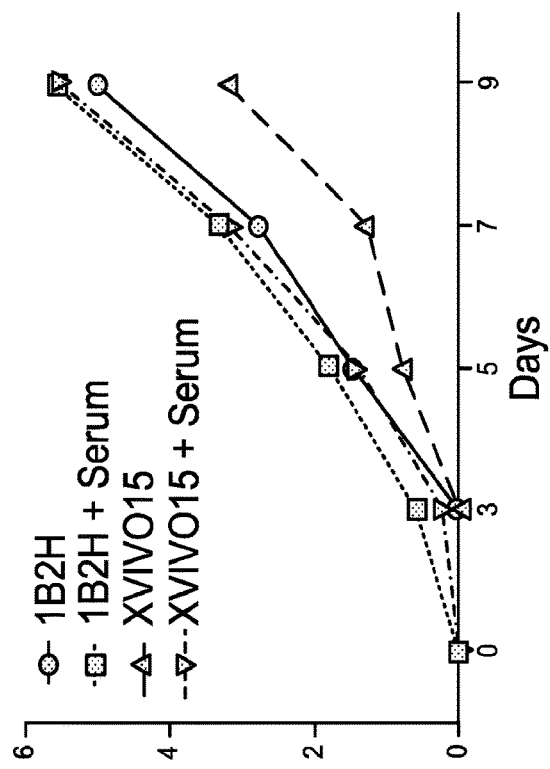
Figure 11D:
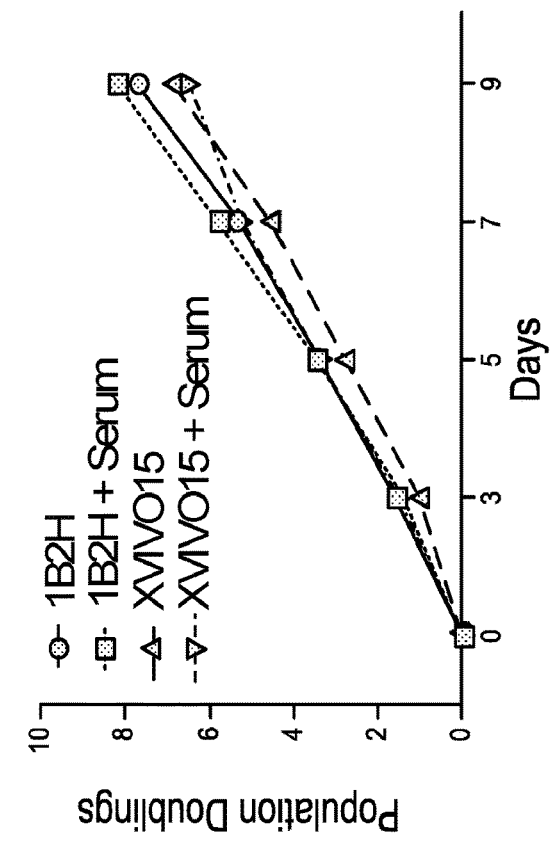
Figure 11F:
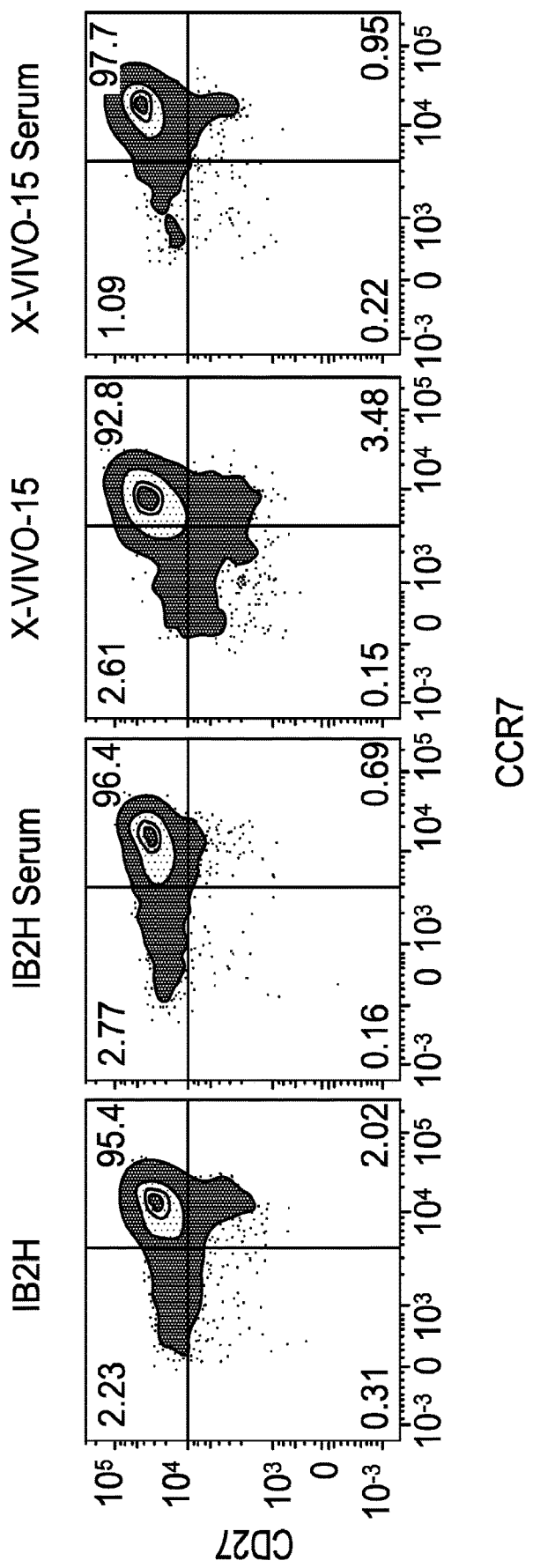
Figure 11G:
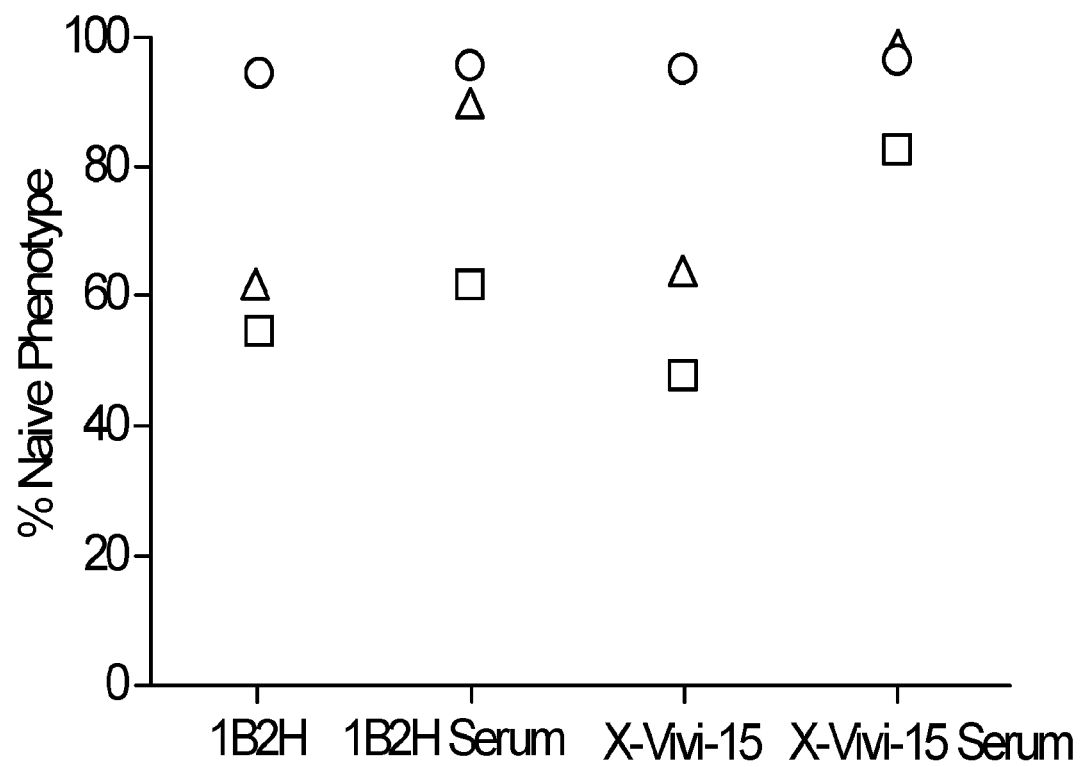
Figure 11H:
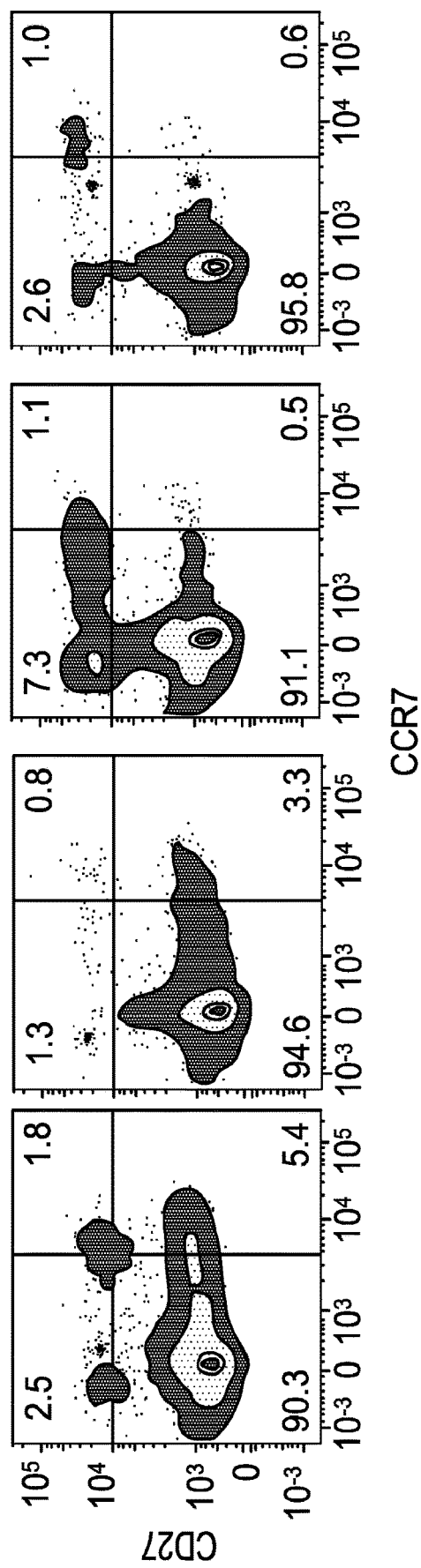
Figure 11I:
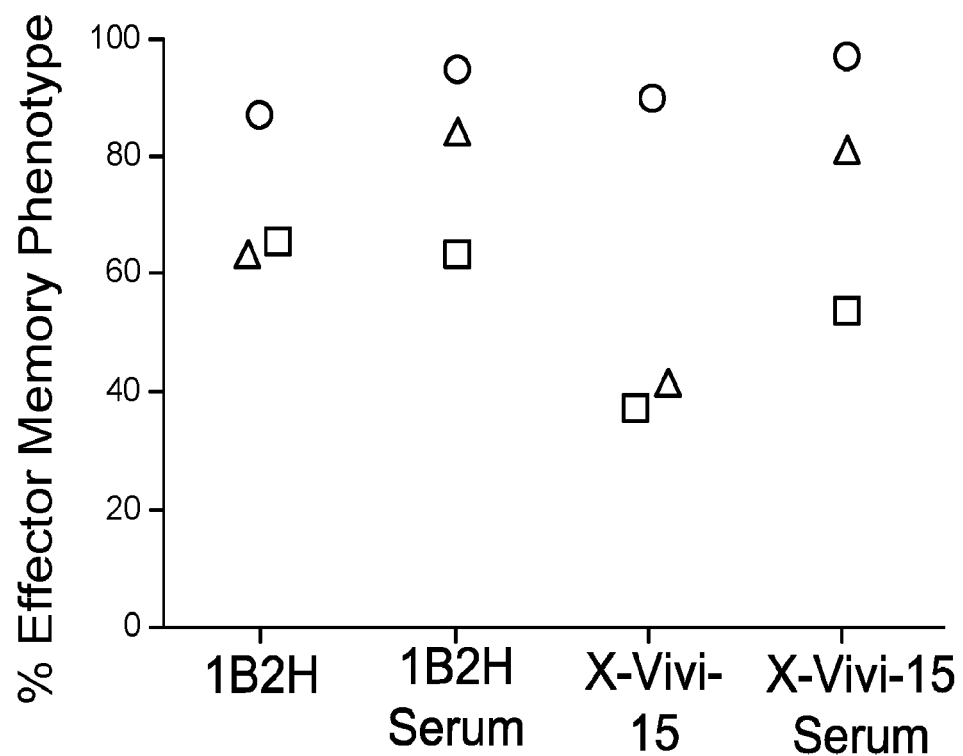

Example 6. Serum Free Media Supports the Expansion of a More Differentiated T Cell Phenotype The phenotype of T cells at the end of culture was also examined. There were a higher percentage of effector memory T cells (CCR7−, CD27−) in T cell cultures expanded using 1B2H (serum free media) than when compared with cultures expanded using X-Vivo™ 15 medium (FIG. 10A-FIG. 10C). In one embodiment, 1B2H is more effective at expanding highly differentiated T cells than other media. In another embodiment, less differentiated (naïve) T cells expanded in 1B2H (serum free media) more rapidly convert into effector T cells than other media. To distinguish between these possibilities, naïve and effector memory T cells were sorted and expanded in either 1B2H or X-Vivo™ 15 in the presence or absence of human serum (FIG. 10D-FIG. 10E). Naïve T cells expanded well in all conditions, though those expanded in 1B2H had one extra population doubling after 9 days of culture. In contrast, there was a drastic difference (~3 population doublings, 8 fold) between effector memory T cells expanded in 1B2H relative to the same T cells expanded in X-Vivo™ 15. The phenotype of T cells after expansion was also examined. While there was some heterogeneity among the naïve T cells from different donors to maintain a naïve phenotype after T cell expansion, these results described herein revealed that the type of media used to expand naïve T cells did not influence the ability of a naïve T cell population to retain its naïve phenotype (FIG. 10F-FIG. 10G). However, T cells expanded in 1B2H maintained T cell effector cell phenotype better than T cells expanded in X-Vivo™ 15 (2 out of 3 donors, FIG. 10H-FIG. 10I). In both cases, the addition of serum did aid the ability of T cells to maintain their original phenotype regardless of whether the T cells were purified to be naïve or effector memory. Together, these results indicate that 1B2H (serum free media) aids the ability of effector memory T cells to expand in culture and 1B2H also aids the ability of effector memory T cells to maintain their effector memory phenotype in culture.

Example 7. T Cells from Multiple Myeloma Patients Expand Better in 1B2H (Serum Free Media)

In some embodiments, T cells from cancer patients are more differentiated and more difficult to expand than T cells from healthy donors. As described herein, 1B2H expanded differentiated T cells better than X-Vivo™ 15. Next, the ability of 1B2H to more efficiently expand highly differentiated T cells isolated from multiple myeloma patients was determined. T cell expansion studies were repeated using cryopreserved, de-identified apheresis products from multiple myeloma patients involved in a previous adoptive T cell therapy clinical trial. X-Vivo™ 15 supplemented with human serum expanded patient T cells better than T cells expanded in X-Vivo™ 15 SFM. This difference was not seen in T cells expanded using 1B2H (FIG. 11A, FIG. 11B), indicating that 1B2H is a SFM for both healthy and patient T cells. Similar to the healthy donors (FIG. 10A-FIG. 10F), 1B2H supported the expansion of highly differentiate T cells with ~70% of the T cells having CCR7−, CD27− phenotype (FIG. 11C-FIG. 11F). These data suggest that the ability of 1B2H to expand patient T cells equally well in the presence and absence of serum is linked to its ability to expand T cells with a highly differentiated phenotype.

Figure 12A:
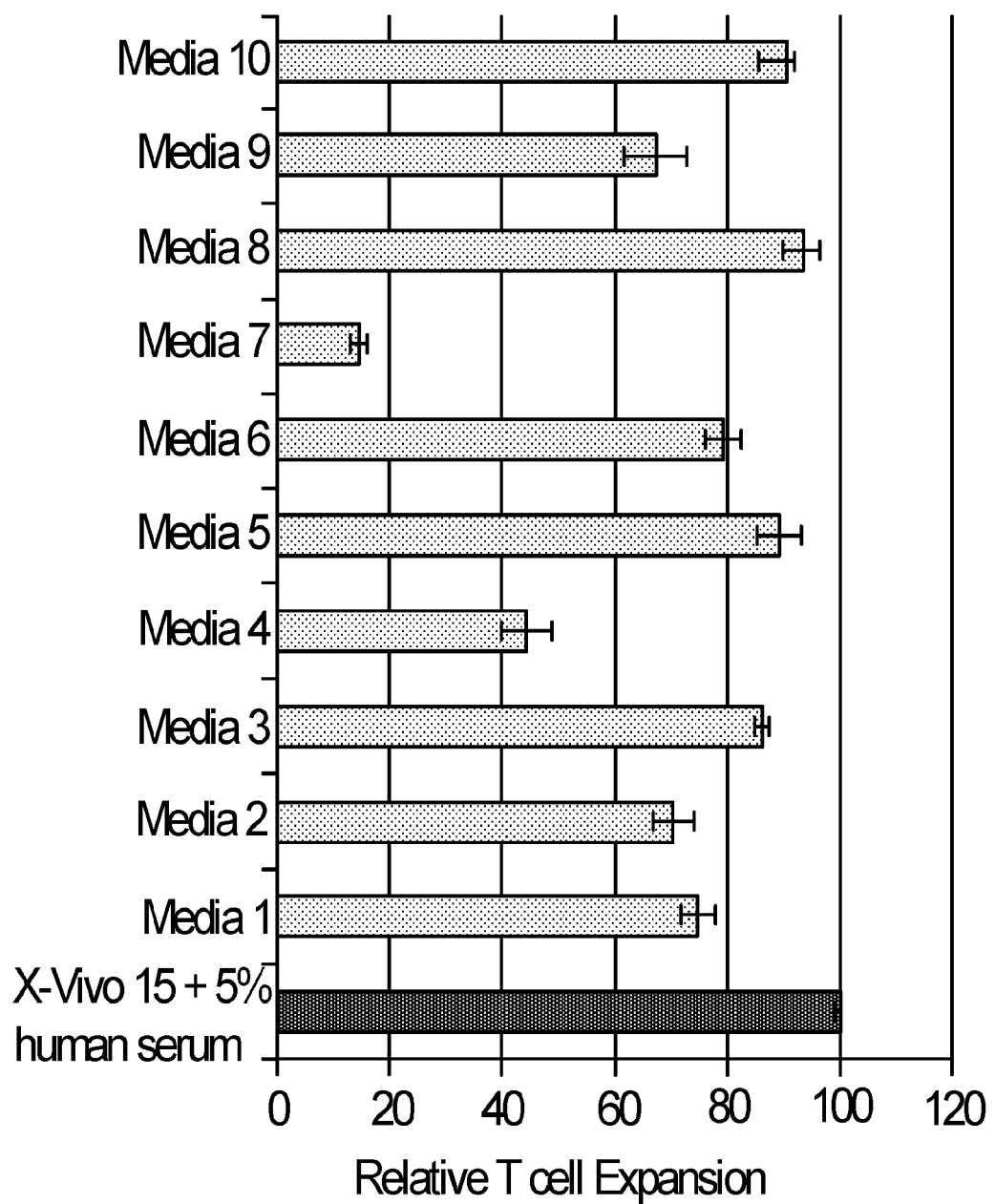
FIG. 12A-FIG. 12F is a series of graphs demonstrating that improved media formulation of 1B2H resulted in greater patient T cell function.
Figure 12B:
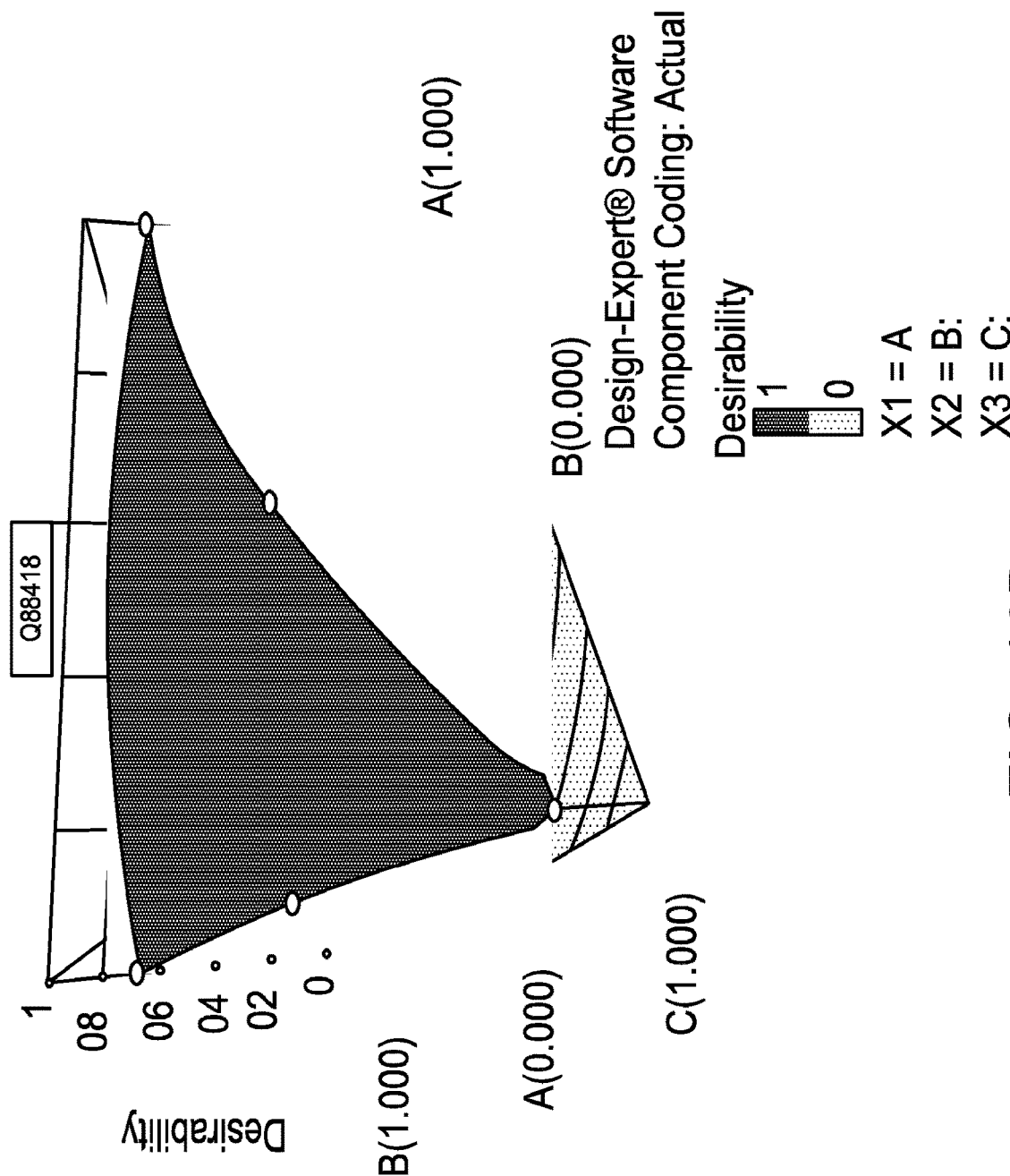
Figure 12D:
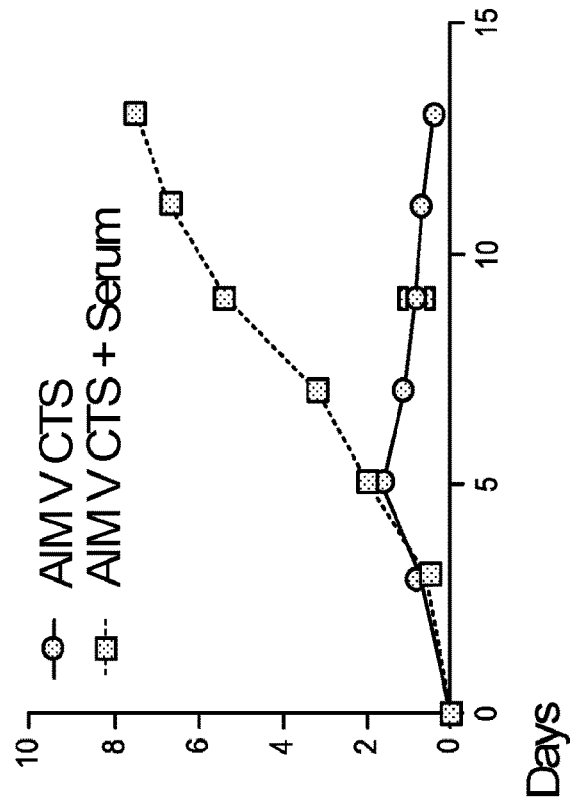
Figure 12C:
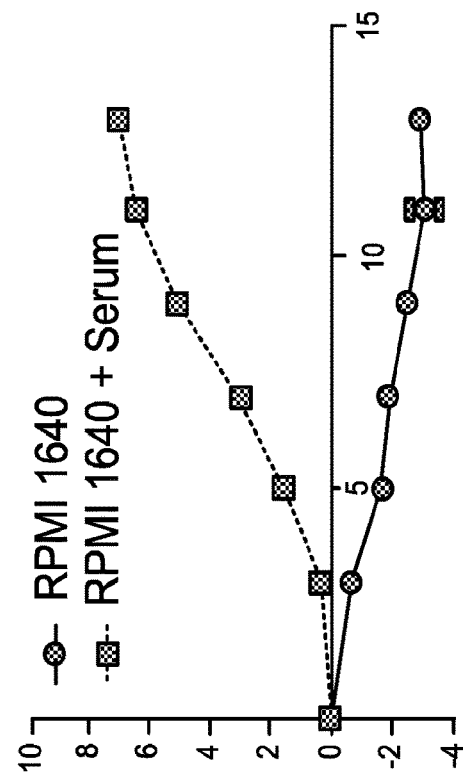
Figure 12F:
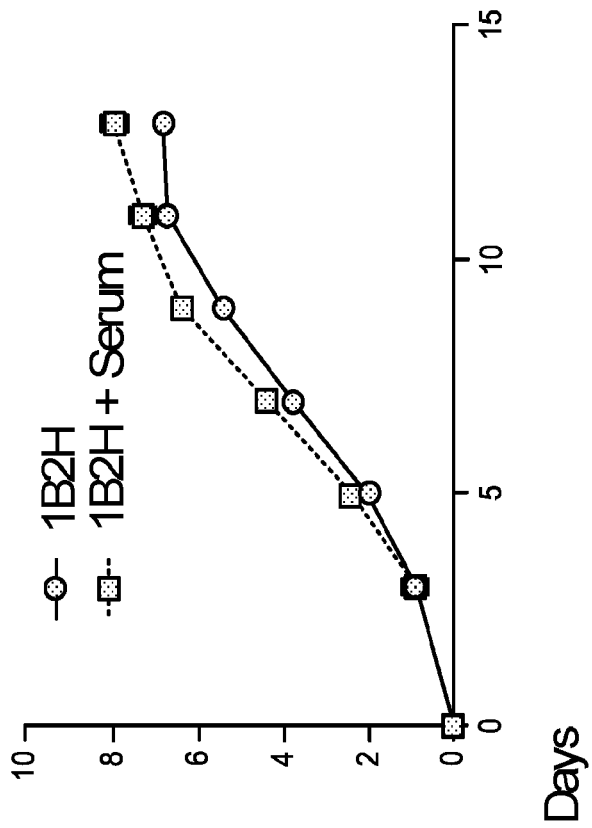
Figure 12E:
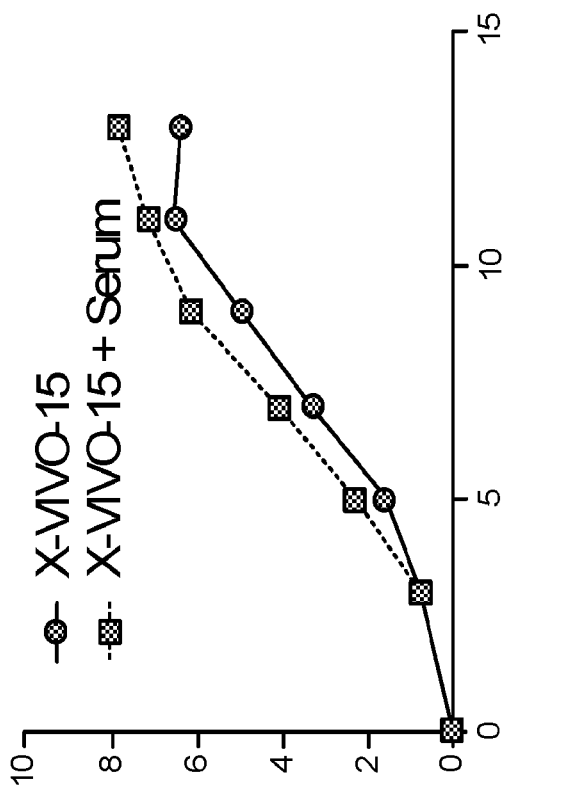
Figure 13B:
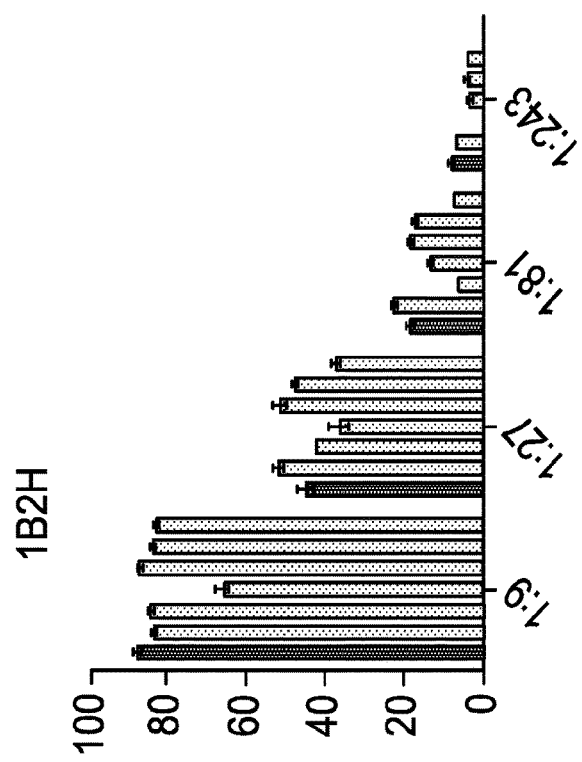
FIG. 13A-FIG. 13E is a series of graphs demonstrating that improved media formulation of 1B2H serum free media resulted in improved CD19 CAR T cells compared to X-VIVO 15 media.
Figure 13A:
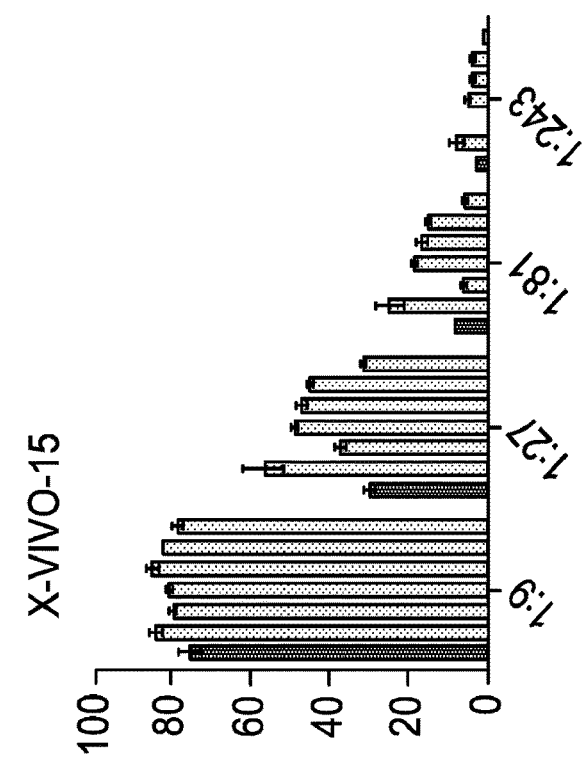
Figure 13C:
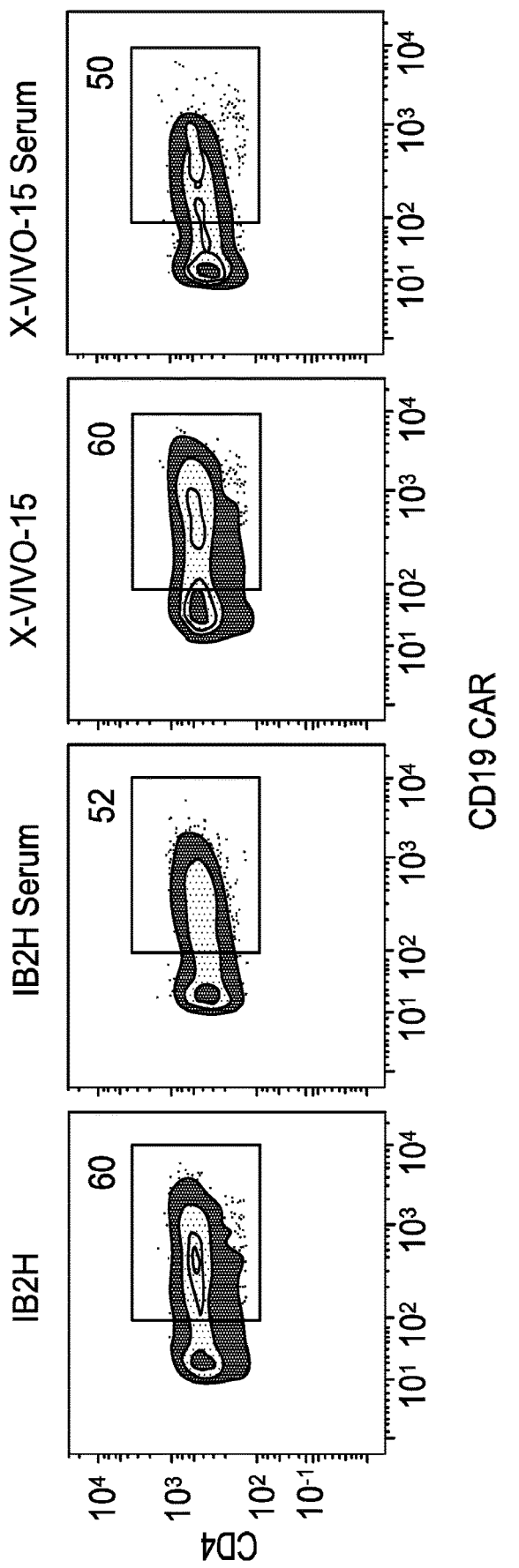
Figure 13D:
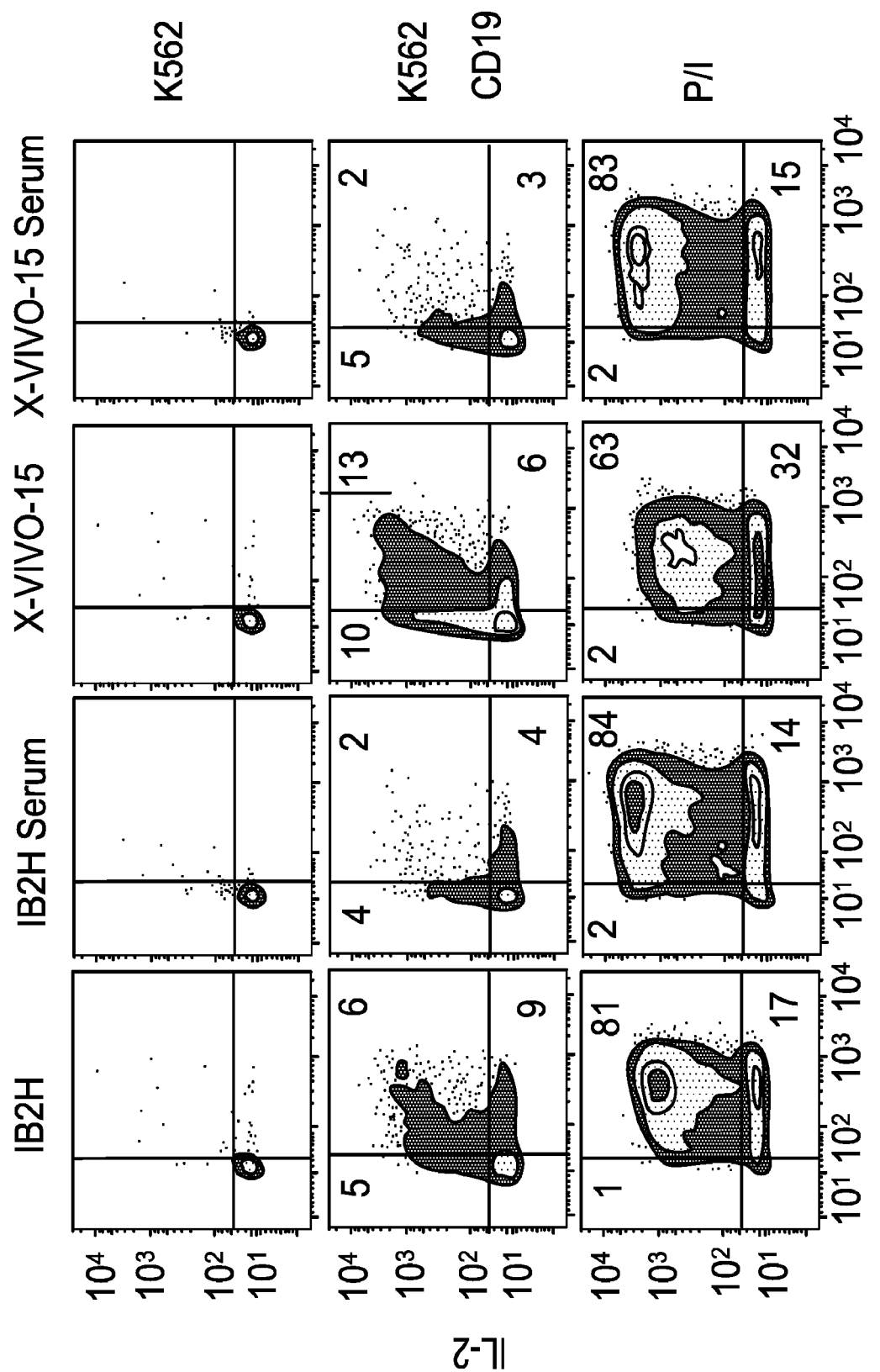
Figure 13E:
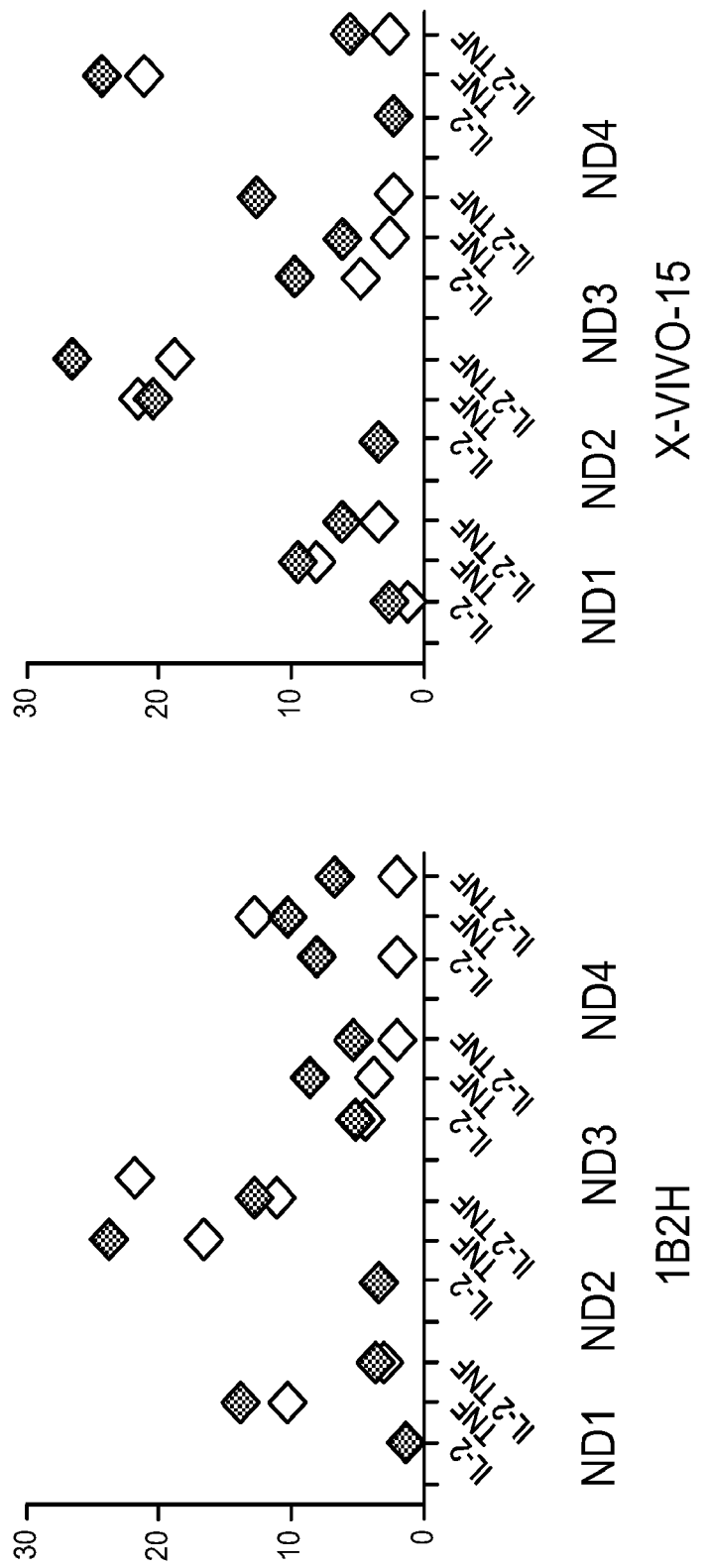
Figure 14:
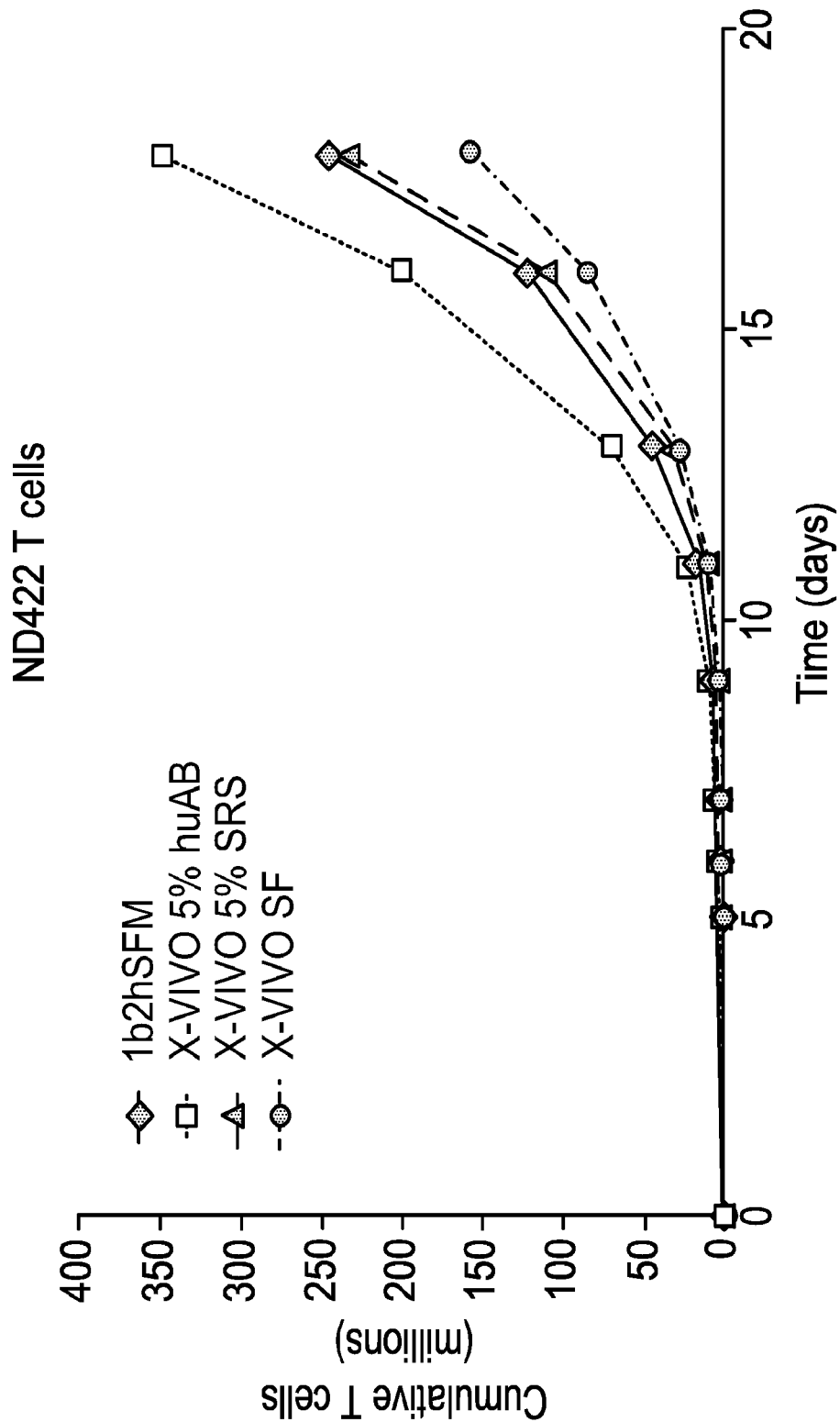
FIG. 14 is a graph depicting 1B2H serum free media shows near equivalent expansion of T cells compared to X-VIVO-15 with serum.
Figure 15:
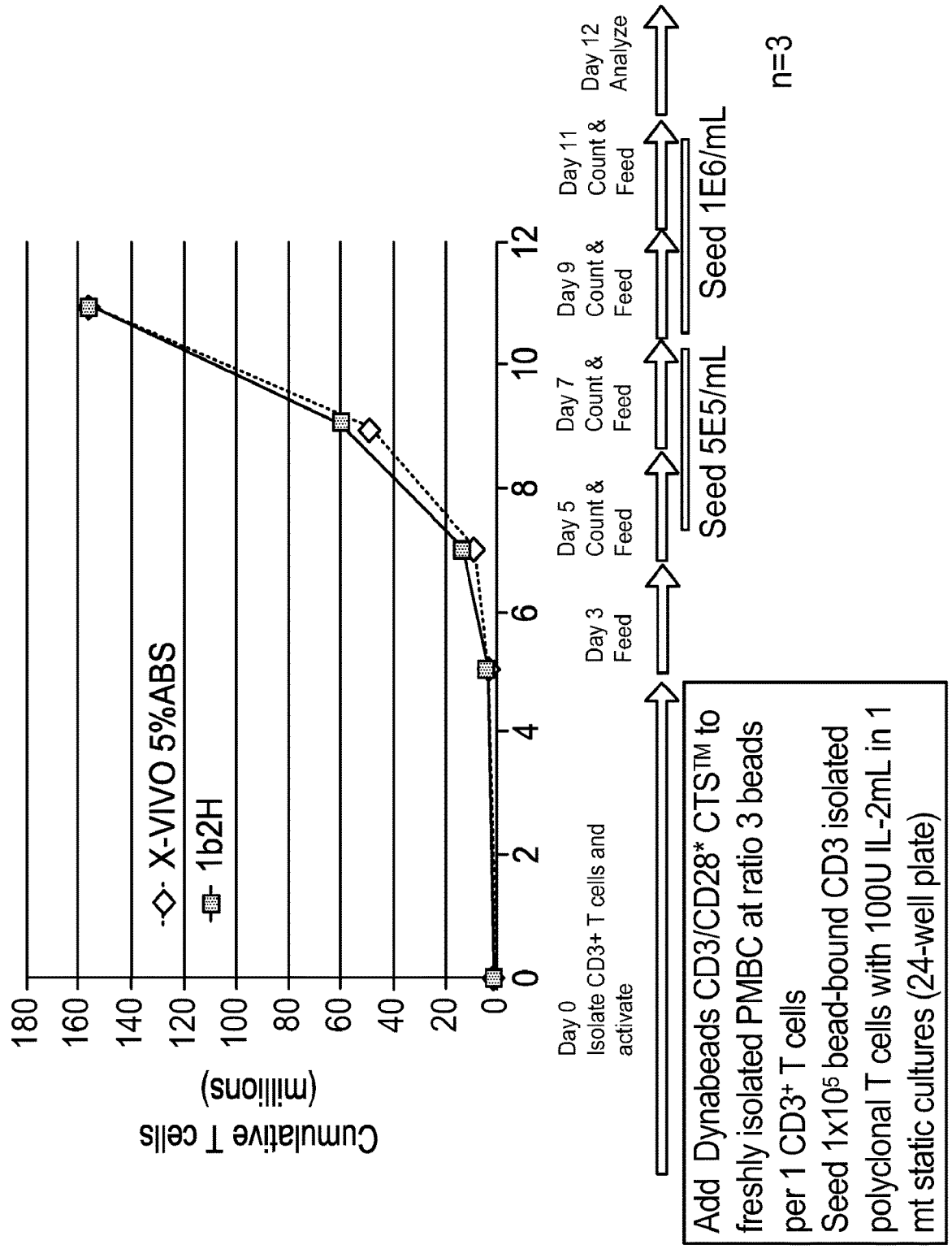
FIG. 15 is a graph demonstrating that serum free media achieves comparable T cell expansion to X-VIVO-15 5% huAB serum.

Example 8. Durable Control of Tumor Growth of Patient T Cells Expanded with 1B2H The functional properties of the multiple myeloma patient T cells expanded in X-Vivo™ 15 or 1B2H with and without serum were examined. Here, the addition of serum did not significantly alter the functional profile of the expanded CD19-specific CAR T cells and there were no consistent differences between T cells grown in 1B2H or X-Vivo™ 15 (FIG. 12A, FIG. 12B), suggesting the functional abilities of fully differentiated T cells are not modulated by the presence of human serum or media in which they are expanded. The ability of these expanded T cells to control tumors was examined.

Example 9. Serum Free Media Shows Near Equivalent Expansion of T Cells Compared to X-VIVO-15 with Serum As demonstrated in FIG. 14 and FIG. 15, 1B2H serum free media shows near equivalent expansion of T cells compared to X-VIVO-15 with serum. Serum free media with glucose:galactose and lipids achieves comparable T cell expansion to X-VIVO-15 5% huAB serum.

Figure 16:
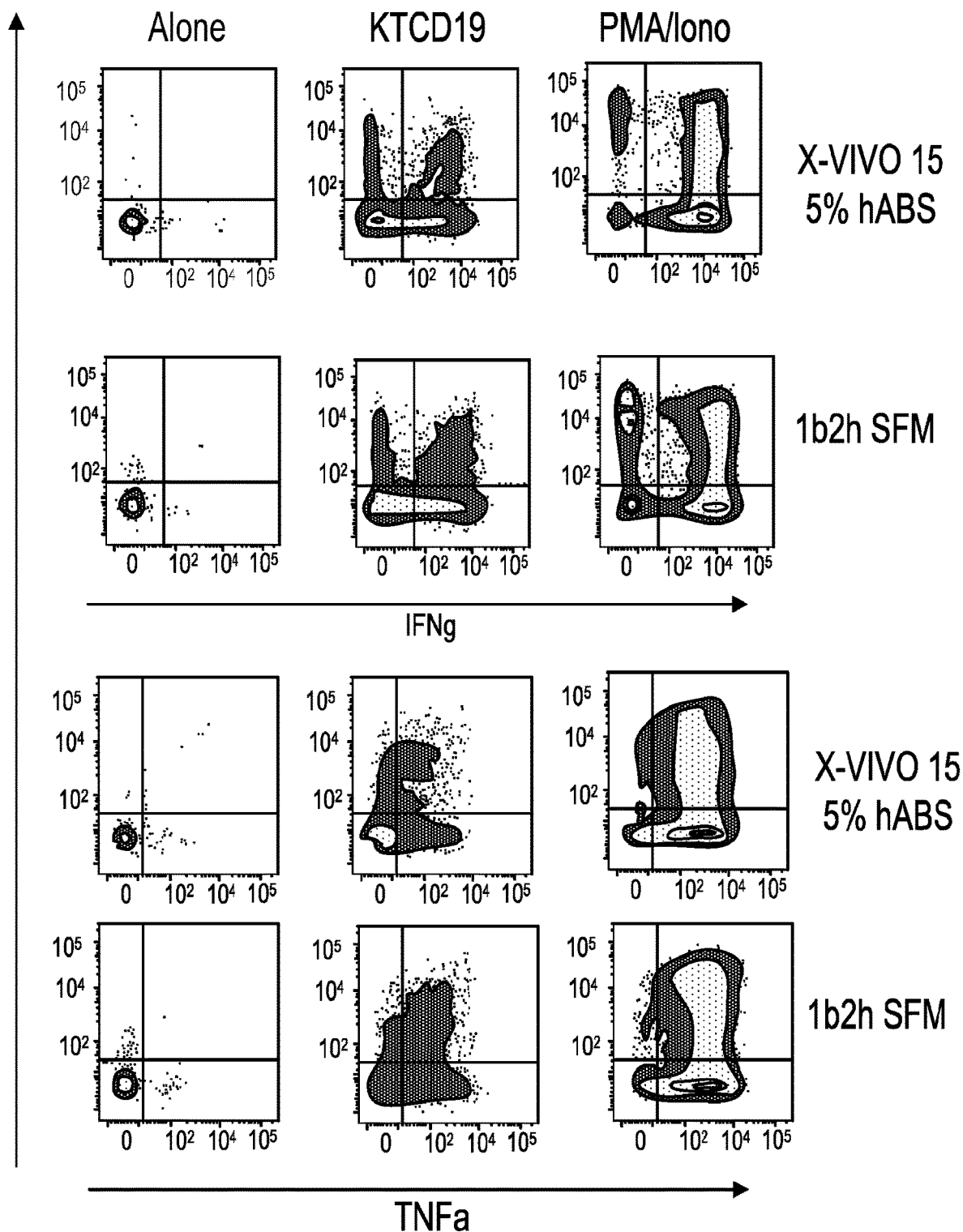
FIG. 16 is a series of graphs demonstrating that serum-free 1B2H generates more potent CART 19 T cells. Engineered T cells (e.g., chimeric antigen receptor T cells, or CART cells) were cultured in the glucose:galactose serum free media described herein.

Example 10. Serum Free Media with Glucose:Galactose Generates Functional T Cells Serum-free 1B2H generates more potent CART 19 T cells. Engineered T cells (e.g., chimeric antigen receptor T cells, or CART cells) were cultured in the glucose:galactose serum free media described herein (see FIG. 16). CART 19 T cells cultured in glucose:galactose serum free media supplemented with lipids were more potent than those grown in media containing serum.

Figure 17:
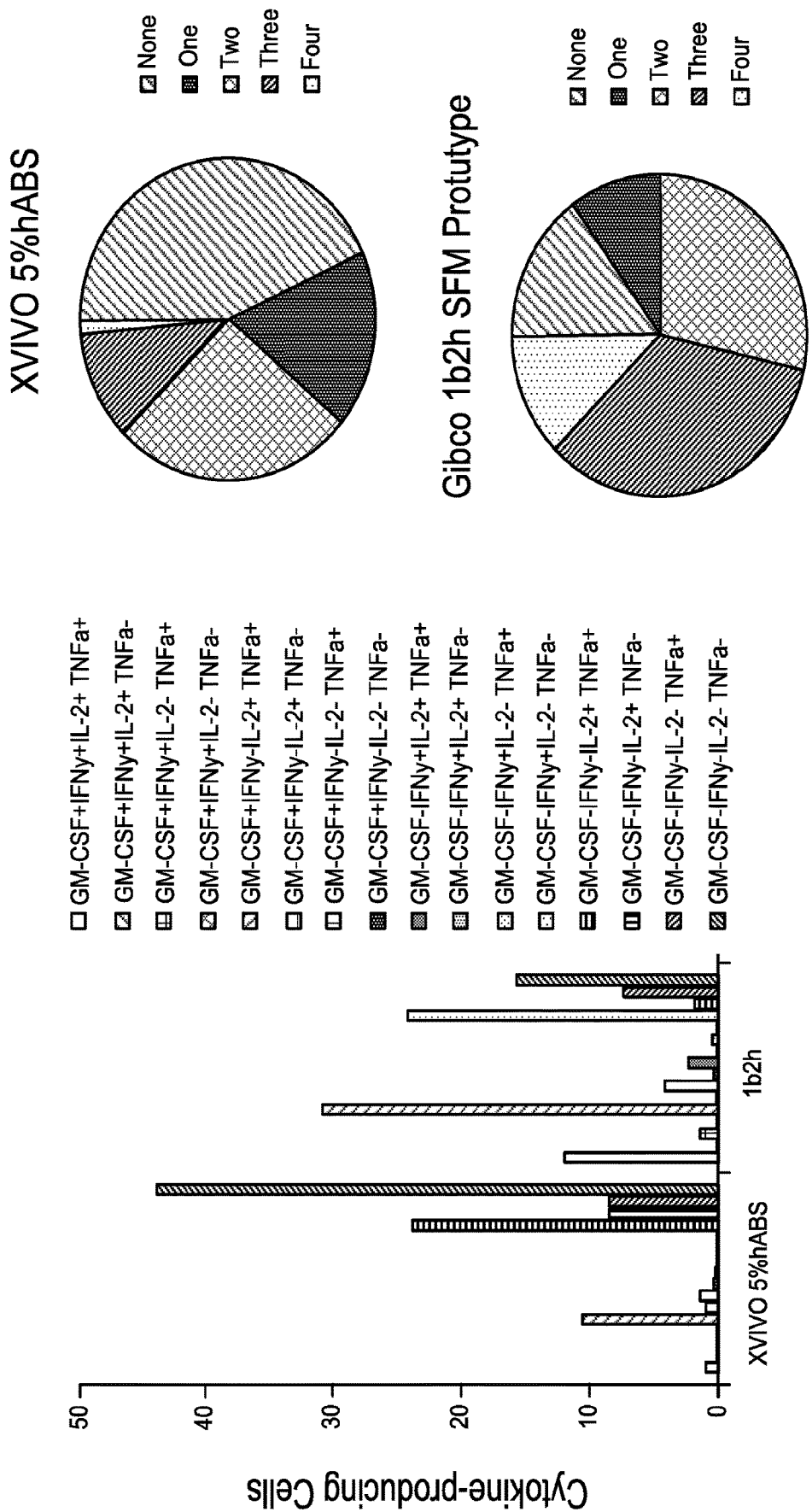
FIG. 17 is a series of graphs demonstrating that 1B2H generates highly functional T cells. T cells grown in X-VIVO 15 with 5% huABS or serum free media and stimulated with PMA and Ionomycin were stained for GM-CSF, IL-2, IFN-γ, and TNF-α. Boolean analysis showed an increased percentage of T cells producing more than one cytokine in serum free media.

T cells grown in X-VIVO 15 with 5% huABS or serum free media and stimulated with PMA and Ionomycin were stained for GM-CSF, IL-2, IFN-γ, and TNF-α. Boolean analysis showed an increased percentage of T cells producing more than one cytokine in serum free media. As depicted in FIG. 17, 1B2H generates highly functional T cells.

Figure 18:
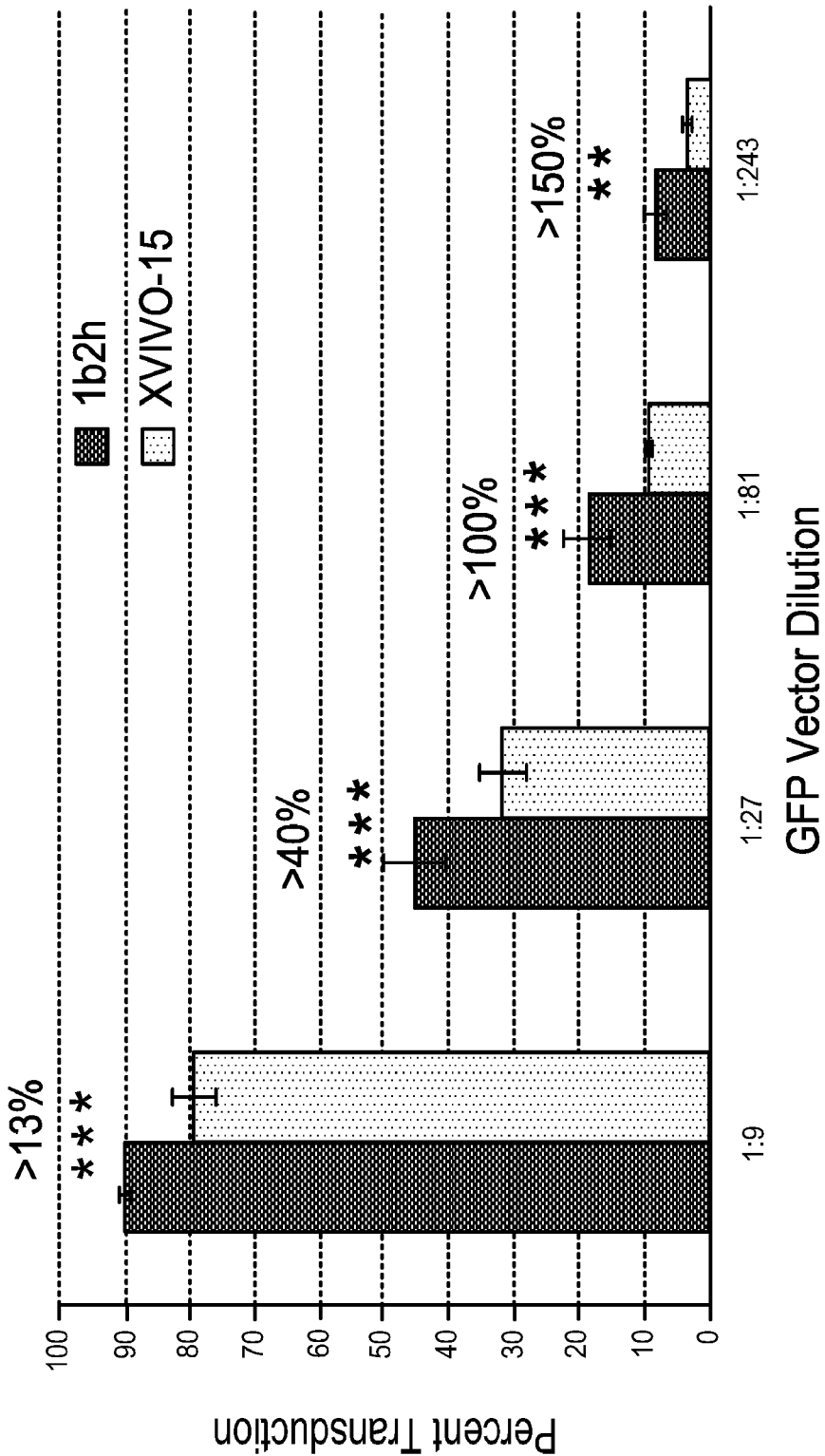
FIG. 18 is a graph demonstrating that serum free media enhances lentiviral transduction at low multiplicities of infection. Triplicate wells of bulk T cells were activated and transduced with GFP vector. Transduction efficiency was analyzed by flow cytometry. In a Student-Newman-Keuls test—*$P<0.001$ and $P<0.01$.

Triplicate wells of bulk T cells were activated and transduced with GFP vector. Transduction efficiency was analyzed by flow cytometry. The Student-Newman-Keuls test was used to analyze the results (*P<0.001 and P<0.01). FIG. 18 demonstrates that serum free media enhances lentiviral transduction at low multiplicities of infection.

Figure 19:
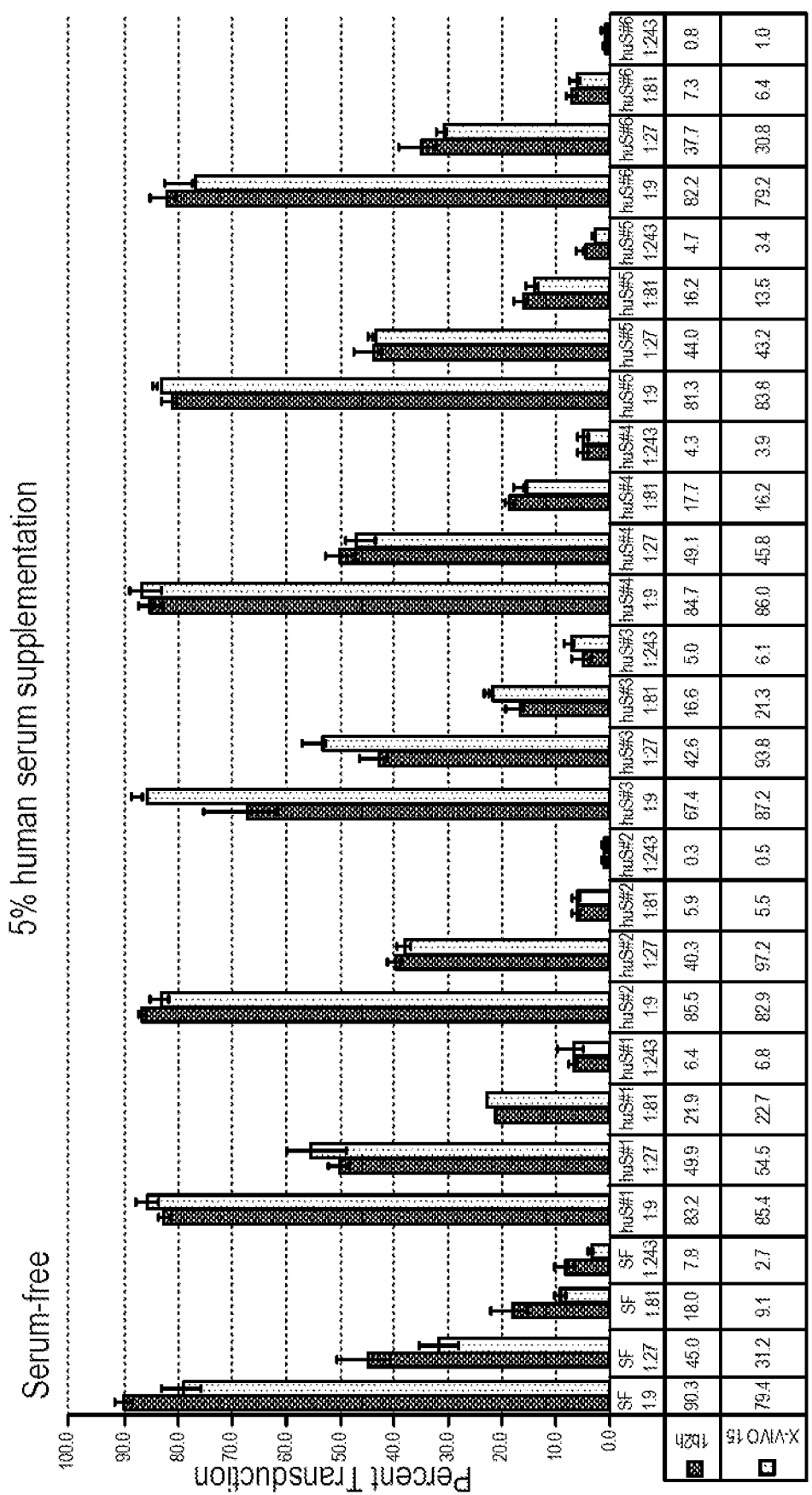
FIG. 19 is a graph demonstrating that serum free media is comparable to X-VIVO when supplemented with 5% human serum. Serum free media and X-VIVO-15 were supplemented with 5% human serum from 6 lots of serum from at least 4 suppliers (pooled human AB and "off-the-clot" serum). Triplicate wells of bulk T cells were activated and transduced with GFP vector. Transduction efficiency was analyzed by flow cytometry.

Serum free media and X-VIVO-15 were supplemented with 5% human serum from 6 lots of serum from at least 4 suppliers (pooled human AB and "off-the-clot" serum). Triplicate wells of bulk T cells were activated and transduced with GFP vector. Transduction efficiency was analyzed by flow cytometry. For carrying out transduction of expanded T cells, FIG. 19 demonstrates that serum free media is comparable to X-VIVO when supplemented with 5% human serum.

Figure 20:
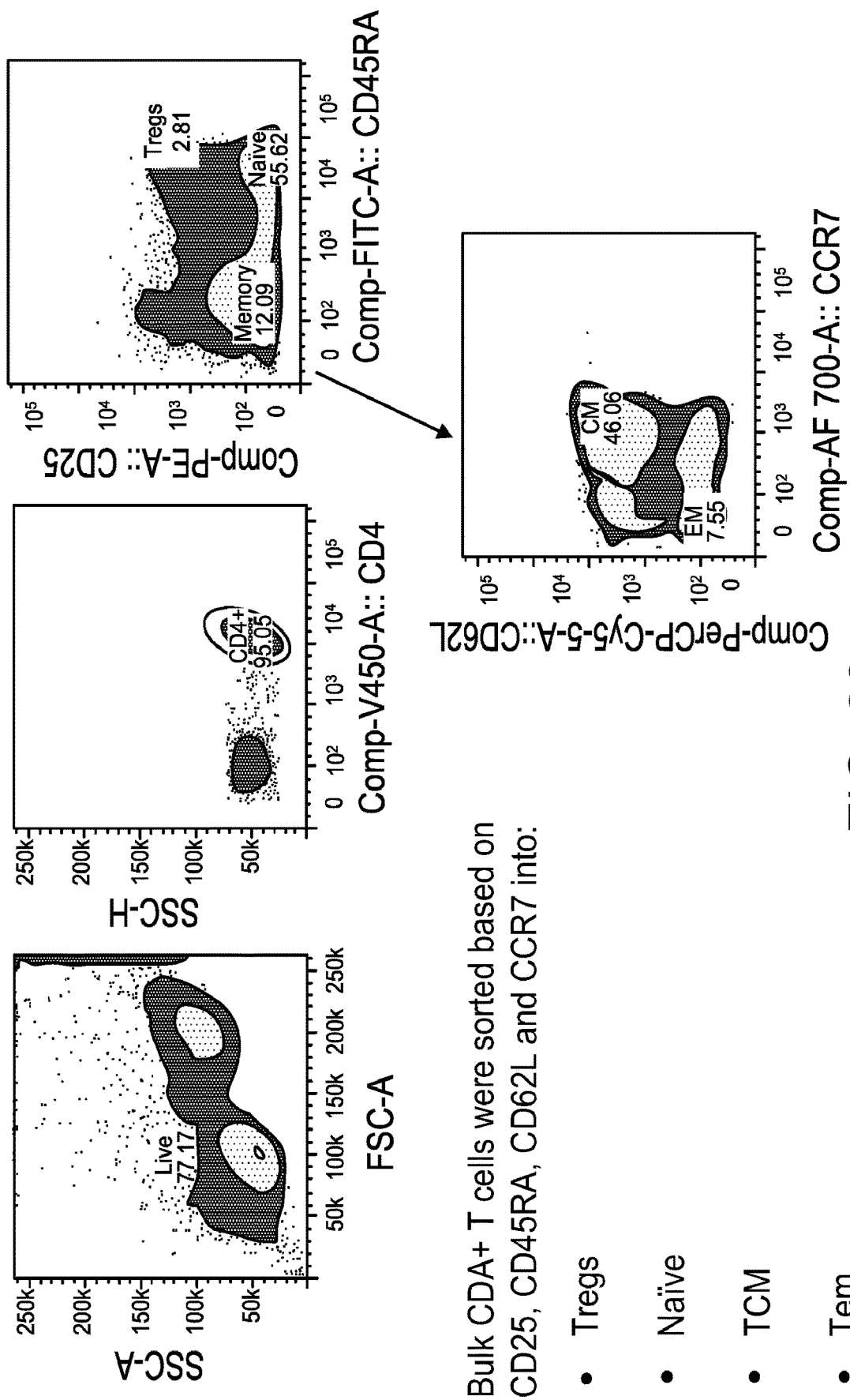
FIG. 20 is a series of FACS gating results depicting the sorting strategy for subset T cell expansion. Bulk CD4+ T cells were sorted into Tregs, Naïve, Tcm (central memory), and Tem (effector memory) subsets based on the markers CD25, CD45RA, CD62L, and CCR7.
Figure 21:
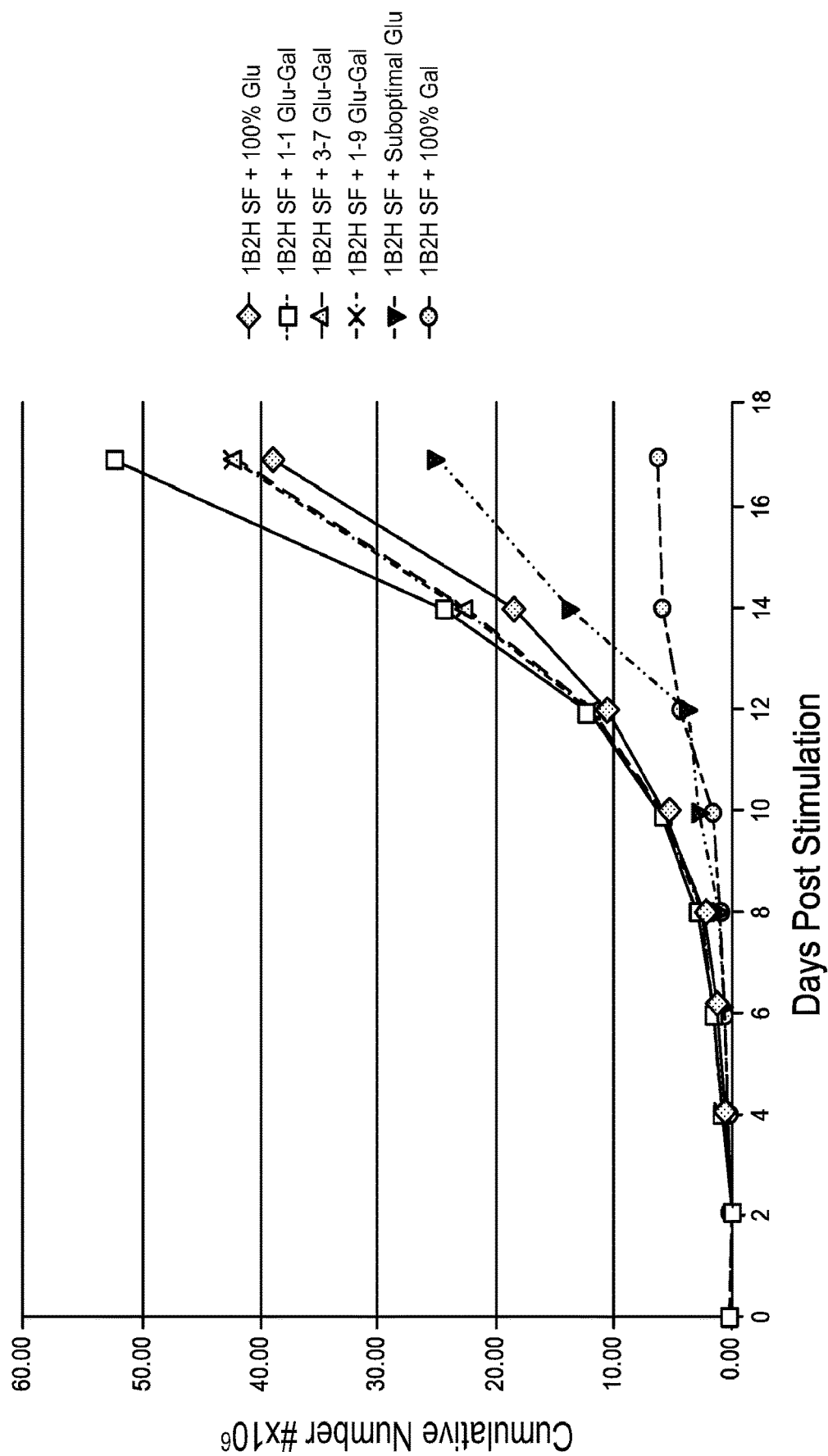
FIG. 21 is a graph demonstrating that galactose promotes a high rate of expansion of naïve T cells in the presence of low glucose.
Figure 22:
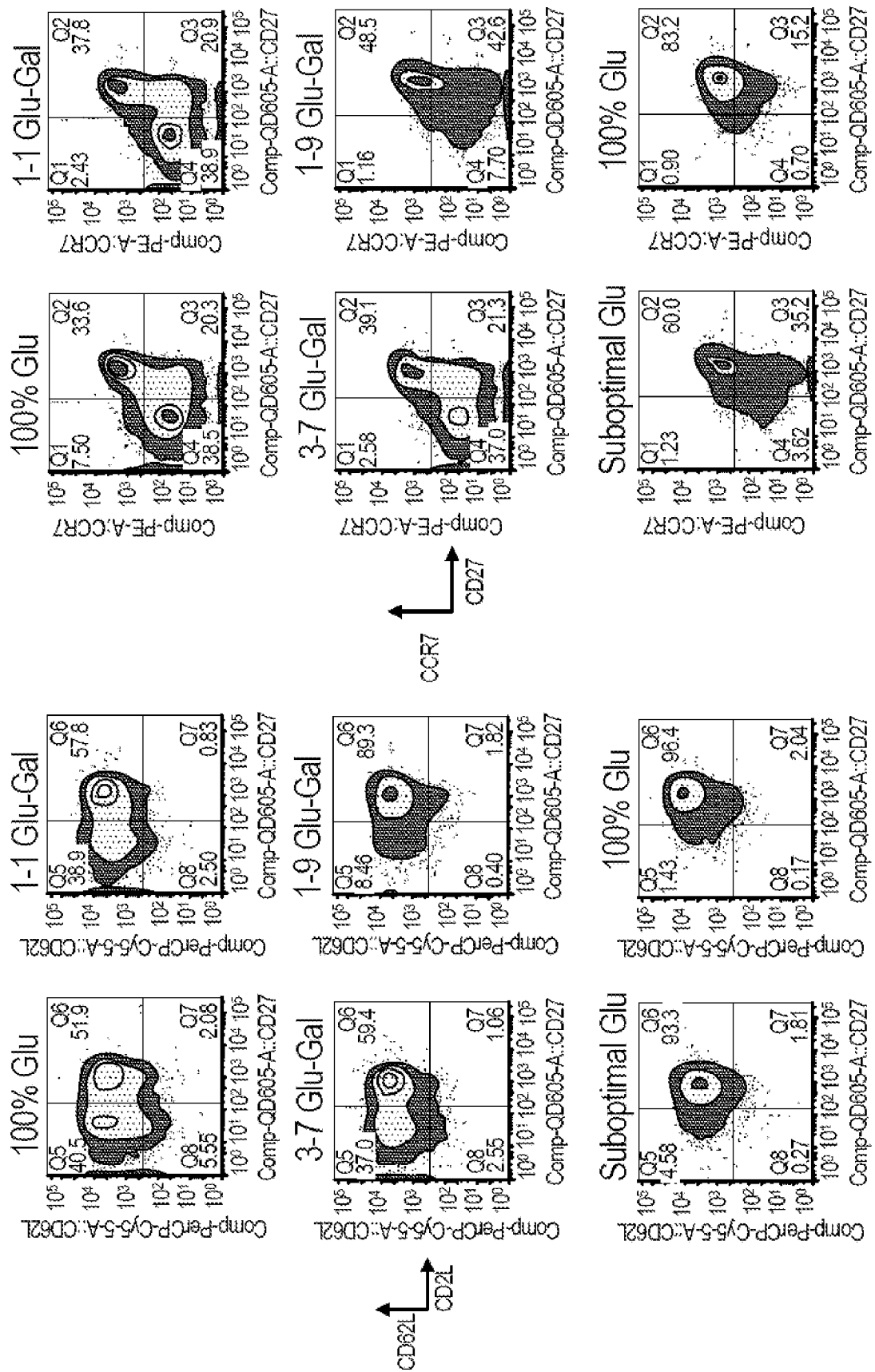
FIG. 22 is a series of FACS gating results demonstrating that expanded naïve CD4+ T cells preserve the naïve phenotype when grown in limited glucose.
Figure 23:
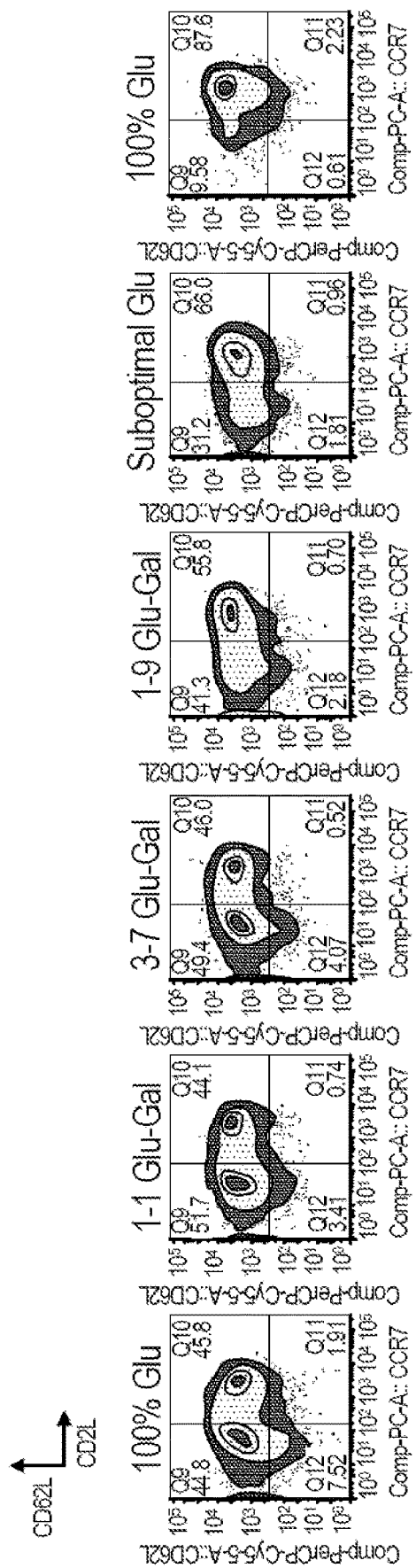
FIG. 23 is a series of FACS gating results demonstrating that expanded naïve CD4+ T cells preserve the naïve phenotype when grown in limited glucose.

Example 11. T Cells of Various Subpopulations were Expanded in Limited Glucose:Galactose Serum Free Media Bulk CD4+ T cells were sorted into Tregs, Naïve, Tcm (central memory), and Tem (effector memory) subsets based on the markers CD25, CD45RA, CD62L, and CCR7. Based on FIG. 20, T cells of different subpopulations may be sorted through use of FACS. According to FIG. 21, galactose allows a high rate of expansion of naïve T cells in the presence of low glucose. Expanded naïve CD4+ T cells preserve the naïve phenotype when grown in limited glucose, as witnessed through FACS analysis (see FIG. 22 and FIG. 23).

Example 12. Effects of 1:1 Glucose:Galactose Media on IFNγ Production and T Cell Expansion While good expansion of T cells can be achieved in media containing multiple ratios of glucose and galactose, ratios with limiting glucose can have a negative impact in interferon gamma production. There is evidence that interferon-gamma expression is regulated via GAPDH in T-cells (Chang, et al Cell. 2013 June 6; 153(6): 1239-1251) thus excessively limiting glycolysis during T cell expansion can impair IFN-γ production. The 1:1 glucose/galactose ratio maintains IFN-γ production in naïve T cells while improving T cell expansion. Central memory T cells appear not to be effected by glucose level. This demonstrates that naïve T cells could be expanded in limiting glucose media to drive development of T cell subsets that do not require IFN-γ for their function (e.g. Tregs, Th9, others). Primary human CD4+ T cells from normal donors isolated via negative selection were obtained from UPenn Human Immunology Core Facility. Cells were separated by flow cytometric sorting into Naïve (CD45RA+/CD27+/CCR7+), and Central Memory (CD45RA−/CD27+/CCR7+), subsets. T cells (seeding density 1×106/mL) were activated with DYNABEADS® Human T-Expander CD3/CD28 at a ratio of 3 beads per T cell and cultured in serum-free medium supplemented with G$_{IBCO}$™ Chemically Defined Lipid Concentrate (1:100) and either d-glucose, d-galactose or mixtures of glucose and galactose as indicated; final concentration of sugar was 6 g/L in all conditions, except a suboptimal condition with 0.6 g/L glucose. T cells were fed and counted on days 5, 7, 10 and 12 on a Beckman-Coulter Multisizer 3. Expanded T cells were activated at day 12 post-expansion for five hours with 12-O-tetradecanoyl phorbol-13-acetate (PMA), and a Ca2+ ionophore (ionomycin) in the precesence of Brefeldin-A. Intracellular cytokine staining was performed with antibodies against interferon-gamma and IL-2.

Figure 24:
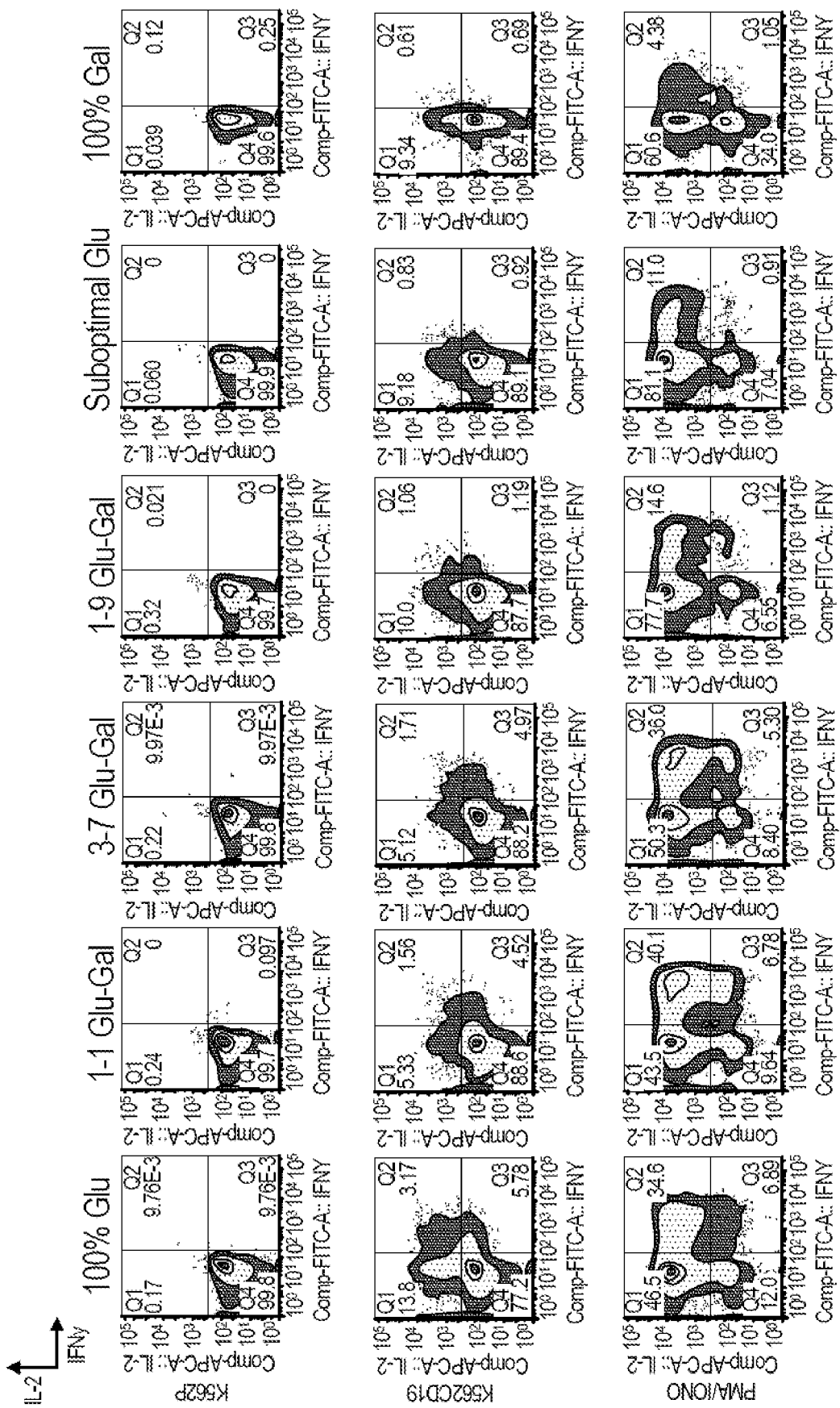
FIG. 24 is a series of FACS gating results demonstrating the loss of IFNγ production in naïve CD4+ T cells grown in limited glucose media.
Figure 25:
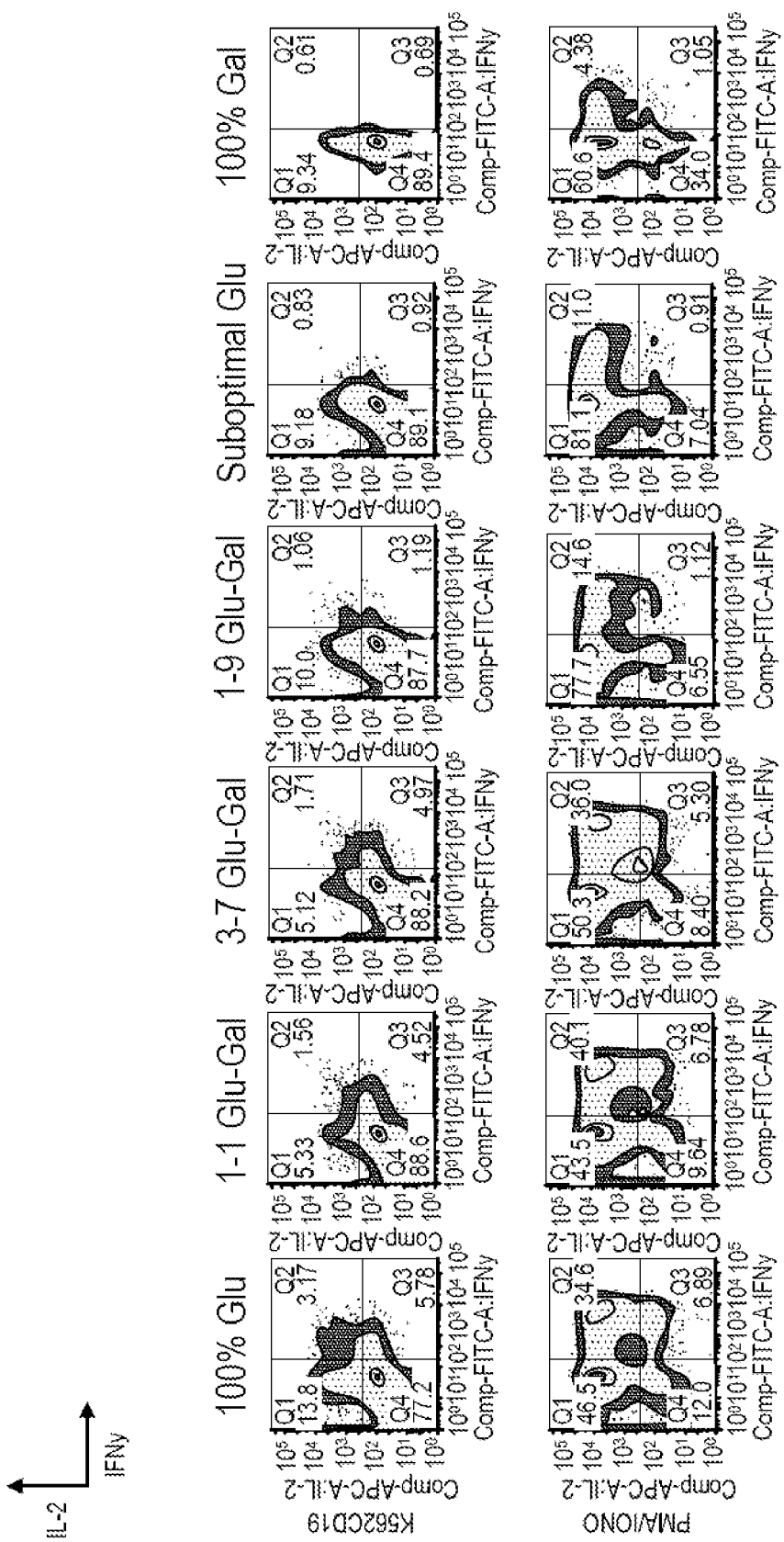
FIG. 25 is a series of FACS gating results demonstrating the loss of IFNγ production in naïve CD4+ T cells grown in limited glucose:galactose media.
Figure 26:
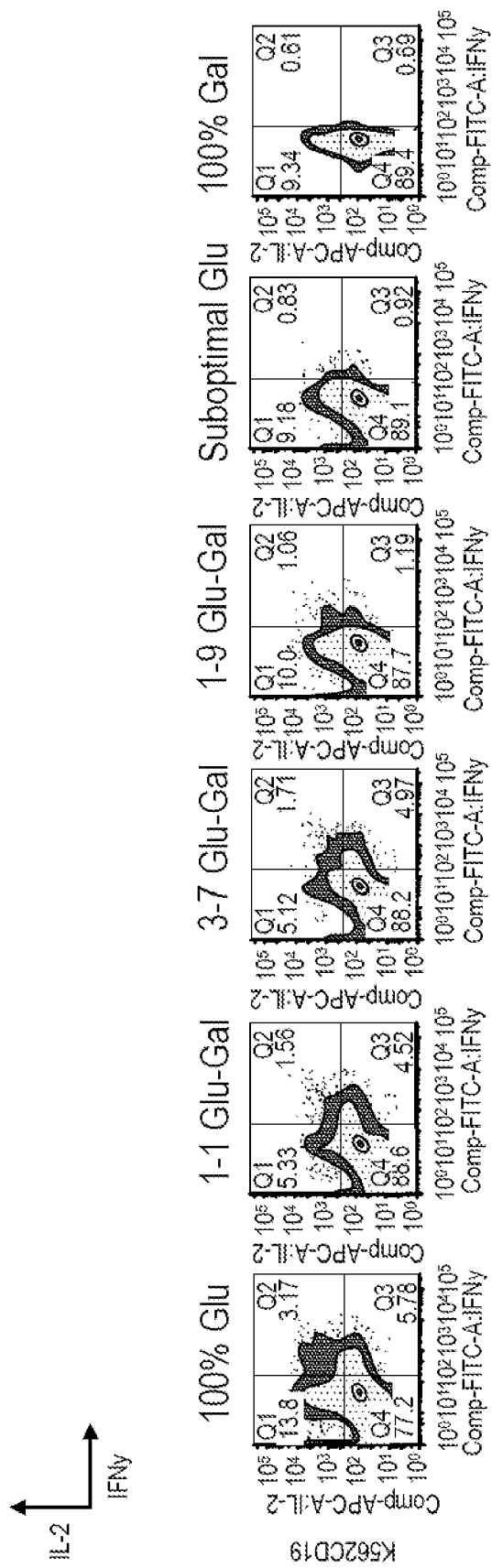
FIG. 26 is a series of FACS gating results demonstrating the loss of IFNγ production in naïve CD4+ T cells grown in limited glucose:galactose media.
Figure 27:
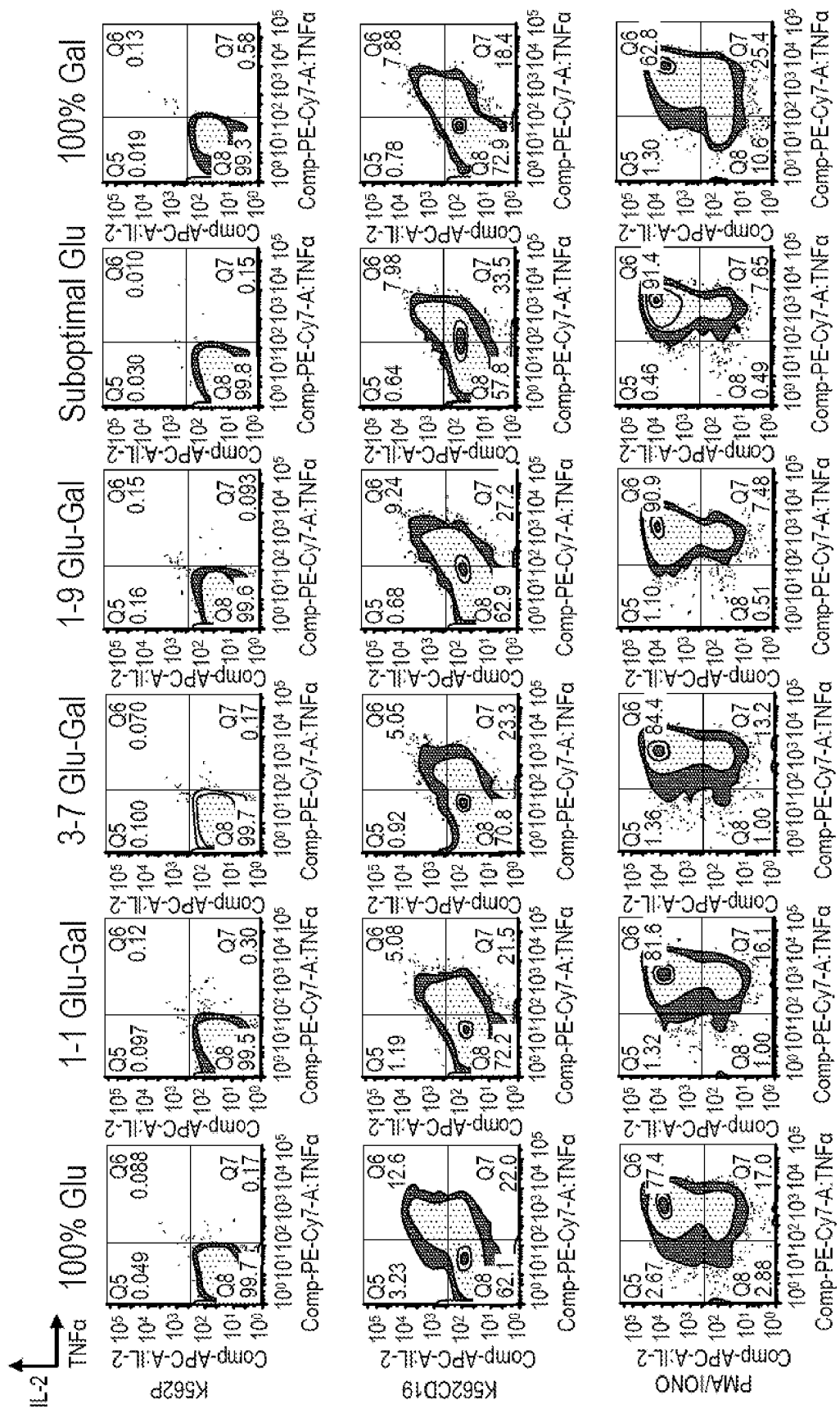
FIG. 27 is a series of FACS gating results demonstrating comparable cytokine production in naïve CD4+ T cell conditions.
Figure 28:
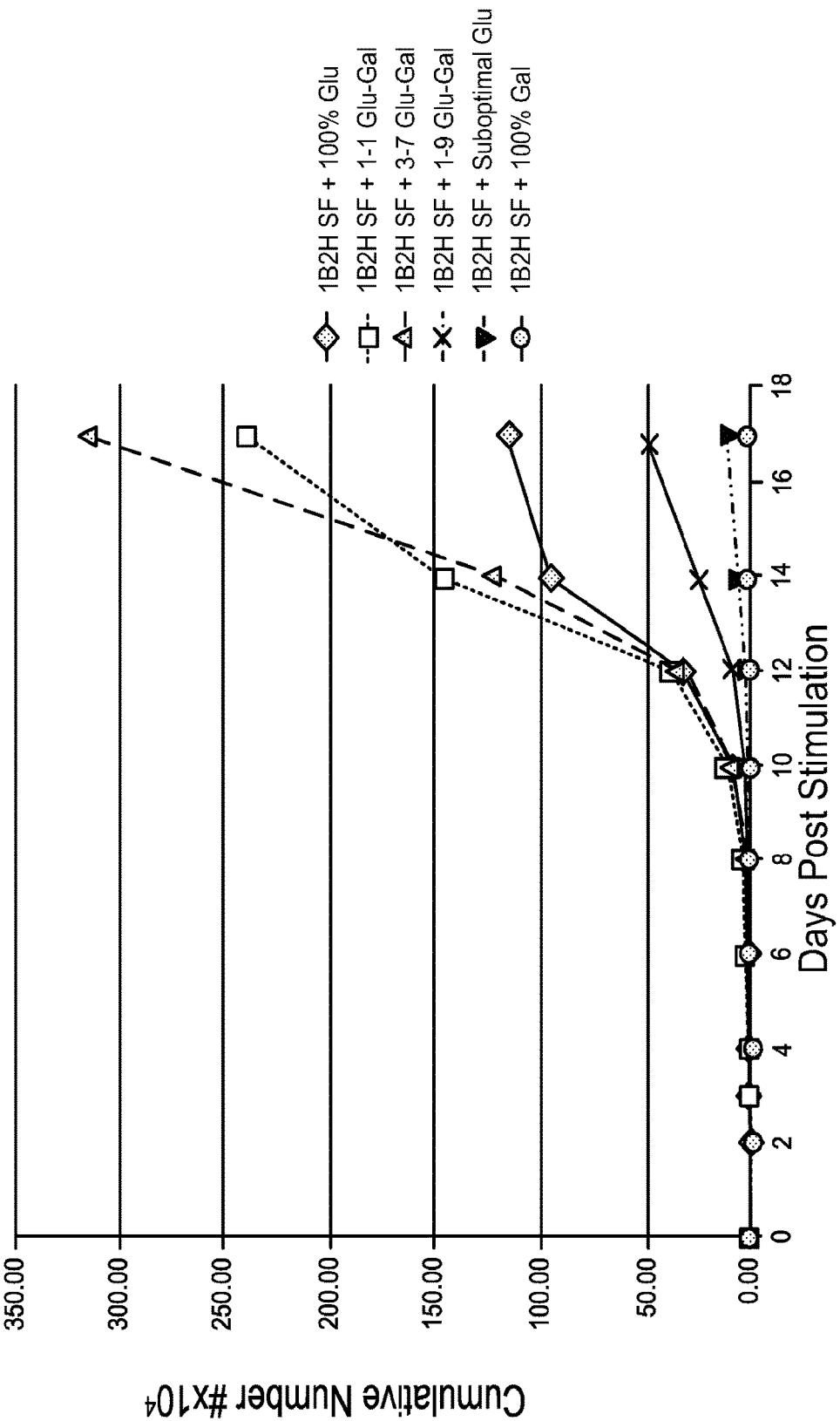
FIG. 28 is a graph depicting that ND405 central memory CD4+ T cell expansion in serum free media with varying concentrations of glucose and galactose.
Figure 29:
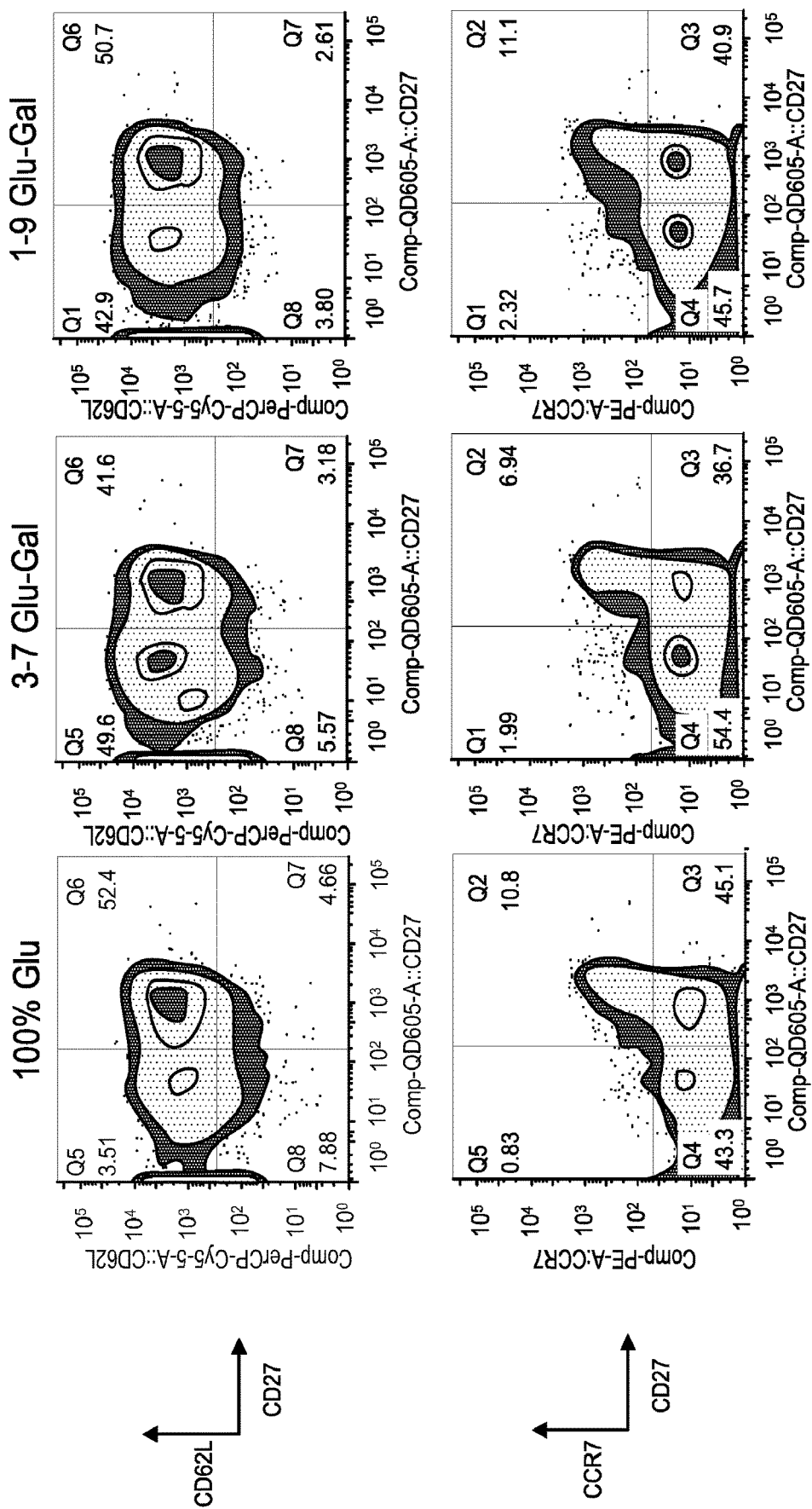
FIG. 29 is a series of FACS gating results demonstrating the phenotype of expanded CM CD4+ T cells. Central memory T cells were expanded using the serum free media described herein.
Figure 30:
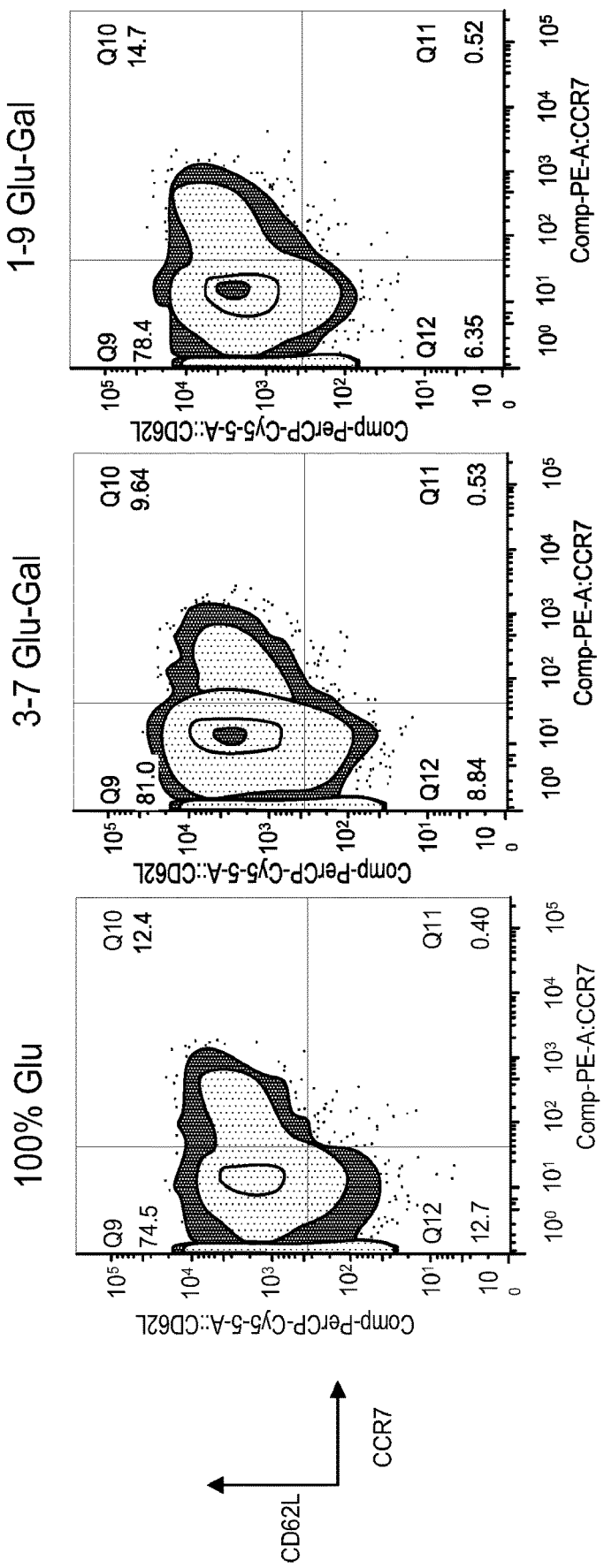
FIG. 30 is a series of FACS gating results demonstrating the phenotype of expanded CM CD4+ T cells. Central memory T cells were expanded using the serum free media described herein.

There is a loss of IFNγ production in naïve CD4+ T cells grown in limited glucose media as evidenced by the FACS analyses results of FIG. 24. Furthermore, as demonstrated in FIG. 25 and FIG. 26, there was also a loss of IFNγ production in naïve CD4+ T cells grown in limited glucose:galactose media. This demonstrated that limited glucose:galactose media was at least equal to limited glucose media for generating expanded T cells. There was also comparable cytokine production in naïve CD4+ T cell conditions, see FIG. 27. Populations of memory T cells were also expanded using limited glucose:galactose serum free media. As demonstrated in FIG. 28, ND405 central memory CD4+ T cell expansion was carried out in serum free media with varying concentrations of glucose and galactose. Central memory T cells were expanded using the serum free media described herein. The phenotype of expanded CM CD4+ T cells is depicted in FIG. 29 and FIG. 30.

Figure 31:
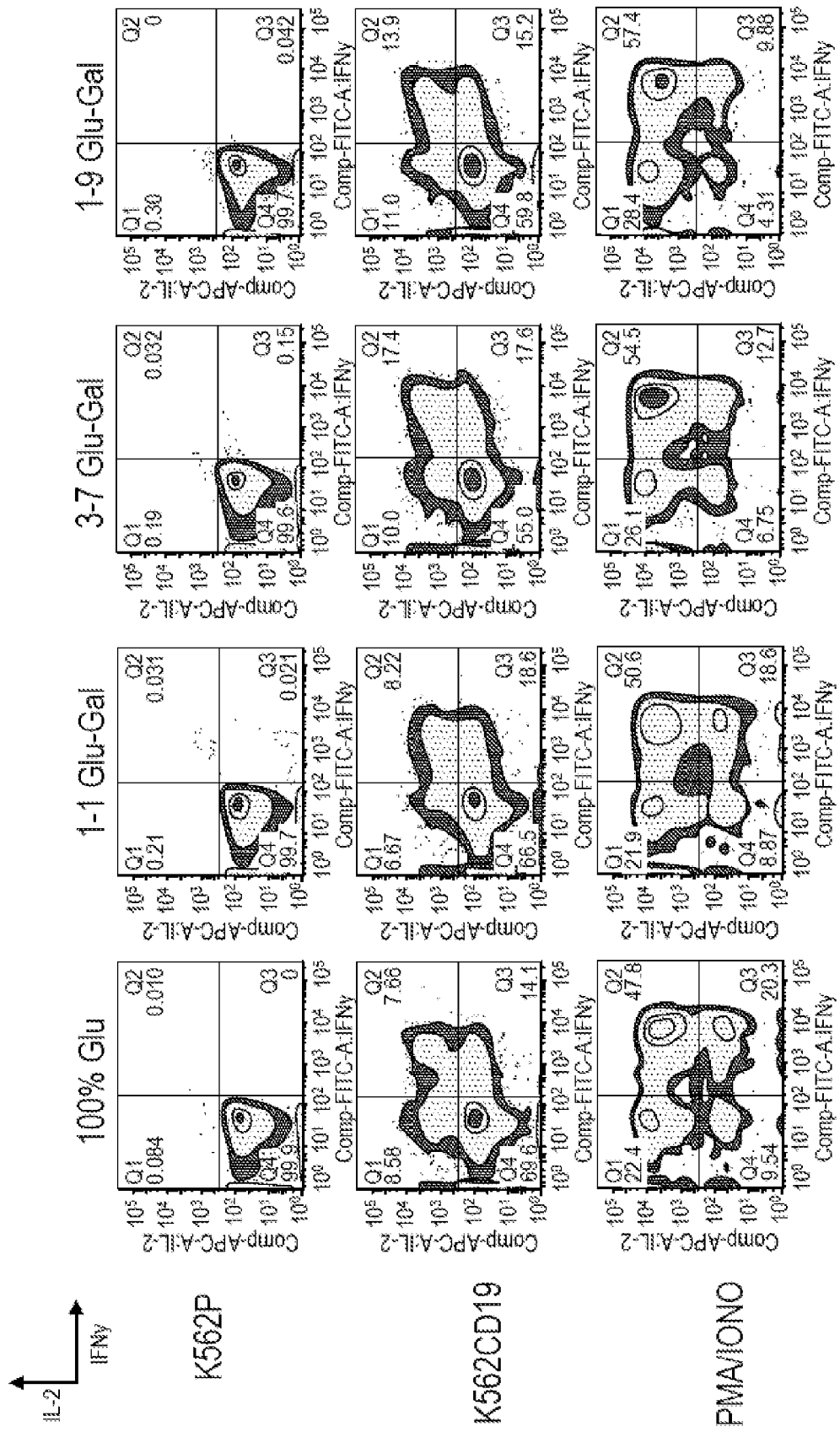
FIG. 31 is a series of FACS gating results demonstrating that limiting glucose in media has no effect on CM CD4+ T cells to produce IFNγ.
Figure 32B:
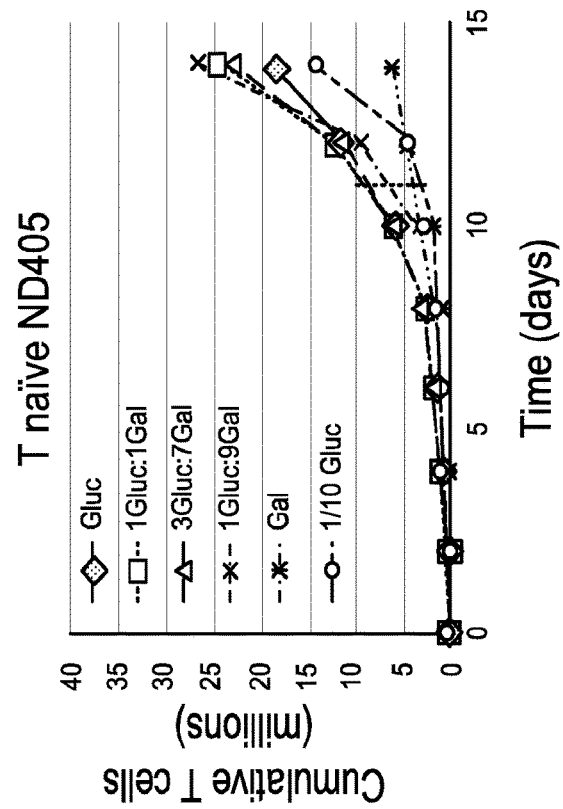
FIG. 32A and FIG. 32B is a series of graphs demonstrating that T cell subsets respond differently to galactose.
Figure 32A:
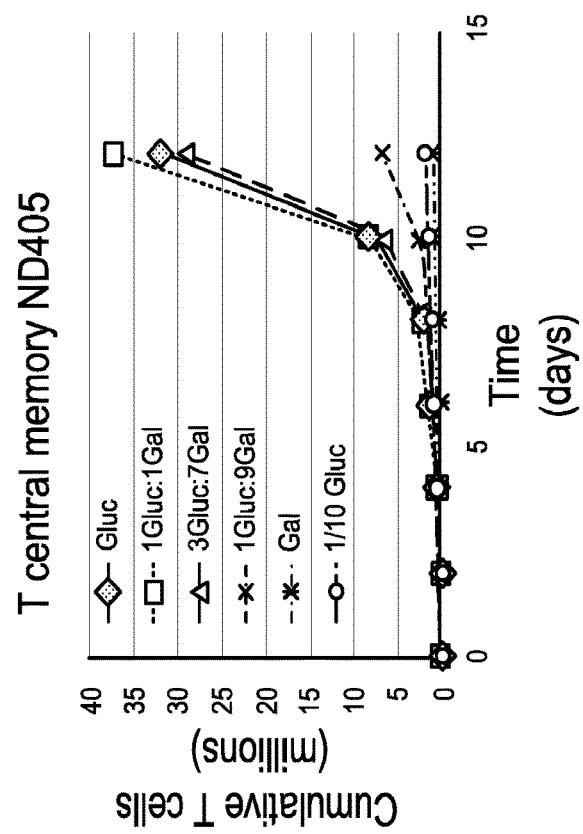
Figure 33:
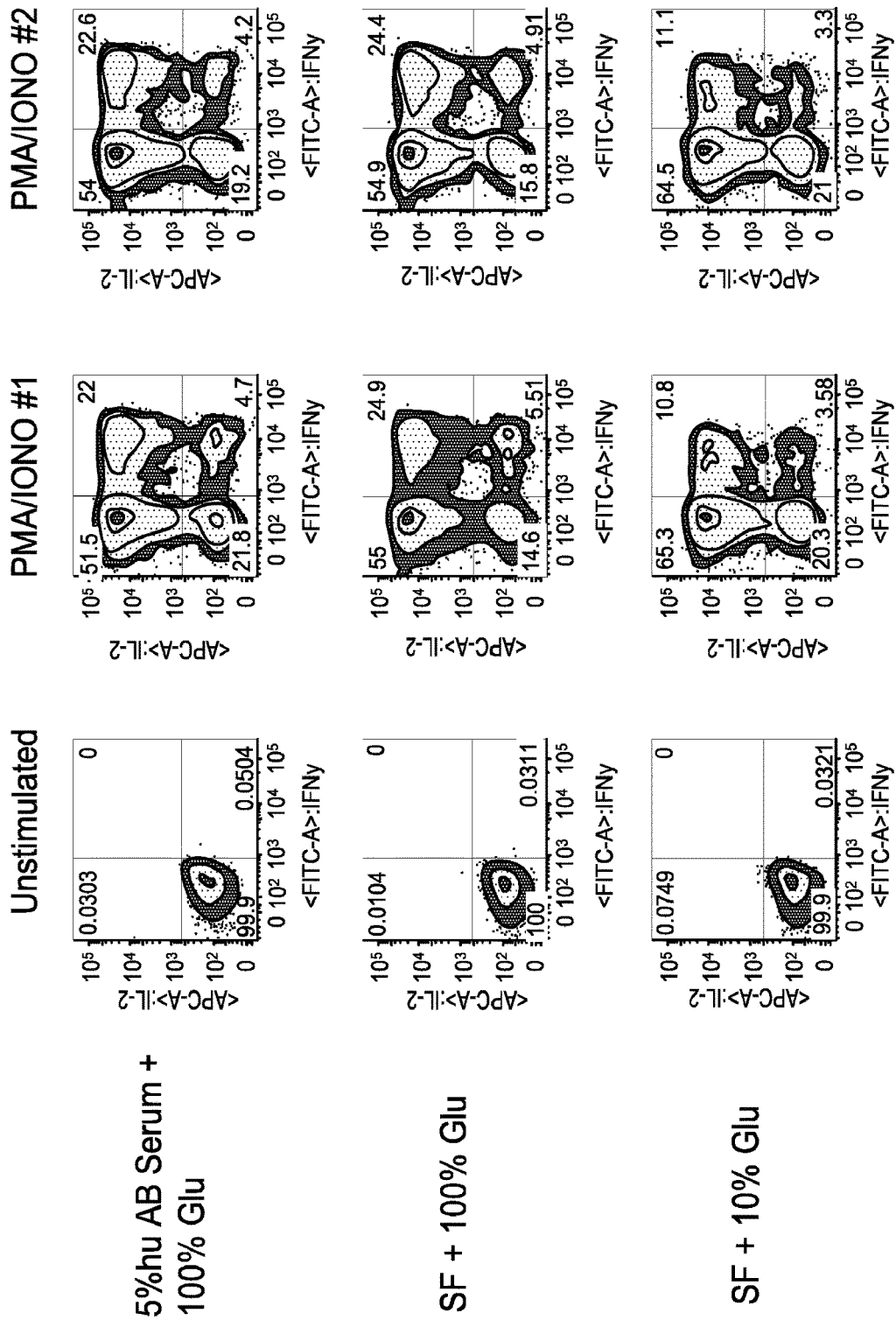
FIG. 33 is a series of FACS gating results demonstrating that there is loss of IFNγ production in CD4+ naïve T cells grown in limited glucose:galactose media.
Figure 34:
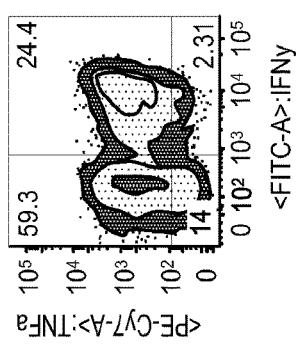
FIG. 34 is a series of FACS gating results demonstrating that that there is loss of IFNγ production in CD4+ naïve T cells grown in limited glucose:galactose media.
Figure 34:
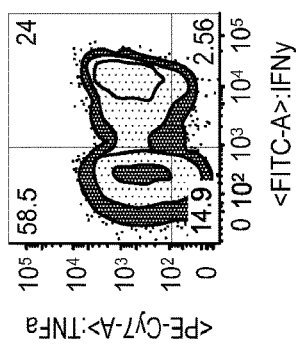
Figure 34:
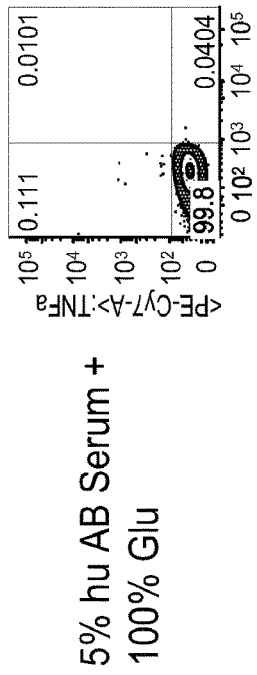
Figure 34:
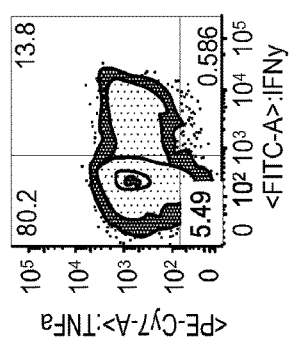
Figure 34:
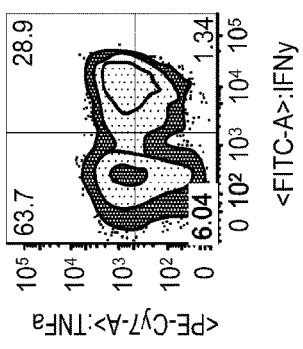
Figure 34:
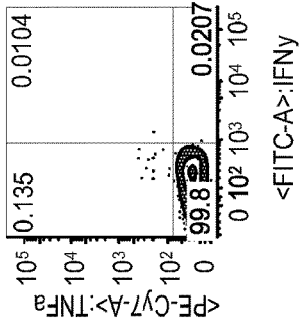
Figure 34:
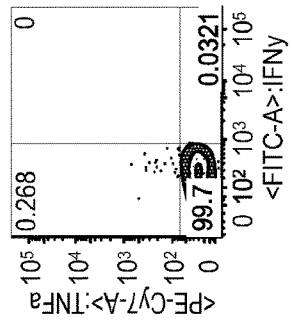
Figure 35:
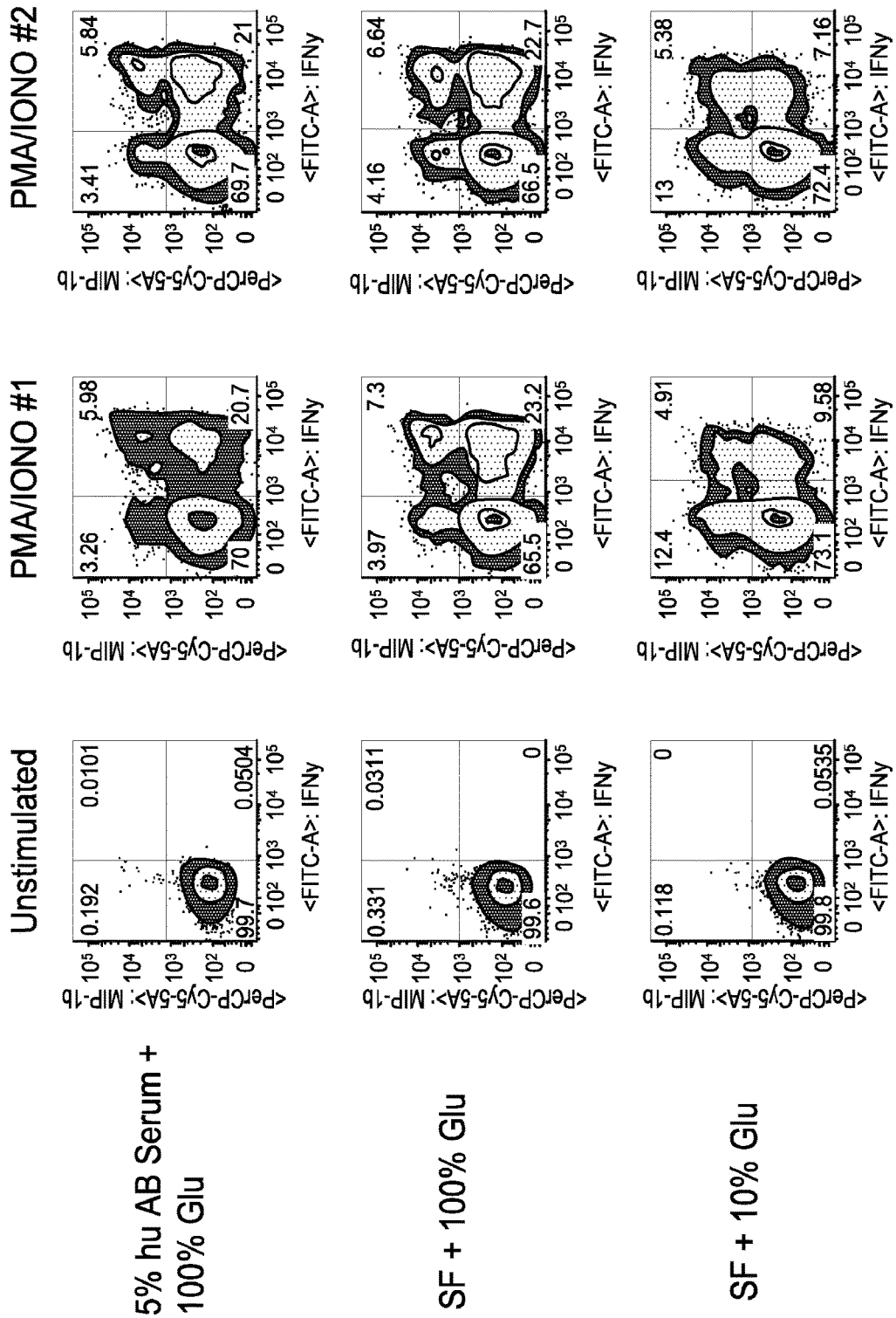
FIG. 35 is a series of FACS gating results demonstrating that that there is loss of IFNγ production in CD4+ naïve T cells grown in limited glucose:galactose media.
Figure 36:
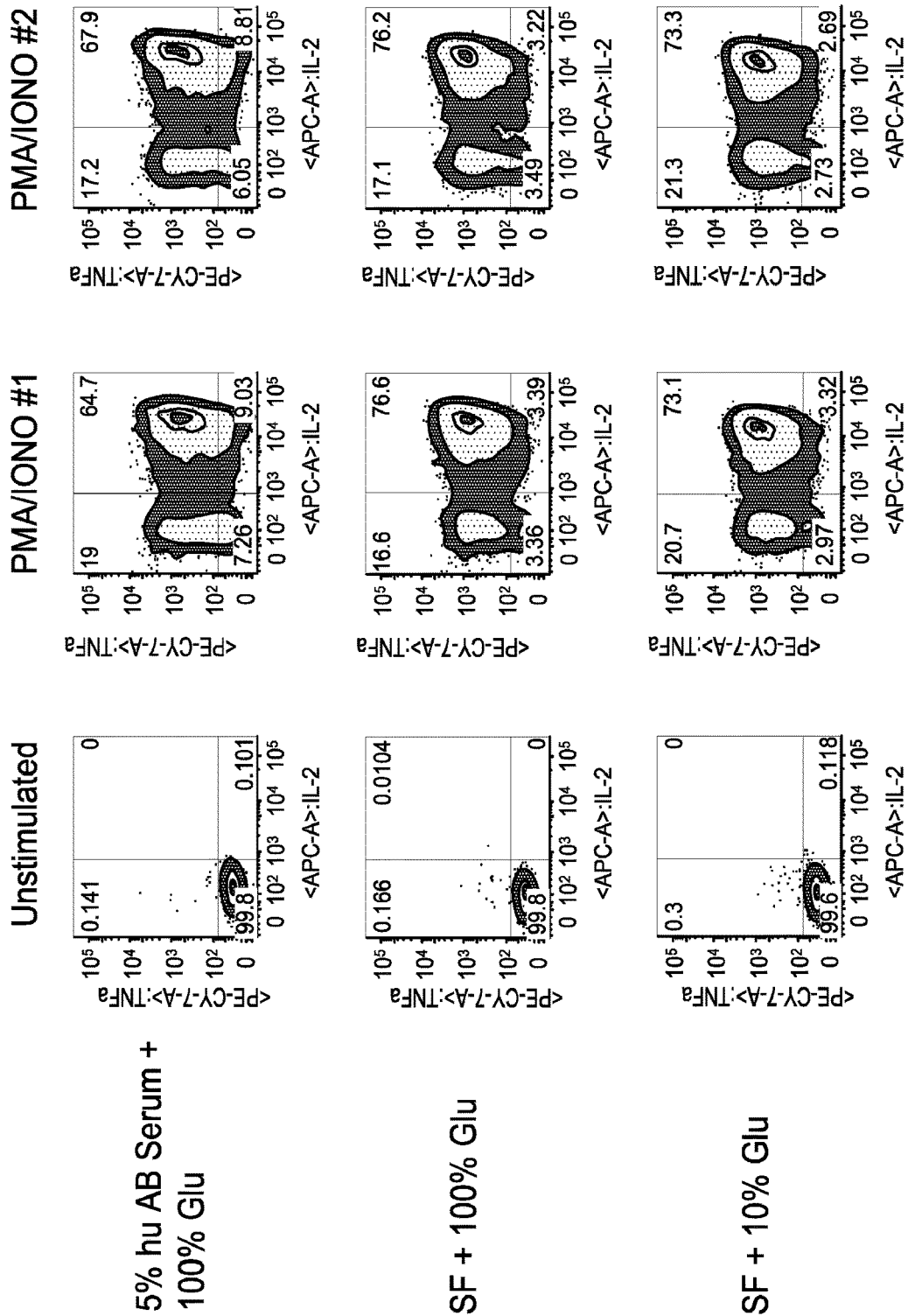
FIG. 36 is a series of FACS gating results demonstrating that there is no reduction in cytokine production in CD4+ naïve T cells grown in limited glucose media for TNFα and IL-2.
Figure 37:
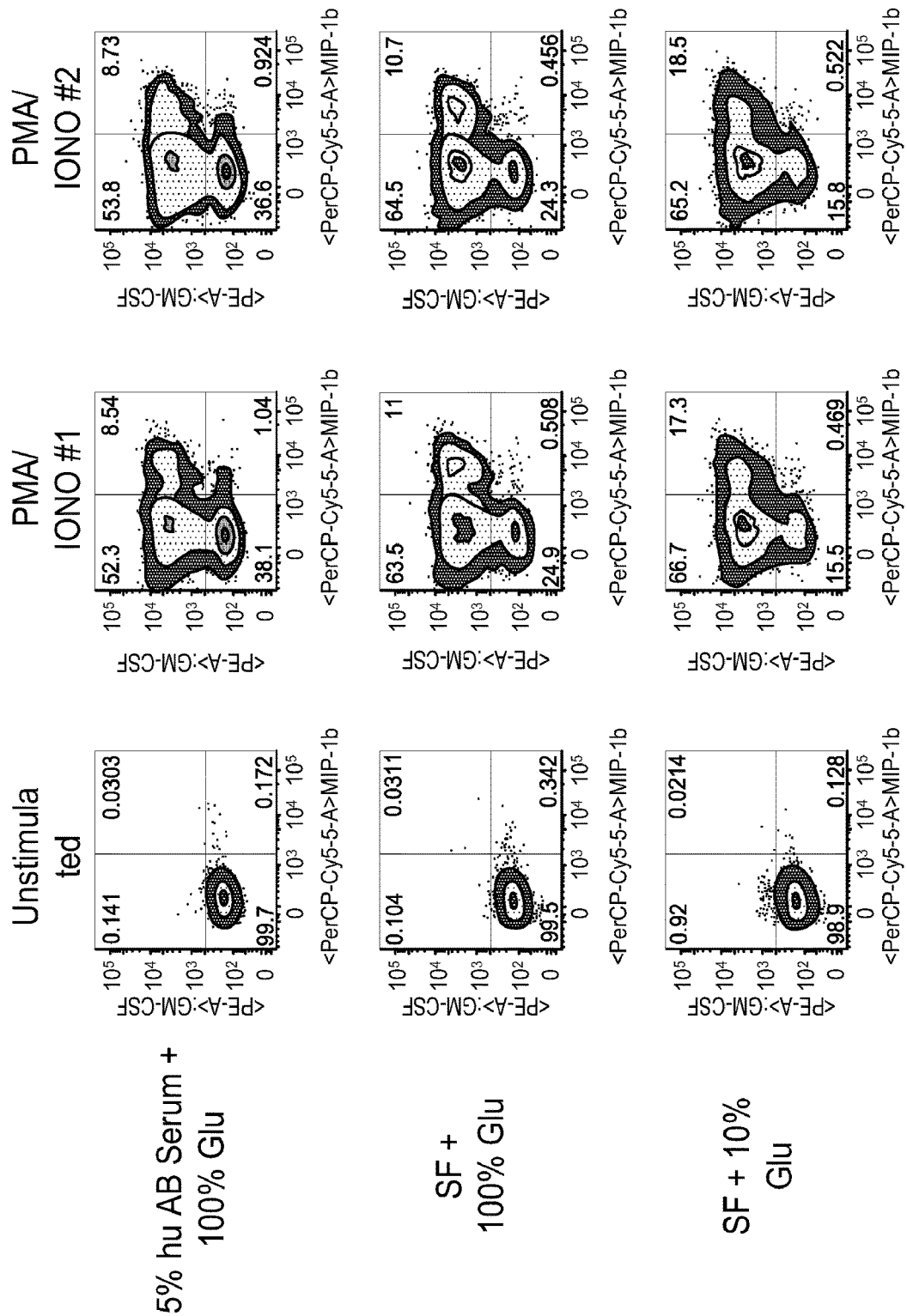
FIG. 37 is a series of FACS gating results demonstrating that there is no reduction in cytokine production in CD4+ naïve T cells grown in limited glucose media for GM-CSF and MIP-1b.

Limiting glucose in media has no effect on the ability of CM CD4+ T cells to produce IFNγ (see FIG. 31). T cell subsets respond differently to galactose. FIG. 32A demonstrates T central memory cells ND405 responding to galactose. FIG. 32B demonstrates T naive cells ND405 responding to galactose. There is loss of IFNγ production in CD4+ naïve T cells grown in limited glucose:galactose media (see FIG. 33, FIG. 34, and FIG. 35). There is no reduction in cytokine production in CD4+ naïve T cells grown in limited glucose media for TNFα and IL-2, as demonstrated in FIG. 36. Also, as depicted in FIG. 37, there is no reduction in cytokine production in CD4+ naïve T cells grown in limited glucose media for GM-CSF and MIP-1b.

Example 13. Methods and Materials

T cell isolation: De-identified, purified human CD4 and CD8 T cells were obtained from the Human Immunology Core of the University of Pennsylvania under an IRB approved protocol. De-identified frozen apheresis bags were obtained from multiple myeloma patients. After thawing, CD4 and CD8 T cells were purified using RosetteSep™ (Cat #15062 and 15063) per manufacturer's recommendations. T cells were expanded in media. Differentiation status of expanded T cells was assessed by staining with antibodies against CD3, CD4, CD8, CD45RA, CD27 and CCR7. Sequential gating was used to characterize T cells as naïve (TN: CD45RA+/CD27+/CCR7+), terminally differentiated effectors (TTS: CD45RA+/CD27−/CCR7−), central memory (TCM: CD45RA−/CD27+/CCR7+); and effector memory (TEM: CD45RA−/CD27−/CCR7−). Flow cytometric analysis was performed in a Beckton-Dickinson LSR-II analyzer. Expansion of patient T cells was analyzed over time by counting on a Beckman-Coulter Multisizer 3 and normalized to the expansion level in X-VIVO™ 15 with 5% human AB serum for each patient cell material.

T cell activation, transduction and expansion: Unless indicated otherwise, CD4 and CD8 T cells were mixed at a 1:1 ratio, placed in the indicated media, and stimulated using anti-CD3 and anti-CD28 coated beads (Thermofisher, Cat. No. 1141D). After 24 hours, T cells were transduced with concentrated lentiviral supernatant as previously described. T cells were counted every other day starting on Day 3 and cell size was monitored on Multisizer™ 3 Coulter Counter® (Beckman Coulter, Indianapolis Ind.). After counting, cells were diluted to 500,000 per ml using fresh media. Cells were cultured until their mean cell volume approached 250 fl and they stopped accumulating.

Flow cytometry and Intracellular Cytokine Staining: CD27 (Biolegend CAT #302830) CCR7 Biolegend CAT #353218) labelled antibodies were used to stain the expanded T cell populations. Expression of the CD19 CARs was detected using the biotinylated F(ab')2 fragment from goat antimouse IgG sera (specific for scFvs of murine origin; Jackson ImmunoResearch) followed by staining with streptavidin-PE (BD Biosciences/Pharmingen). Intracellar cytokine staining was performed as previously described. Briefly, after T cells stopped expanding, CD3/28 beads were removed by magnetic separation. The following day they were mixed with K562s expressing CD19 at a ratio of 1:2 and incubated for 5 hours with GolgiStop (BD). Surface CD4 (Biolegend 317433) and CD8 (BD Cat 560273) staining was performed, samples were fixed and the following day intracellular staining, with an LSR II flow cytometer (BD Biosciences, San Jose Calif.) and FlowJo software (Tree Star Inc., Ashland OR). The following antibodies were used for intracellular staining: -IL-2 (BD 554567), IFNγ (BD 552882, TNF (BD 557647), MIP-1β (BD 560688).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for culturing a population of cells comprising one or more T cells comprising:
    (a) incubating T cells from a subject with serum-free media comprising glucose and galactose, wherein the glucose:galactose ratio ranges from 10:90 to 90:10;
    (b) growing the culture of T cells for at least 10 days; and optionally
    (c) harvesting the T cells from the culture.

2. The method of claim 1, wherein growing further comprises screening the T cells for the presence or absence of makers associated with a desired T cell type.

3. The method of claim 2, wherein the markers are selected from the group comprising CD3, CD4, CD8, CCR7, CD19, CD27, CD28, and CD45RA.

4. The method of claim 1, wherein the media further comprises one or more lipids.

5. The method of claim 4 wherein the lipids are selected from the group comprising one or more of fatty acids, cholesterol, arachidonic acid, linoleic acid, linolenic acid, myristic acid, oleic acid, palmitic acid, palmitoleic acid and stearic acid.

6. The method of claim 1, wherein one or more subpopulations of T cell types is selectively expanded.

7. The method of claim 6, wherein the one or more subpopulations of T cells are selected from the group consisting of: regulatory T cells, Th17 T cells, Th9 T cells, memory T cells, naive T cells, and engineered T cells.

8. The method of claim 7, wherein the one or more subpopulations of T cells are selected from the group consisting of regulatory T cell, Th17 T cells, memory T cells, and naive T cells.

9. The methods of claim 1, wherein the T cells have greater retention of phenotype, greater expansion, greater potency, and/or higher transduction efficiency when compared to cells not cultured in the media.

10. The method of claim 1, wherein the glucose:galactose in a ratio ranging from 25:75 to 75:25.

11. The method of claim 1, wherein the number of viable T cells increases to from about 50 million to about 75 million when cultured for 12 day, wherein the initial number of T cells is about 1 million.

12. The method of claim 11, wherein the number of viable T cells increases to from about 50 million to about 75 million when cultured for 12 day, wherein the initial number of T cells is about 1 million.

\* \* \* \* \*